US012799539B2

(12) United States Patent
Tammela

(10) Patent No.: US 12,799,539 B2

(45) Date of Patent: Nov. 17, 2026

(54) METHODS FOR IDENTIFYING AND TREATING HIGH-PLASTICITY CELL STATE DRIVING TUMOR PROGRESSION IN LUNG CANCER

(71) Applicants: Memorial Sloan-Kettering Cancer Center, New York, NY (US); Sloan-Kettering Institute for Cancer Research, New York, NY (US); Memorial Hospital for Cancer and Allied Diseases, New York, NY (US)

(72) Inventor: Tuomas Tammela, New York, NY (US)

(73) Assignees: Memorial Sloan-Kettering Cancer Center, New York, NY (US); Memorial Hospital for Cancer and Allied Diseases, New York, NY (US); Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 17/666,999

(22) Filed: Feb. 8, 2022

(65) Prior Publication Data

US 2022/0259673 A1 Aug. 18, 2022

Related U.S. Application Data

(60) Provisional application No. 63/147,536, filed on Feb. 9, 2021.

(51) Int. Cl.

| | |
|---|---|
| ***C12Q 1/6886*** | (2018.01) |
| ***A61K 38/17*** | (2006.01) |
| ***A61K 39/395*** | (2006.01) |
| ***A61K 40/11*** | (2025.01) |
| ***A61K 40/31*** | (2025.01) |
| ***A61K 40/33*** | (2025.01) |
| ***A61K 40/42*** | (2025.01) |
| ***A61K 45/06*** | (2006.01) |
| ***C07K 16/24*** | (2006.01) |
| ***C12N 15/113*** | (2010.01) |
| ***C12Q 1/6881*** | (2018.01) |
| ***G01N 33/5752*** | (2026.01) |

(52) U.S. Cl.

CPC ........ *C12Q 1/6886* (2013.01); *A61K 38/1774* (2013.01); *A61K 39/3955* (2013.01); *A61K 40/11* (2025.01); *A61K 40/31* (2025.01); *A61K 40/33* (2025.01); *A61K 40/4241* (2025.01); *A61K 40/4253* (2025.01); *A61K 40/4258* (2025.01); *A61K 45/06* (2013.01); *C07K 16/24* (2013.01); *C12N 15/1135* (2013.01); *C12Q 1/6881* (2013.01); *G01N 33/5752* (2026.01); *A61K 2239/55* (2023.05); *C12N 2320/31* (2013.01); *C12Q 2600/158* (2013.01)

(58) Field of Classification Search

CPC .................................................. C12Q 1/6886

USPC ..................................................... 424/174.1

See application file for complete search history.

(56) References Cited

U.S. PATENT DOCUMENTS

2018/0185284 A1* 7/2018 Vivas-Mejia ........ A61K 9/0019
2019/0194124 A1* 6/2019 Freeman ............. A61K 31/417

FOREIGN PATENT DOCUMENTS

WO WO 2021/035048 A1 * 2/2021

OTHER PUBLICATIONS

Mohell et al (Cell Death and Disease, 2015, 6(e1794).*
Zhang et al (Biomaterials, 2013, 34: 8459-8468).*
Park et al (Invest New Drugs, 2010, 28: 791-799).*
Hu et al (Clin Can Res, 2000, 6: 880-886).*
Li et al (Cancer Imm Res, 2018, 6(2): 178-188).*
Lo Sardo et al (Cancers, 2018, 10 (137): 1-29).*
Pao et al (Lancet Oncol, 2011, 12: 175-180).*
Wang et al (PLOS One, 2014, 9(11): e112150, 7 pages).*
Yin et al (OncoTargets and Therapy, 2019, 12: 9227-9237).*
Ma et al (Scientific Reports, 2019, 9(20021): 1-9).*
Hu et al (OncoTargets and Therapy, 2019, 12: 9849-9860).*
Diaz et al (BMC Cancer, 2010, 10(188): 1-10).*
Tièche et al (Neoplasia, 2019, 21(2): 185-196).*
De Sousa et al (Tumor Heterogeneity, Pathobiology, 2018, 85: 96-107).*
Hirasawa et al (Br. J. Cancer, 1994, 70: 466-473).*
Huang et al (Theranostics, 2017, 7(16): 4013-4028).*
Marjanovic et al., "Emergence of a High-Plasticity Cell State during Lung Cancer Evolution", Cancer Cell, vol. 38, pp. 229-246, Aug. 10, 2020.

* cited by examiner

*Primary Examiner* — Sean E Aeder

(74) *Attorney, Agent, or Firm* — Foley & Lardner LLP

(57) ABSTRACT

The present disclosure provides methods for detecting and inhibiting high-plasticity cell state (HPCS) in patients diagnosed with or at risk for lung cancer. Also disclosed herein are methods for reducing the expression and/or activity of SLC4A11, OC2, MYC, RELB, LIF, NFKB2, FOSL2, ATF4, and/or YAP to inhibit HPCS in lung cancer.

11 Claims, 8 Drawing Sheets

Specification includes a Sequence Listing.

FIG. 3

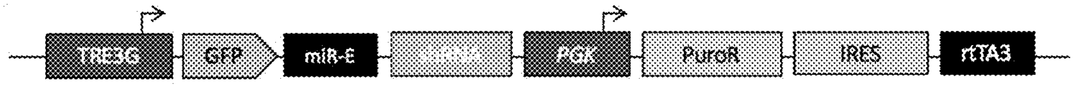

| Gene (.starting base) | Sequence | SEQ ID NO |
|---|---|---|
| Maff(.587) | tgctgttgacagtgagcgACAGCGTCATCACCATCGTCAAtagtgaagccacagatgtaTTGACGATGGTGATGACGCTGGtgcctactgcctcgga | 1 |
| Fhl2(.467) | tgctgttgacagtgagcgATACCCGCAAGATGGAATACAAtagtgaagccacagatgtaTTGTATTCCATCTTGCGGGTACtgcctactgcctcgga | 2 |
| Slc4a11 | tgctgttgacagtgagcgATCGCAAGTATCTGAAATTGAAtagtgaagccacagatgtaTTCAATTTCAGATACTTGCGAGtgcctactgcctcgga | 3 |
| Itga2 | tgctgttgacagtgagcgACTCGTGGATGTTGTAGTTGTAtagtgaagccacagatgtaTACAACTACAACATCCACGAGGtgcctactgcctcgga | 4 |
| Relb(.286) | tgctgttgacagtgagcgACAGGACCACAGATGAATTGGAtagtgaagccacagatgtaTCCAATTCATCTGTGGTCCTGGtgcctactgcctcgga | 5 |
| Lif1(.1890) | tgctgttgacagtgagcgCGACAGGTAGCATAAAGTAGAAtagtgaagccacagatgtaTTCTACTTTATGCTACCTGTCTtgcctactgcctcgga | 6 |
| Nfkb2(.152) | tgctgttgacagtgagcgACAGAGATATGGACAATTGCTAtagtgaagccacagatgtaTAGCAATTGTCCATATCTCTGGtgcctactgcctcgga | 7 |
| Fosl2(.752) | tgctgttgacagtgagcgACAGAAGGAGAAGGAGAAGCTAtagtgaagccacagatgtaTAGCTTCTCCTTCTCCTTCTGCtgcctactgcctcgga | 8 |
| Atf4(.1383) | tgctgttgacagtgagcgATGGAGTTAGTTTGACAGCTAAtagtgaagccacagatgtaTTAGCTGTCAAACTAACTCCAGtgcctactgcctcgga | 9 |
| Cldn4-951 | tgctgttgacagtgagcgCAACCCGGACTGTGCAAAGTTAtagtgaagccacagatgtaTAACTTTGCACAGTCCGGGTTTtgcctactgcctcgga | 10 |
| Myc | tgctgttgacagtgagcgCCGACGAGACCTTCATCAAGAAtagtgaagccacagatgtaTTCTTGATGAAGGTCTCGTCGTtgcctactgcctcgga | 11 |
| Yap1(.735) | tgctgttgacagtgagcgCCACAACGATCAGACAACAACAtagtgaagccacagatgtaTGTTGTTGTCTGATCGTTGTGAtgcctactgcctcgga | 12 |
| Onecut2(.2361) | tgctgttgacagtgagcgACACAACGAAGATATACAGAAAtagtgaagccacagatgtaTTTCTGTATATCTTCGTTGTGCtgcctactgcctcgga | 13 |
| shRenilla | TGCTGTTGACAGTGAGCGCAGGAATTATAATGCTTATCTATAGTGAAGCCACAGATGTATAGATAAGCATTATAATTCCTATGCCTACTGCCTCGGA | 14 |

FIG. 6A
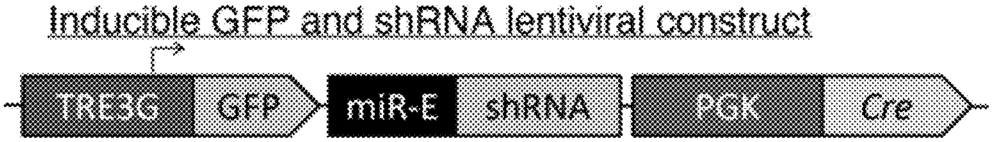
FIG. 6B
Degenerate barcode shRNA barcode Specific amplicon Seq
CCCGGTNNNNNAANNNNNTTNNNNNAA[TGTCTAGT]ACTAATCA[CTGGATAAAACTGCGGTCGT]
FIG. 6C
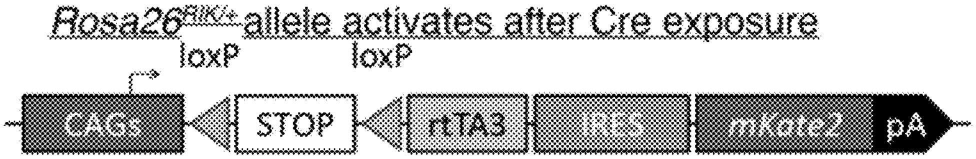
FIG. 6D
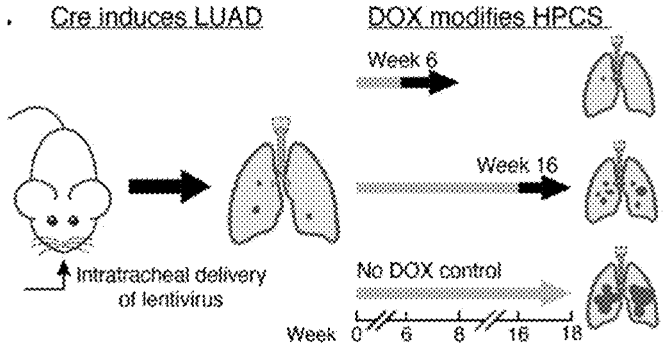
FIG. 6E
Validation of inducible system in KP-RIK mice
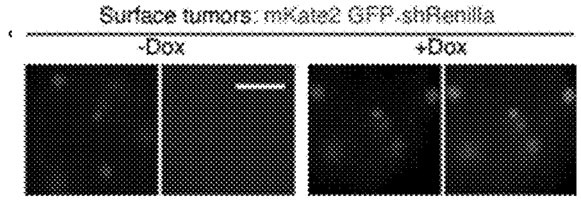
FIG. 6F
Validation of inducible system in KP-RIK mice
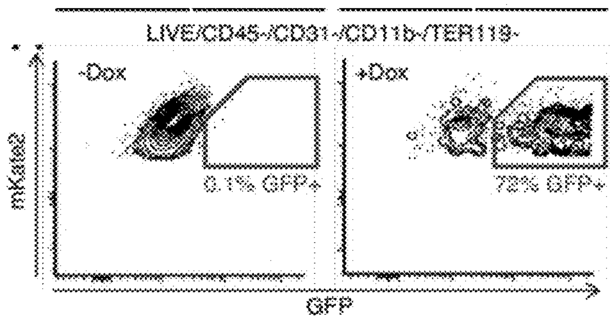

METHODS FOR IDENTIFYING AND TREATING HIGH-PLASTICITY CELL STATE DRIVING TUMOR PROGRESSION IN LUNG CANCER

CROSS-REFERENCE TO RELATED APPLICATIONS

This application claims the benefit of and priority to U.S. Provisional Patent Application No. 63/147,536, filed Feb. 9, 2021, the entire contents of which is incorporated herein by reference.

SEQUENCE LISTING

The instant application contains a Sequence Listing which has been submitted electronically in ASCII format and is hereby incorporated by reference in its entirety. Said ASCII copy, created on Mar. 30, 2022, is named 115872-2457_SL.txt and is 70,573 bytes in size.

TECHNICAL FIELD

The present technology relates generally to methods for detecting and eliminating high-plasticity cell state (HPCS) in patients diagnosed with or at risk for lung cancer. Also disclosed herein are methods for reducing the expression and/or activity of SLC4A11, OC2, MYC, RELB, LIF, NFKB2, FOSL2, ATF4, and/or YAP to inhibit HPCS in lung cancer.

BACKGROUND

The following description of the background of the present technology is provided simply as an aid in understanding the present technology and is not admitted to describe or constitute prior art to the present technology.

Cellular states capable of promoting tumor progression and resisting therapies exist in heterogeneous tumors. Tumor evolution from a single cell into a malignant, heterogeneous tissue remains poorly understood. The emergence and maintenance of cellular heterogeneity is driven by a high-plasticity cell state (HPCS) that is common to mouse and human lung tumors. See Marjanovic et al., 2020, *Cancer Cell* 38, 229-246. HPCS harbors high tumorigenic capacity, is drug resistant, and is associated with poor patient prognosis.

Accordingly, there is an urgent need for methods that are useful for detecting and eliminating HPCS in lung cancer.

SUMMARY OF THE PRESENT TECHNOLOGY

In one aspect, the present disclosure provides a method for detecting the presence of high-plasticity cell state (HPCS) in a lung cancer sample obtained from a patient comprising: detecting the presence of HPCS in the lung cancer sample by detecting SLC4A11 mRNA or polypeptide levels in the lung cancer sample that are at least 5% higher compared to that observed in a reference sample. The SLC4A11 polypeptide levels may be detected via Western Blotting, flow cytometry, Enzyme-linked immunosorbent assay (ELISA), dot blotting, immunohistochemistry, immunofluorescence, immunoprecipitation, immunoelectrophoresis, High-performance liquid chromatography (HPLC), or mass-spectrometry. Alternatively, the SLC4A11 mRNA levels may be detected via in situ hybridization, reverse transcriptase polymerase chain reaction (RT-PCR), RNA-Seq, Northern blotting, microarray, dot or slot blots, fluorescent in situ hybridization (FISH), electrophoresis, chromatography, or mass spectroscopy. In some embodiments, the lung cancer sample is obtained from a patient diagnosed with or at risk for lung adenocarcinoma.

In one aspect, the present disclosure provides a method for inhibiting high-plasticity cell state (HPCS) in a patient diagnosed with or at risk for lung cancer comprising administering to the patient an effective amount of an immunotherapeutic agent comprising an antibody or antigen binding fragment that specifically binds to SLC4A11. The immunotherapeutic agent may be an antibody drug conjugate, a Bi-specific T-cell engager (BiTE), a CAR T cell, or a tri-specific natural killer cell engager.

In another aspect, the present disclosure provides a method for inhibiting high-plasticity cell state (HPCS) in a patient diagnosed with or at risk for lung cancer comprising administering to the patient an effective amount of at least one inhibitory nucleic acid that specifically hybridizes to one or more of RELB, LIF, NFKB2, FOSL2, ATF4, YAP, OC2 and MYC. The at least one inhibitory nucleic acid may be a siRNA, an antisense nucleic acid, a shRNA, a sgRNA, or a ribozyme. In some embodiments, the at least one inhibitory nucleic acid comprises a nucleic acid sequence selected from the group consisting of: SEQ ID NO: 3, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, or a complement thereof. Additionally or alternatively, in some embodiments, the at least one inhibitory nucleic acid is administered orally, topically, intranasally, systemically, intravenously, subcutaneously, intraperitoneally, intradermally, intraocularly, iontophoretically, transmucosally, or intramuscularly.

Additionally or alternatively, in some embodiments of the methods disclosed herein, the patient displays elevated expression levels of SLC4A11, OC2, MYC, RELB, LIF, NFKB2, FOSL2, ATF4, and/or YAP protein in lung tumor cells prior to treatment. Additionally or alternatively, in certain embodiments, treatment with the at least one inhibitory nucleic acid results in a decrease in SLC4A11, TIGIT and/or Integrin $\alpha 2$ levels in the patient compared to that observed prior to treatment.

In any and all embodiments of the methods disclosed herein, the patient is diagnosed with or at risk for non-small cell lung cancer (NSCLC). The NSCLC subtype may be lung adenocarcinoma (LUAD), squamous cell carcinoma (SCC), or large cell carcinoma. Additionally or alternatively, in some embodiments, the signs or symptoms of lung cancer comprise one or more of incessant coughing, chest pain, shortness of breath, wheezing, coughing up blood, chronic fatigue, weight loss with no known cause, repeated bouts of pneumonia, and swollen or enlarged lymph nodes (glands) inside chest area between the lungs. In certain embodiments, the patient harbors one or more mutations in KRAS, BRAF, P53, EGFR, PIK3CA, HER2, DDR2, PIK3CA, PTEN or H3F3A, and/or one or more gene amplifications in MET, HER2, FGFR1, or PDGFRA, and/or one or more gene rearrangements in ALK, NTRK, NRG1, ROS1, or RET.

In any and all embodiments of the methods disclosed herein, the methods further comprise separately, sequentially or simultaneously administering one or more additional therapeutic agents to the patient. In certain embodiments, the additional therapeutic agents are selected from the group consisting of EGFR-tyrosine kinase inhibitors, phosphatidylinositol 3-kinase/protein kinase B (PI3K/Akt) inhibitors, radiation therapy, and immune checkpoint inhibitors.

Also provided herein are kits for the prevention and/or treatment of HPCS in lung cancer comprising one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP). In some embodiments, the kits comprise a nucleic acid sequence selected from the group consisting of SEQ ID NOs: 3, 5-9, 11-13 or any complement thereof.

BRIEF DESCRIPTION OF THE DRAWINGS

FIG. 1A shows the proportion of LUAD tumors with distinct SLC4A11 expression scores, and FIG. 1B shows exemplary staining of human LUAD tumors from patient-derived xenograft (PDX) models. 61 human lung adenocarcinoma PDX models were stained in parallel for in situ hybridization probes detecting human SLC4A11 (red signal) and were scored for signal abundance using the scoring criteria indicated (0—no staining; 1—<5% cells+; 2—5-25% cells+; 3—25-75% cells; 4—>75% cells).

FIG. 3 shows the shRNA sequences used in the Examples described herein.

FIG. 4A shows that Integrin α2 (Itga2) marks the HPCS. FIG. 4B shows Integrin α2 (green) immunofluorescence (IF) marks subsets of tumor cells (red) in autochthonous KP $Rosa26^{td/Tomato/+}$ tumors. Scale bar: 100 μm. FIGS. 4C-4D show violin plots for Myc and OC2: Expression (gene score) of TF (left) and TF targets (right) in HPCS vs. all other clusters. p values calculated by Mann Whitney U test. IF: Co-localization of TFs (red) and integrin α2 (green).

FIG. 5A: qPCR verification. FIGS. 5B-5C: Experiment workflow. FIG. 5B: Tumor spheres containing an inducible shRNA were grown on Matrigel and placed on doxycycline (2 μg/ml) for 4 days before being harvested for scRNA-Seq. Dox: doxycycline. FIG. 5C: (left) HPCS expression level projected onto scRNA-Seq data, (right) Violin plot of HPCS signature. **p<0.01, Mann Whitney U test.

FIG. 6A: In vivo lentiviral construct with an inducible GFP and shRNA, along with a AT2-specific CreER. FIG. 6B: Schematic of degenerate barcode. FIG. 6B discloses SEQ ID NO: 30. FIG. 6C: Activated RIK allele: rtTA3: reverse tet-transactivator, *I* RES: internal ribosome entry site, m*K* ate2. pA: polyA sequence. FIG. 6D: Schema of experiment. Mice infected with lentivirus (see FIG. 6A) via intratracheal delivery; Cre induces LUAD in AT2 cells. Doxycycline (DOX) introduced at Week 6 or Week 16, with a no DOX arm serving as a control. Tumors will be harvested at 8 or 18 weeks. FIGS. 6E-6F: Validation using a shRenilla lentivirus (see FIG. 6A) in KP-RIK mice 10 weeks post tumor induction. FIG. 6E: Surface tumors. Scale bar: 5 mm. FIG. 6F: FACS plot.

DETAILED DESCRIPTION

Figure 1A:
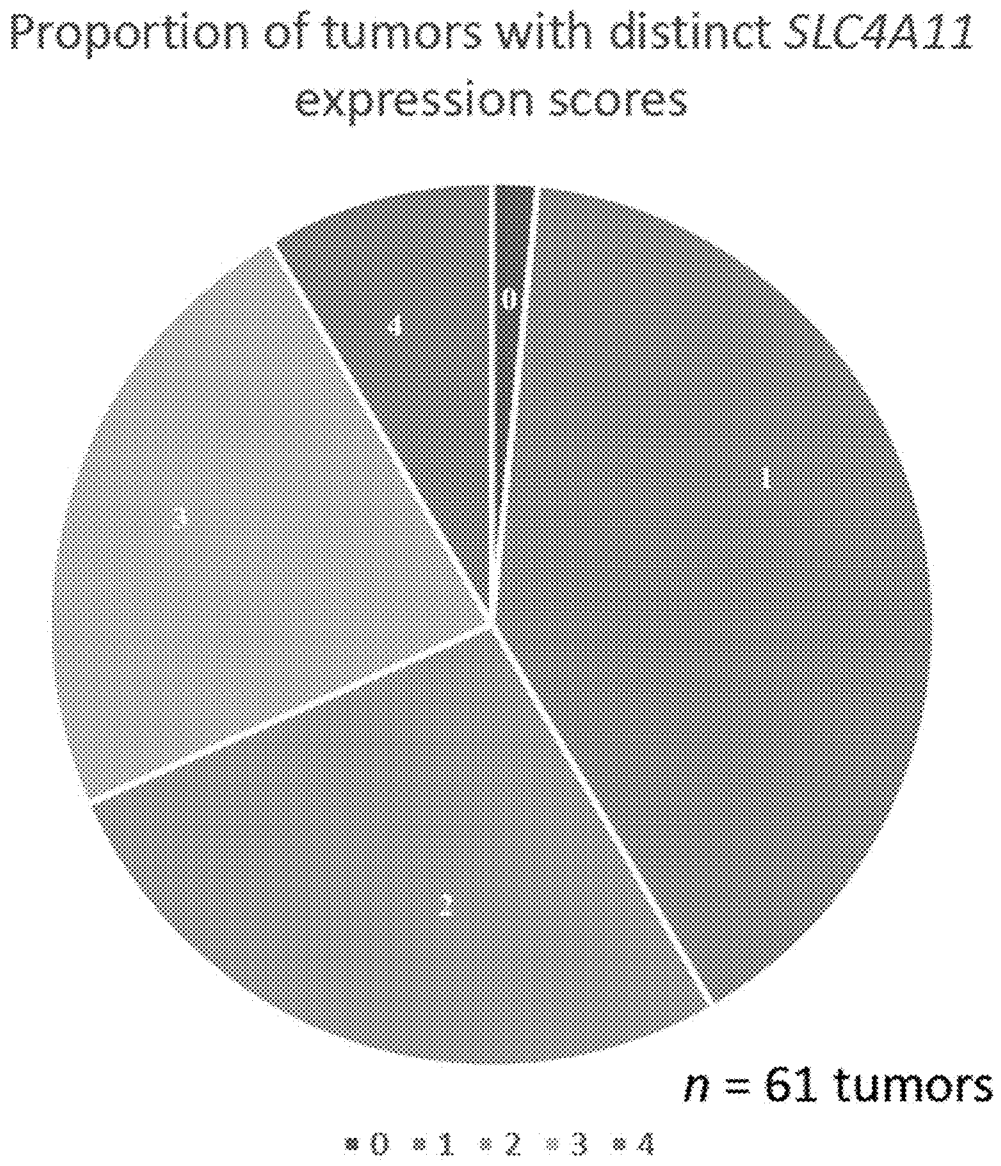
FIGS. 1A-B show that SLC4A11 is expressed in a subset of cells in a majority of human lung adenocarcinomas (LUAD).

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al., eds. (2007) *Current Protocols in Molecular Biology;* the series *Methods in Enzymology* (Academic Press, Inc., N.Y.); MacPherson et al., (1991) *PCR* 1: *A Practical Approach* (IRL Press at Oxford University Press); MacPherson et al., (1995) *PCR* 2: *A Practical Approach;* Harlow and Lane eds. (1999) *Antibodies, A Laboratory Manual;* Freshney (2005) *Culture of Animal Cells: A Manual of Basic Technique,* 5th edition; Gait ed. (1984) *Oligonucleotide Synthesis;* U.S. Pat. No. 4,683,195; Hames and Higgins eds. (1984) *Nucleic Acid Hybridization;* Anderson (1999) *Nucleic Acid Hybridization;* Hames and Higgins eds. (1984) *Transcription and Translation; Immobilized Cells and Enzymes* (IRL Press (1986)); Perbal (1984) *A Practical Guide to Molecular Cloning;* Miller and Calos eds. (1987) *Gene Transfer Vectors for Mammalian Cells* (Cold Spring Harbor Laboratory); Makrides ed. (2003) *Gene Transfer and Expression in Mammalian Cells;* Mayer and Walker eds. (1987) *Immunochemical Methods in Cell and Molecular Biology* (Academic Press, London); and Herzenberg et al., eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning: A Laboratory Manual,* Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual,* Second Edition, Cold Spring Harbor Press, Plainview, N.Y.; Ausubel, F. M. et al. 1994, *Current Protocols in Molecular Biology,* John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention", "prevent", or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, inhibiting HPCS in lung cancer, includes preventing or delaying the initiation of HPCS or preventing a recurrence of one or more signs of HPCS in lung cancer.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

The term "specific" as used herein in reference to an oligonucleotide means that the nucleotide sequence of the oligonucleotide has at least 12 bases of sequence identity with a portion of a target nucleic acid when the oligonucleotide and the target nucleic acid are aligned. An oligonucleotide that is specific for a target nucleic acid is one that, under the stringent hybridization or washing conditions, is capable of hybridizing to the target nucleic acid of interest and not substantially hybridizing to nucleic acids which are not of interest. Higher levels of sequence identity are desirable and include at least 75%, at least 80%, at least 85%, at least 90%, at least 95% or at least 98% sequence identity.

The term "stringent hybridization conditions" as used herein refers to hybridization conditions at least as stringent as the following: hybridization in 50% formamide, 5×SSC, 50 mM $Na_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "subject", "patient", or "individual" can be an individual organism, a vertebrate, a mammal, or a human. In some embodiments, the subject, patient or individual is a human.

As used herein, the terms "target sequence" and "target nucleic acid sequence" refer to a specific nucleic acid sequence to be modulated (e.g., inhibited or downregulated).

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder;

(iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Inhibitory Nucleic Acids of the Present Technology

In one aspect, the present disclosure provides inhibitory nucleic acids (e.g., sgRNAs, antisense RNAs, ribozymes, or shRNAs) that inhibit expression and/or activity of SLC4A11, OC2, MYC, RELB, LIF, NFKB2, FOSL2, ATF4, and/or YAP. The mammalian nucleic acid sequences of SLC4A11, OC2, MYC, RELB, LIF, NFKB2, FOSL2, ATF4, and YAP are known in the art (e.g., NCBI Gene IDs: 83959, 9480, 4609, 5971, 3976, 4791, 2355, 468, and 10413). The inhibitory nucleic acids of the present technology may comprise a nucleic acid molecule that is complementary to a portion of a nucleic acid sequence encoding a gene selected from among SLC4A11, OC2, MYC, RELB, LIF, NFKB2, FOSL2, ATF4, and YAP. In some embodiments, the inhibitory nucleic acids (e.g., sgRNAs, antisense RNAs, ribozymes, or shRNAs) target at least one exon and/or intron of a gene selected from among SLC4A11, OC2, MYC, RELB, LIF, NFKB2, FOSL2, ATF4, and YAP. Exemplary nucleic acid sequences of *Homo sapiens* SLC4A11, OC2, MYC, RELB, LIF, NFKB2, FOSL2, ATF4, and YAP are provided below:

NM_001174090.2 *Homo sapiens* solute carrier family 4 member 11 (SLC4A11), transcript variant 1, mRNA (SEQ ID NO: 15)

```
CTTTTGGACCAACGGCTCTGGCTTCCAGGCGGCCGGGACGCGGTCCCAGGACTGGAGACCGTTGCCTGTC

GGCCCCCGTGTGACCCGGGGCGCGTGACGGGGGTCGGGGGAACTGCGCCTGCAATGGGCGTTTATGGCCC

CCAGGACCGGTCTGAGAGTGAGAAGAGGGATGTGCAGAGAGATCCCCCGCCTTGGCATCCGAGGAGAGAG

GGGGAGAGGCCCGCTCGGGCCCGGTCCCTTCCTCTCGCTGCAGCGGGGCAGGGTTTTCTCAGGAAAACCT

GGATTAGCGAACATGAAAACTCTCCCACCATGTCGCAGAATGGATACTTCGAGGATTCAAGCTACTACAA

GTGTGACACAGATGACACCTTCGAAGCCCGAGAGGAGATCCTGGGGGATGAGGCCTTCGACACTGCCAAC

TCCTCCATCGTGTCTGGCGAGAGTATCCGTTTTTTTGTCAATGTCAACCTTGAGATGCAGGCCACCAACA

CTGAGAATGAAGCGACTTCCGGTGGCTGTGTGCTCCTGCACACCTCCCGAAAGTACCTGAAGTTAAAGAA

CTTCAAGGAAGAGATCCGTGCGCACCGCGACCTAGATGGCTTCCTGGCGCAGGCCAGCATCGTCCTGAAC

GAGACGGCCACCTCCCTGGATAACGTGCTGCGGACCATGCTTCGCCGCTTCGCCAGGGACCCTGACAACA

ATGAGCCCAACTGCAACCTGGACCTGCTCATGGCCATGCTCTTCACCGATGCCGGGGCACCCATGCGGGG

TAAAGTCCACCTGCTGTCAGATACCATCCAAGGGGTCACCGCCACAGTGACAGGGGTGCGGTACCAGCAG

TCGTGGCTCTGCATCATCTGTACCATGAAGGCCCTACAGAAGCGGCACGTGTGCATCAGCCGCCTGGTTC

GCCCACAGAACTGGGGGGAGAATTCCTGTGAGGTTCGGTTCGTCATCCTGGTGCTGGCCCCACCCAAGAT

GAAAAGCACTAAGACTGCGATGGAGGTGGCGCGCACGTTTGCCACCATGTTCTCGGATATCGCCTTCCGC

CAGAAGCTCCTGGAGACCCGCACAGAGGAGGAATTCAAGGAGGCCTTGGTGCATCAGAGACAGCTGCTCA

CCATGGTGAGCCACGGTCCAGTGGCGCCGAGAACGAAGGAACGCAGCACAGTCTCCCTCCCTGCCCACAG

ACACCCAGAGCCCCCAAAGTGCAAGGACTTTGTCCCTTTTGGGAAGGGCATCCGGGAGGACATCGCACGC

AGGTTCCCCTTGTACCCCTTGGACTTCACTGATGGCATTATTGGGAAAAACAAGGCTGTGGGCAAATACA

TCACCACCACCCTGTTCCTCTACTTCGCCTGCCTCCTGCCCACCATCGCTTTCGGGTCTCTCAATGACGA

GAACACAGACGGGGCCATCGACGTGCAGAAGACCATAGCCGGGCAGAGCATCGGGGGCCTGCTCTACGCG

CTCTTCTCTGGGCAGCCATTGGTGATTCTGCTGACCACCGCGCCCCTGGCGCTCTACATCCAGGTGATTC

GTGTCATCTGTGATGACTATGACCTGGACTTCAACTCCTTCTACGCATGGACGGGCCTGTGGAATAGTTT

CTTCCTTGCGCTTTATGCCTTTTTCAACCTCAGCCTGGTCATGAGTCTCTTCAAGAGGTCGACGGAGGAG

ATCATCGCCCTCTTCATTTCCATCACGTTTGTGCTGGATGCCGTCAAGGGCACGGTTAAAATCTTCTGGA

AGTACTACTATGGGCATTACTTGGACGACTATCACACAAAAAGGACTTCATCCCTTGTCAGCCTGTCAGG

CCTCGGCGCCAGCCTCAACGCCAGCCTCCACACTGCCCTCAACGCCAGCTTCCTCGCCAGCCCCACGGAG
```

-continued

CTGCCCTCGGCCACACACTCAGGCCAGGCGACCGCCGTGCTCAGCCTCCTCATCATGCTGGGCACGCTCT

GGCTGGGCTACACCCTCTACCAATTCAAGAAGAGCCCCTACCTGCACCCCTGCGTGCGAGAGATCCTGTC

CGACTGCGCCCTGCCCATCGCGGTGCTCGCCTTCTCCCTCATCAGCTCCCATGGCTTCCGGGAAATCGAG

ATGAGCAAGTTCCGCTACAACCCCAGCGAGAGCCCCTTTGCGATGGCGCAGATCCAGTCGCTGTCCCTGA

GGGCCGTCAGCGGTGCCATGGGCCTCGGCTTCCTGCTGTCCATGCTCTTCTTCATCGAGCAGAACTTGGT

GGCCGCCTTGGTGAATGCACCGGAGAACAGGCTGGTGAAGGGCACTGCCTACCACTGGGACCTCCTGCTC

CTCGCCATCATCAACACAGGGCTGTCTCTGTTTGGGCTGCCTTGGATCCATGCCGCCTACCCCCACTCCC

CGCTGCACGTGCGAGCCCTGGCCTTAGTGGAGGAGCGTGTGGAGAACGGACACATCTATGACACGATTGT

GAACGTGAAGGAGACGCGGCTGACCTCGCTGGGCGCCAGCGTCCTGGTGGGCCTGTCCCTGTTGCTGCTG

CCGGTCCCGCTTCAGTGGATCCCCAAGCCCGTGCTCTATGGCCTCTTCCTCTACATCGCGCTCACCTCCC

TCGATGGCAACCAGCTCGTCCAGCGCGTGGCCCTGCTGCTCAAGGAGCAGACTGCGTACCCCCCGACACA

CTACATCCGGAGGGTGCCCCAGAGGAAGATCCACTACTTCACGGGCCTGCAGGTGCTTCAGCTGCTGCTG

CTGTGTGCCTTCGGCATGAGCTCCCTGCCCTACATGAAGATGATCTTTCCCCTCATCATGATCGCCATGA

TCCCCATCCGCTATATCCTGCTGCCCCGAATCATTGAAGCCAAGTACTTGGATGTCATGGACGCTGAGCA

CAGGCCTTGACTGGCAGACCCTGCCCACGCCCCATTCGCCAGCCCTCCACGTCCTCCCAGGCTGGCTCTG

GAGCTGTGAGGGGAGGTGTAGGTGTGTGGGTGACTGCTCTGTGCTGCGCCTTCTCATGGCTGACTCAGGC

CTGGGGCATCTGGGCATTGTAGGGGTGCAGTGGTATGTGCCCACCCCTCTCCCATTATCCTTTAGCTTTA

GGCCAAGAGCGTTGCTCAGGGCAGCTTCTGCCCAGGGTGGGTGGGACTGAGCAGGATGGATTTTCTTTTG

ATAAAAGAGTCGATGCCTGAAAGAGAAACCATTTCCTTGATTGTGTAAGGAACTTGCTGGACGCACATTA

GAGAATAAAGCTCCTGTTTCTAGGC

NM_004852.3 *Homo sapiens* one cut homeobox 2 (ONECUT2), mRNA (SEQ ID NO: 16)

AGAGCCCTTCTGGACAGCTCCCGCTCACCCAAACAGAAGACGTCGGCGCCGGAGCGGGCTCGGACATGGC

GAGGCTGCGAGCCGGCCCGAGCGGCGGGGCCCGGTGATCCCTCCCTCCCTCCCCGTCCCCTCCCCTCTCC

CGCACGCACGCCCCGTCCGCCCCCACCCCGCCCCCACCCCGGGCGAGCCCGCCCGCAGCCCGGGGCGCAC

ACCCGCACGCGCACTCCTCTCCACTCACTCCCGCGCCCGCCCCCACTCCCGCAGCCGAGCCCCGCCACGC

GCGCCTTGCCCGCCCGCCGGCCGCCCCCGCCGCCCCCGCCGCCCCCGGGCCCTGATGGACTGAATGAAGG

CTGCCTACACCGCCTATCGATGCCTCACCAAAGACCTAGAAGGCTGCGCCATGAACCCGGAGCTGACAAT

GGAAAGTCTGGGCACTTTGCACGGGCCGGCCGGCGGCGGCAGTGGCGGGGGCGGCGGCGGGGGCGGCGGG

GGCGGCGGCGGGGGCCCGGGCCATGAGCAGGAGCTGCTGGCCAGCCCCAGCCCCCACCACGCGGGCCGCG

GCGCCGCTGGCTCGCTGCGGGGCCCTCCGCCGCCTCCAACCGCGCACCAGGAGCTGGGCACGGCGGCAGC

GGCGGCAGCGGCGGCGTCGCGCTCGGCCATGGTCACCAGCATGGCCTCGATCCTGGACGGCGGCGACTAC

CGGCCCGAGCTCTCCATCCCGCTGCACCACGCCATGAGCATGTCCTGCGACTCGTCTCCGCCTGGCATGG

GCATGAGCAACACCTACACCACGCTGACACCGCTCCAGCCGCTGCCACCCATCTCCACCGTGTCTGACAA

GTTCCACCACCCTCACCCGCACCACCATCCGCACCACCACCACCACCACCACCACCAGCGCCTGTCCGGC

AACGTCAGCGGCAGCTTCACCCTCATGCGCGACGAGCGCGGGCTCCCGGCCATGAACAACCTCTACAGTC

CCTACAAGGAGATGCCCGGCATGAGCCAGAGCCTGTCCCCGCTGGCCGCCACGCCGCTGGGCAACGGGCT

AGGCGGCCTCCACAACGCGCAGCAGAGTCTGCCCAACTACGGTCCGCCGGGCCACGACAAAATGCTCAGC

CCCAACTTCGACGCGCACCACACTGCCATGCTGACCCGCGGTGAGCAACACCTGTCCCGCGGCCTGGGCA

CCCCACCTGCGGCCATGATGTCGCACCTGAACGGCCTGCACCACCCGGGCCACACTCAGTCTCACGGGCC

GGTGCTGGCACCCAGTCGCGAGCGGCCACCCTCGTCCTCATCGGGCTCGCAGGTGGCCACGTCGGGCCAG

CTGGAAGAAATCAACACCAAAGAGGTGGCCCAGCGCATCACAGCGGAGCTGAAGCGCTACAGTATCCCCC

-continued

AGGCGATCTTTGCGCAGAGGGTGCTGTGCCGGTCTCAGGGGACTCTCTCCGACCTGCTCCGGAATCCAAA
ACCGTGGAGTAAACTCAAATCTGGCAGGGAGACCTTCCGCAGGATGTGGAAGTGGCTTCAGGAGCCCGAG
TTCCAGCGCATGTCCGCCTTACGCCTGGCAGCGTGCAAACGCAAAGAGCAAGAACCAAACAAAGACAGGA
ACAATTCCCAGAAGAAGTCCCGCCTGGTGTTCACTGACCTCCAACGCCGAACACTCTTCGCCATCTTCAA
GGAGAACAAACGCCCGTCAAAGGAGATGCAGATCACCATTTCCCAGCAGCTGGGCCTGGAGCTCACAACC
GTCAGCAACTTCTTCATGAACGCCCGGCGCCGCAGCCTGGAGAAGTGGCAAGACGATCTGAGCACAGGGG
GCTCCTCGTCCACCTCCAGCACGTGTACCAAAGCATGATGGAAGGACTCTCACTTGGGCACAAGTCACCT
CCAAATGAGGACAACAGATACCAAAAGAAAACAAAGGAAAAAGACACCGGATTCCTAGCTGGGGCCCTTC
ACTGGTGATTTGAAAGCACAATTCTCTTGCAAAGAAACTTATATTCTAGCTGTAATCATAGGCCAGGTGT
TCTTCTTTTGTTTTTAATGGCTATGGAGTCCAAGTGCAAGCTGAAAAATTAATCTCTTAGAACCAGACAC
TGTTCTCTGAGCATGCTAAGCATCCCAGAAACCCAAATGGGGCCTTCCTGGAGCGAGTTAATTCCAGTAT
GGTGTCAACCAAGCTCGGGATTGCTTAAAATATCATCCATCCCACTTCAGGTCCTGTCAGCTTCTTGCAG
TCAGAGTTCCTATGAGTAACAATAGGAGTTTGGCCTATGTAAGGACTCTGAGTTTAGGCTTCCAAGATAC
AACAATAAGAGAAGAATCTAGCAACGAGAATGACCTCATTTGCTTTCCACATGCTTAGCCTCATTATACC
ATGTTATGTCCAAGTTCACAGCCACAACATCAGAATGGTAATTACTGAGCACAAGTTTTAAATATGGACG
TTAAAAAAAAAAATCCAAGGACCTGTTTTTCCAACCCAGACATCTTTTCATTGAATGATTTAGAAAGCTT
TAAGTTGATCCAGCTTACAATTTTTTTTTTCTTTACCTCCTGGAAATCTCATATGGTCTTGGATCCGTCA
AAAAAACCAGTCAGTTCACTTGCGCTCAAAGTATCAAGCACAACAAAGATAAACAGAAGTGAGGAAGGTT
CTGGGTTCACTACATCTGGATTTTCAAGACACCTATTGTGAAGTCATTAGGGAATTGATGAGAATATGGC
TTCAAGCACATTTTGCAGTTTGCTACAAATTCTGTTGTACATAATGCAGACGCACACTCAGGAGGCCAAT
TTAACTGTTAACAGTGCATGGAGCGAATGCAGCATTTTAAAAGATCTAGGTTTTTTTAGGTCATTAATGT
GTCCTTGGTTGATCAGTCATCTGGTCCCTCCTACTGTGTGTTATGACCACCACGTAATCCATTCTCGCTC
TTTCTGATTTGGGGTTTTTCCTCATCCATCCCATTAGTAGGGATGTTTTCTGTGTTTTCTAGCAAGAAAA
AAAAATCAATCAATCAAACCTGCATACATGTTACTCATGACTGTCATCTAGTCCTAAATCTCTTCTGTTG
TTGAATCATCCTTGCAAAACAGCTGAATACATCTGGAGAAAACACAGCACACCAAAGAAGCAGAATACTG
CAAACCAAAGACATTTATGACTTGTCATTTTCTAGCCTAAAAATACTGTGATTACTTTTAGAAATCAGAA
AACCTCTGCAACTCCGAATGGCATTCAGCTCTTGCATTTGGCGCATCATCGGGCTGAGCGGACCAGCTAC
ACCAAGGACATTAGCCAAGCCACCCAGAGGGGTGGCTTTGCCACACCAGTTGTCACCTTCCCATAGCAAG
TGGAAGAGCGCCCACAGAACTCTGGGAGATTGCAAAGGTCACAATGTGCATATTTACCAGTGAATGGCCC
CGGGTGGGGCCACGTGGGGGTGTTCAAAGCAAGCCAAACGCTGCAATCATTCTTTACAGACACTTGAGAC
TGACTTTTTTATGAATTACTTAGTCGAAACCAAAGAAACTTTTTCTGCACCTACTTCTGCAACAAACAAA
ACTGTCCCATTAAAATGAATAAATAAATCCGTAAATCAATGGAAATCACCACCAATAAGAAGGAAGCACG
CCAGAAAATAAACGAAAACAAAAACAGGGAGACACACTGTGTTCAAACAGACCTCTTGGGACATTTTTTG
GAAGCAGATTTTAAAGAAAGGGTTGAGACAAAGATAGAAATAAGGAAGAGCCTCAGTGGCTGCTGCTTCA
TTTGACAACTCACACGGTAATCTTAAAGCTGAAGATTGTCTTTAATTTGTGCCTATGCAGTTTTTCAAAA
GAACACGGAACAGAGCAACAGAAACCTCAACAGCTACAATACCAAAGATGAGGATTTCTCACACCTTTTG
TTTCAGTTCATTATCTCCTCTTGCCTGGCTAAAATACTAATAGCGCCATTGAACTGTATAAAGGTAATCA
ATTATGTTTCTCTGAGCAACAAAAGGAAAGGGCCATTTATTTGATTTTATTGTTTCATTTCAATTTTGTC
TTATGGTTTTTTGCCCCAACATGGAATCTCTCAAAAGTTTCCATGGACTCCAAGTTTAAGATGTTGGGAT
ATTGAACAGTTCTCTCTGCTCAGCAGAGGGTAGGGAATAACATTATCACTTGAATGTTCTTTGCTTAACC

-continued

CTTAGACTTGGTTCCTTCTATGTTCAGAGTCTCATCATCAGGGGAAGGAAAGGGAGTGAGGGTCAGGGAT

AGGGGTCTTGGTGATGCATCCTCTCCCGAGCCACAGAACCAAAGAGTTTATAGAGGAATTTACAGCCTCG

TTTTCATGTGATTGCTACATCCTAACAGGGCTTCATTTGGGGGTGGGGGGAAACATGTAAAAATAATTGC

CAGTTTCTACTTTTCTATTAGCTTTTTAAAAATCAGCTGTAAAGTTGCATTTCTAAAGAAAGATATATAT

AATATATAAAATACATATATAGATCAACTTGACATTGGTGATAACCAAAATTATTGCTGTCCAAATTCAT

GTCTTGTTTTGGTCCAGTGCTTCATTTGCTAAGTATTCGGTTCAGAATTTTTCTCATTTCTCATGCCATT

CCAGAGTTAATTTGCCACTGTGGATGATTTGAAGTATTCAGATCTCTATGGAAGTTTCTGGGACAGGTTT

AAAGTCAAGATCAAGCATTTTAGCATTTAACCTGTTGATAAATGGATCCATGGTGTACATGAGTTTTATT

TGTATTCGGAGTCATCTCTATTCTATCCCTCAGCCTCGATTAAGGTGGTGAGTGAAGTGCATCCAACAGA

CTCGGCCCAGAACTGGGTCCTGACAGTGGGGTGCTCATCTTCTGTAACTGTTGGGAAGGCTCGGTGGTCC

ATTTTCACCAGTTAAAGAATATGAGGCCAGCCCAGAAATCTGTTCTCCAGGAGCTGCCCTGTCCCATCTG

GGTGTGCCAGACCCCCTCAGTGAGCAGGTCCACCAAAGGGACTTCTCACAGGGGAAGCCCAACTCCTGTT

GCAATGGGTTGATAGATTTCCTCAGGGTGGTAATTACCAATTCGTATTTTGACAAGCCTATGTGCAACCA

CAGCTGGCACTGGGGTGGGCAGTGGTGTTGGGTGGGATGGGGGAGAGTGTCTCAATCCTGAAGAGAAAAT

ATAAAGCAGGTTTTGGGGAGACTTCTGGAGTCCTGCCCCTAGAGAGCCCCATTGTTGTTCTTTGTGCCCC

CTCCTCATTCCCCCTATGTGGGTCTCCCTATGCAGGAGCTGTGAGAGAATGTGACTCTCCACAATTTTTA

TAATTCATCCTTCCTAGGAGATTGTTCATTGGCTCTTCCCTTGTGTCCCTTTGTCCCTTGCTCATACTCC

ATGTTTCCTTTGTCAAAGGACTAAGAAAAGAGCATATTTCAGCAGAGGAGTGTTCCCATGTGGGTTGATT

TCAACTTGGGTATTTCTAAAAGAGTCCTTGTGACATGTGTCCAGTGGAAATGGTTGCTCTTTTCCAGACT

GGATTGAGGAATGGAGCCTGTTTGATTTGGTTAGTGATTCTTTGACATACTAATCTCAGCGTTTGGGTCT

CCAGCATCCTCTGAAGATGTCTAGACTAGTAGAGGCTGCCTTTGTGACCTGACATTACAACATTGGTCAA

ACCAGTCCTCTGATAATCAGAAGAACATGTCATAATTGTTTAAAAAAAAAAAAAAGGCAAGAATTTCTCT

CCAAGGAGCTTTAATAAATGTCTCATTCCAGATAATGTCATACCAGAGAAAAGTGCTTGCTTTTAGAAAA

TTATTTACATACATATATAAATATATATGTGTATCTATACAGTTATGTATCAAAATTTTAAGCCCTGCAG

AATTTCAATTTGTTAGAAATCTAACAGAAAAAAATTTCTATATTGAAAGGTAATAGAATTTAACCCAGTG

AGTTTACTCAAGGATTTTTAAATTTAAGTTAATAATTTCAGAGAAAATAACCATTTGGGTGTGGTTATAG

TTTAGTATCCATTACCTCAATCCAAGGAAAATTCCAGGCATTCCTCAACCATCAGGAAAAGGTACAGTGT

GAAGGAACAGTTCTCAGCCAAATTTCACATTCTTGAGGCAACAGAAATCAAAACACTCAGAGCCATTGAG

TGGAAAAACAATTTACTTTATTCCTTTACACAAATAGGCTTGCATTGTTTTTGTTTTAATGTGATTTTGG

TACTAGGGATATAATTATTTCATTCCAGGAAATAATAAAAAAAAACAGACAGAGCCAATACATTTCTTTT

TTTAAAGGAAACAGCAACAACAATAAAAACTCAGCACCAATATTTAAAAGCTTTTCCAAAATGTAAAAGA

AGTGTTTAGCTTGCACCATGCATAAAGGTGCAGGCTAGTTGAACCAGGAAGCATGGCACTTCCTCTGGAG

AAATCCAGAAAGAGTTGCTTCTAAGCTCCCTTTTCCCCCTGCAGGCTCTTGGCAATTGTAGGCTTTAGCA

AATCCAGAATAATTTTCAATTCAAGCTAAAATAAAATCAACATTTGGAATGTAAATCTGATACACACACA

CTTTTCTAAGTCAAACAACATATTTCAAAACCAAAAATAAATACCTTTTAGATAATCAGTTATTTTCTTT

GTCTATACTGGGCACCCACCTACTAGTGCCAGTAAATTCAAGTTGAACAGATTTTTAAAATCACTATTAT

CTGGGTATGGGGGAAACTTCCCCACTTTTGAAAATGTTGGTAGAATTATAGGAATGTCTGTTTGATTATC

ATTACCAAAGTGTCATGACAGTATGCCTTTGTAGTGAACTCGGATTTTCAGGAGTTTGAATAGTTGGATA

TTTTAAAATCTAAGAAGAAAAGGCCTGTTTCCAATGTTGTTGAAGAATAATGAACTCTATTAAAAAGTGG

AGAAAAAGATAATACATGTGGTCAAGGTTGACCACAAGGCCCAGGCACAACTACCTTGGCGATAATCTTC

TAGATTCGTAACAGGTTAGAGCTGACTTTTTGTTTTTGTTGTTGCTGATGCTGTGTGATTCAGACTTCTC

-continued

```
AGCCTAACCAGGAAGAGTAAGTGGAAATGGTAGATGAAGAAGGGGTAGAGCTGGTGTATCTATAACTTTC
TGATATTTGTCTGCCAAACTTGATATATTAGTAATTTTTTTATCTTTAGCTAAGATCAAGTCACCCCTGA
AACAACAGGAGATTCTAGTTTTAAAATAAGGCCACAAAAATCCTTACGGAATGAAGAATGGCACCCCAGT
TGGTTGTATAAGTCTCATAAGATAATGATGTTGATTTTAAATATGGATGTCTCAATGCCTGTTTTCTATC
AATGATTTGTTTGTTTCCAAGGTCGGGGAGGGAAAGAGGGGAGGGTTTATCTGTTTTAGAAAGTCTCAGA
ATACTTATAAAATACAGAAGTAGTTATTAAAATATATAGGACCTCACATAGGTAGATACAGAACTTACCA
TTGAGGCTGATGGGCTGTTGTGTGAATCACACAGGACCTTAAATGAGGCTCATTATTCTCACACACCAAA
ATGACTCTGACAGCCTGAAGCAGTTATTGCTAGAGCCCAAGCTTTCCTTGGAGGTTTTGGAGTTAGGTTG
ATTGGAAGTAACCAGCTAATACCTTTTCTAGTGGAGAAAAAGACATTGCTACCAGCTTGTTCATCCCATA
GAAGTCTTCCACTCTGCTCCATTTTTAGCAGCAAGCATTTCATGTAGCATAAACCTTGGCAGATAAGTGT
GCCTAAGGTTTATACAGTCTGTCCGCTTGGATGTATACAAATTTAGATACATATTTTAACATGTGTTCTC
ATAGATGACTTTATAACAACACACATTACCTATAGGTGTCTAGACTGTGTACATACAAGTGTGTACAGAC
AAGCTTCATACGTATATACTGTAATCCGTTACAACAAATAAATTTTAAATCATCGTTTAACATGTATGTG
GTACTTCTACAGTGTACATTGTTTTCATTATTTATTGTAACATTGAAAACCACAGTGCAGGGAAAACAAA
AGTATCCCAGCATCTTCATCCTGTACACTTGGAATTAATTTCATTTGGGCATATCCAAGATAAACTCAAC
TTTCAAGAAATCTTGTATATTATTTAATCATCTGTGTTAGGATGACACCTATGATTGATGACTTCGGTTG
AATAGCTTTATTCTGGATTTTTCATAACTAAAGCTAAATCCAAAGACCTGAAAAAGGACAAAAAGAAAAA
AAAAAAAAGAAAAAACAAAGAAAAAGAAGAAAAAAATAATAAAGTCAAGCGCAAACTGATGGGGAGACAGT
GGGCTCTGGTTTCCAGGATTGAGACAATGGTACTGCGGTCTTGGGGAGACTGCGTTAGCTAGTGGGGAGT
GGTGATTTTTTTCATGCTTGTCACATCTAAATGGTCTTTAACATGAGAAAGTTTTAGAGGTTATAATTTC
CTGCTTTGTTTTTATTTAGACTATCAAATGAAGTTATACATGTTGTCAGTCAAAAAATGAAGACACCCTC
TGCCCCACCCCACAGAATGCTTTTTATCTTGTCTCTTTGGGTTATGACCCAACAAGCTAAGTACCATTAA
TGTAATTAACTTATTTAAATTAGTTCCTAGTACATAAATGTATAGGATTTGGGTAATTATTTAATCATCC
TTCCTTAGTTTGATTCTACTCCTTGTACTTATTTATCAAAACCTAGACCAATGGTGCATCAGAGATGCAA
AATTCTACTTGGAATACTCTTGAAGTTTAGTTTGCTTTATAAAGCAGTGAAATTCTGTTACAGACAGGGA
AGAAATACAGGTTACAAAAAGAGAATTTGGGATATTCTTCCCTCTTAAATTAACTTTTAAAATAGTCTAA
GTAACAATTTTTAAATTATTTAACTTAAGTTCGCAGCCCCACCTGGTACCAGGCGAACTTCACCTCTTAA
TTATTGTGGCCCTCGGAGCCTTCATATTGTAACTTATTTATTTAACTTATTCAGCATCTGTGAAAGGTGC
ACTGTATAGTTTATATTTTTAATTTAAAACAACAGAGAGCACTGCAGTTTGTTTGCTGTCAGAACAACAG
AGCAAATTTTGTGGACAAGCAATGACTATTCAGCCTGAACCTGTGCATTCAGAAAACATAAGCTGAGACC
CTGCTTCACCAGCCTGGATTTCGGGGCTTCTATACAGAAACTGGAAAAATAAATTTTAAAAAAATCGTAA
ACAAAAAGAGAGAAACCCTTACACTAGCTGCTTCCAAGAATGAACTCTGTGTGTATGTAAAGCAACAAAA
CAAAAAAGGAAAAAAACAAAAAGCAGAAAAAAGAAAAAAAAAAATGAAAAACTTTCTATTTCTAGTGAGAA
CCAAAGAAGGCTACCTCACTGACTTTTTCCATTTGTAATTTTAATCGTGTTGATGACACCAAAGATACCA
AAGATTTCTTTCTCTGTGCGGTCTGCATTTTGCTTGTGCTCTTTTATAATTTGAACGATTTTCTCTGACA
TATGGTATGTACAGCCACAGCTCAGATACCCCAAAGAAATAATTATCTATGCGACGGCGGCTGCTAATTT
GGAAAGGGATATTTTCTGTGTTTCTCTTATATGTTTGCTGTCTGCTCGACATGTTCAAGATGCGAGTTCA
GATGCTGCTGTAATTGGATTCCTTAAATTCTGATTACAAATTGAGGAAGGAAACTGGTTGGAAATGGCCT
TCAGTCCTAGCCATGGCCTCTATCCCCGCTGGGACCTGTCACAGTAAAGACTGCCAATTACTGAACCACA
GAAGCTCTGACCATTGAGTAGTTGAGCTGGAAGAGACCTTAGGAATCATTTAGTCCAAGCCCCGGTGGCC
```

-continued

CAGAGGAATGAAATAGTTATCCAAATCAAATAACTCTTGAGAGTGAAAGCCCACACATGCCTCCTGGTTC

CTGCCCCAGTGCTCCGCTTATTGTACAGTGCTACCTCTGCATGAGAGCGGTCCCACATTGACAAATAGGA

TGGTGGCAATCCTTTAGCAATGAGCAGGGACTGGGGTTTATCTCTTAACATTTTCAGCTGTAAAATTAGT

CACAAGCATTTTCAGTGTCCCATTAGTACATAGTCACATATGGTCGGTTGCTTCGTGAAGGTGGCCTGTC

TTGAAATACTAGGGCTCATACGGGATTTTTGCCCTAGGAAAAACATGTTGATCCCAATGATGTGATCACT

TTTGAACCTTTCCATTACAAAGCATTGTATAGATAACTTTTTAATTCAGTAGGAGGAGAAAGTTCATTCT

TGGCCTGTTGGCTTTGATTATTATGGGTACTTTAAAGTCAGTATTTATCAAGAAAGGGAACTTGACCACC

ATTGGCACATGTGACATTTAAGCTCTTCAGCCTTTTCCTTTTTAGTTGTAGGTGTTTACATTTCATTTCT

AAGCCAACTCTGTATTTATGAGAGAAGTTTAAGCCTTACATCATTTGATACTAAAGGGTTATTTGTGGTA

AATGAAAAATGACCCCAAAATTACAGAGGAATATGCCAGTTTAAGAAATGGCTACTTAAAGTTGCTTCTC

TCTTTCCTTCTTACTCATGAAATTAATTGGTCTTCTTCAAGTTTCTTTAGATTCCATTAAATGATTAAAT

CACTATTAAGAGCCATTCATCAACGTGATTTGTGTGTTAGCCAATGAATCTGTCTCAGCTTTTGACCAAA

TGGGTTTTAGACAAATGCAAAGATCTGCCTCTAGTCCATATGGCTCTTTTTGAGTGCTAGTATTTTGCAT

TTCACATAATGTAGTTATTTTGAGCTTTTAAAGAGAGCATTTAGACAAAGAAGCAAAGAGAGGAAGGGAC

CAATCAACTCATCAGTTCCATGCATCAACAAAGCATAGCTAGTAGAGGAATATAAATGACAGATTGACAA

ACTGTAGGAAACACTGTTACTCTCTTTCTGAAGTTTTCAAGCACCATCCTATGTGAAAGTTCCCTCCTGT

CCAAACAAGCTCAAGGCCCATCTTCTCCCTATACAAGGCAAACCTGTAAGGCCTTCCTTCCAAAGAGTAC

ATTGCTTTGGTTTTCTTCCTAAATTCCTATTGGAATTAGAACTCTCAGAATCCCTGGGAGACAGAGCAAA

GATGACTTAATTCATTGAGCAGCAGAGCTCCCTATAAGTGAACATCACCTTCCCCATCTTTCCTACTGCC

ACACCCATACGAGAGAGGATCTAGAAAGAGCGATGGCAGCCTGAACACAGAAAACATCCCCACTTGGCAG

ACCTCTCCTCAGCAATCCCCCCAGCCTCATGCTTCACTTGCAAAGTGTGACATAACCACGGGACGAGTGC

CTTGCTTGAACCAAAGCAACGATTTAGCCAGTCTGGACCTCTCTGTGCTTTTTTTAATTCTTCCTGTGAA

TACCTCAGCTTCAACTGGGCCTCCATACAGTCAGTTGGTGGGCTTATTGTACTGTGGTGCTTTGCAATGC

AACCCTGCAAAGAACAAGATTTGTACTAATACCAAAGGTTCTTTCTCTATGTCTCCTCCTCTGCCTCCCT

CGTTCTTCCCTTTTTTCTAGTTCTTCACGGTTCCAAAGCTTTACTATGAACCTGGGCATGTTGGCAATGC

AGACCGCGCAATTCCTTACCGAATTTTCTCAGATATACCTCATAGACAATAGTGTTTAGAGTAATGTTAT

TATAGCGTATGTAATAAATTATTCACTGTTTCTTTTGGTAACTGTGATTTAAAAAAAGAAAAAAGAAAAA

AAAGCTTTATACGTTTTAGGTTGTGCTTTTGTAATAGATGAAAAAAGGTGCGCTTAAAAAGAAAATGTAT

GTTTTTTTCCCCCTTTGGATTTTATTTATGCTGGATTGGGGAAAGTTGCAGAATGAGCCCAAAGTTTACA

GTTTCATATTTTGCTGAAGAAACAATCTGTGTTCATTTGCTCTGTTGAAAAGAATAATTATTTTCTACAT

TTGTGCCACTTGGTCTGAACAATTAATTGTTCCGTGTTAACAGTGTAGTATTATGATTAGCAACTGCCAA

TCAGTGCTATAATTTTATGCATGAGGCTAAAAATTTAGCAGTGTGATGCATTGTGGTCTTAATAGCAACA

TTTTTCATTTTGAACTAGATCTTCCCCTTTGGTTCAATGGACTTTATTTATGCATGGGCGCCTATTGTTT

GTTAGCAGTTGTGGAACAGTTGTGTATACATTAAACTGTGAAAATGTACACAGTTCAGCCTCAGACGGTG

GTAATATTGGTTTTATTGGGAGATGTGTCACCTCGAAAATACCCTTTACATCTGTTGGGATCTGAAAATG

AGTCACATTGAATTGGGTTCCAGCTTTATAATGAGAAACGTTATTCCTAATTTTTGAGTTAGCCAATTTG

CATTCCACAAATTGGGATCCTCATAACCCAAATATATCACCGTATGTGAGAGGGATTTGAAAGCGAGTAT

TGAAAAACTCACCTTTGCATATTTAATTTCCACCAAAAGGAGTTATTTTGGCTTTATGCTCATGAACTTA

GACCTAACTGGCCATGTATATGTAGATGCAAATTCATCTAGCTGTGGCCCCTCTTTGATCTCTGCTTGGGA

ATGGCTATTTTTGACTATGCGTGGTTTCTTCTCGTATTTTGTGATCAGGTCAGCTCCCAGTAGAAACTCA

AATGGCATCAATATTACTAACTCTTCTCTGCCCACTTCTCTTTTGTCCACTCTCCTAGACATTCCCACCA

-continued

ACTGTTCCAGTGATTTGGGCAAAAATACGCAGCCATTTCCCAAAACTTCACATGTGCAGCTATCATGGCT

GTCCCTCCCTAGACTTGGAGGTGACTCTCACTTAATTTTTACCTGCCCAACAATGTTCCATCTACCATCT

AAAAGGTAATATAAGAAGAAGTTTTGAAACCCACTTTAGGAAAACCATCTTCTTTAAATCCTTCAATTAT

CTGAGGCCTCTATATGTCAAAACTATTTTTCAGTTGCAGGGGATTGGGCAAACTTGTTCTTTCTTATACT

TGGGTTCAAAGACCCATTCTCCAGTTTCATATTTCCCAAACCAAAATGCTTGACATAAAGCCAAATCAAC

TGCCAAGCACACTTTATTTTGCATAGGAGTATGCAGCCTAGGGAACCTTGGTTGAAAAGCAGCAGTCTGC

TATGCAAAATATTGGAAATCACTGACAGTGTAGCATTCATATTATCTGTCAATGAGGGTATATTGGGAAC

GTGCTCTCGTGAATAATAAAAAGCAACATATTTTTATTTGGCCTTATAAATTAGGTTGTGGTAATGTAAA

CTTTGATATATAGTCTTTTTATTTTTCTCTTATTAATCTGCCAAAGATGGGAACAGATACAAGAATTTTT

CAAATTGGCTTTTGTAAGACAATTGATGATTGTAATAGTGTTTAATCTTCCAGAAAGCTTTATATGTTGT

TCCACAATAAAATTGATATTTGTTTCAGCAAAGTTTTCCTGACACTCACAAACCCACAAACTGTTCCTCT

TAATGCAGATATTGTAGAATCTACAAAGTTCAAATCCATTTTTGATCCAAAGAAAGTAGAGGAGTATTTG

AGACATGAGTGTACCCAGCCCTTTTTTTAATCACAGGCAATGCATGGGTCTGGCTGGTTACACTTTGCCA

AGAAGACTTGTCTTATGAAACCCAAGGTATATTTTGTTATGCCATTTTATGTCCTTTTCTTTTAACATTG

TGGAAAGTGGTATGTTGAATCAAGTGTAAGCTGAGTTTTCCAGACAACTGAAGTAGCTACATCATGAATG

TTATTTTGTTATTAAAGGGTTTTTACTCAGTGCTTTGTGCCAATGGATGTCCTTTTCCTTGGAGACACAT

AACTACAAAATTACCTCAGCTTGGCCTGGTTTTCTCTCCTGCCCTCTTGGGGAAACATGGGCCTGGCCTG

GGAAAAGGCAGGTCATGGGCTGGAAGGTAGGTTTTGGTACTAGGAAGAAATCTCTGTATCTGTCAGCTTT

AAAGAGAACTGGGCCAAAAATCTCTAACCTCACTCTCTCTGGACTCCAACACTTCCCTGCAATCCTTTGG

TCTTGAGCATGTGCCAGCATGAAGGCAGACTCCAGTTCATACATGAAAGGCAAGAAAAAGAAAATAGTAA

CCTTGAATCTTCTGTGGGCCACCAGGCACTCACCTTTCCCCACCTTGCACACTATCCAGTCAAGGCTATT

GCAGCCCATCTGGTGGCTTTACATGGGACATTACCAAAGGCTTCTTCCTCCATCCTGGGGTTGCAAAGGA

TCCAGGTCCCCTCCATCCAGTGGGGCTCTTCCACATCAGAAGTCCCCCTCCCACCATCCTCTGCATCCTG

TTTAGCTATCCCATCTATACCTTTTGGAGATGATTATTTAGAAAACAAAGAAAGGTATGGAATGGGGTTT

CCTATTGTTTGCTAGGTTATATTTTAGCAATTCTCAATTCTTTGATCTGGAAAAATACAAGAGGGAAAAG

GAGACCCCACTATCTCCCTGTGCTTTGCTCCCATCTCAGGGGGCAGGGGCAGTGCACATTGCCTATGCTG

TTGATCTGTCTTGGGCGACAGGCTGAATCACAGCTATTGCCCCAGCCAAAAACATGGCCCATCAATGCCT

ACTTTATCTCTGCTTGAAAATCCTATTCAAAAAGTTGTAGAGTTTGAGGTTTTTATCCCCCCATATCCTT

TGCTTTGGTCCAGTTTGGCCTTTAGCATAAGAGTCAGCTTTATCTCTAGGAAAGTTTTTTCAGATTATGA

CAAGGAACCTGCCACCTGGGAAGAAAAGAGTCCGAAGACTAGCAATCGGATAGGTAGTCATACCATTAAC

AGATACTTCCTTGAAGGTAGAATATTATTTCCTTTCTTTACAGTTTTGTGTTACACAAGTCCAAGTGGTG

CCAGCAAACTTCTTACCGTGAAATGTTGTAAAACACCTGGCATACTGAAATTTCTGAAACAAAAACACAA

GCTCCACATTGATAACTTGATAAATAACCACTAAAGTTTAGATGCAGGGACTGAGATGATACAGGCAAAA

TCTTGGTGTTGGTTTCTCTTTTAATTCGTATCTTCGATCACCTAACCTTTCTCAATCCAAGAGCAGTTCA

GTCTTTTCTCCCCAAGTCTAGGATGCCAAAGAGCATCATAGGAAAAGATAATTAGGGATTGACCAGCATT

TCAATTAGTTCTCTTCTTCATCTTTGCATTTCTCAAAAGTGTTCTCCTGGACCAGAGGGAAAGAGCTGGT

CCATTTTTTTTCATTCTTTCTATTCAAATTTTTCCACCCAGACAATACTTTATTAACACAGATACTGTAG

ATCCTTCCTTGGTCAGTGAATTATTACAAGAGGAGCTATCCTTCCACCAAAGTGAGTGAAAACAAGTTCC

AGTATCTTTTCTTCCATCCAGTTTTGTTCTCAGAATCCAAGTCAGTCCTGGGTCTTTTCTCACTTTAGAC

CCTGGCCTCAGATGTGTTTATTCTTGCTATTTAAAAATACCTTTAAATTTCACATGCTGGCCTGCAGAAC

-continued

TTGCATCCTTTGTTCTATACTGTTGACTGCTTGATGGTATTGAAAGGTGACTATAATGAGGGAAGAAAGG

AGGAGGTAAAGAGAGAAGAATTTGTCCCAGATCTGTTTAAAGTTTCAAAATTTAAAAAGGGACCCATTAA

ATTATGGGAAAATGGCTATAGAGTGTGAGCCTCCGTTGACCATATGCTCAAAGACCGTACTCTGCCACCT

GCCTTCCAGGTAGCTATTCTAGAAACTCAGTCCTTTGTGGAAACCCAACTACCTTTTAAAAGTCTCTTTC

CAGATTCCAAAAGGACAAGAGATCAGAGAGTCACATATACGCCTCTTGTTTTATTTTCTTGCTTTCACGG

GTATTATTGCCAAGAAAATCGTAGGGAAAAACTTTAAACTTTTCTTTTCAGTTGATCCCTTTGACATCAC

CTCTCATGTTTAAAATCAGGAAAACACACCCCTAAAATTTGCACTCTCTTCCGTTTTGAAAAAGAAAACC

CACACACAAATGCACACTATTACCGTCTTTCACCCTGCGCTATATTTCCAAAGTGTATTATAATCCAGAT

ATTGCCCCATCTCAAACATGTTAAGTCAGACTGTGCTGAAAGACTTTCCAGGGACGGTCAACAGGGTATA

TGTTCAGTGGCTGCCCTGAAATCCTGGTGGGGATGAGGATCACGCTTCATCATCAAGGGGATGCCCATCC

CCTGATAAGCTCCCAGTCCTTTTGGAAGATTTCTTTGAATGTTAATTGCATTTTCAGTTTTGCTCATTTC

CCACCCCAATGTTTTGTCTGCAACATCGCTTACACTGGATTCTTTCTATTTTTATTCCTATCATTAAATG

GTAGTGCTGTAAATTCTGCAATTAATGTTAAATAAACTGCTTTAATTCATTGA

NM_002467.6 *Homo sapiens* MYC proto-oncogene, bHLH transcription factor (MYC), transcript variant 1, mRNA (SEQ ID NO: 17)

AACTCGCTGTAGTAATTCCAGCGAGAGGCAGAGGGAGCGAGCGGGCGGCCGGCTAGGGTGGAAGAGCCGG

GCGAGCAGAGCTGCGCTGCGGGCGTCCTGGGAAGGGAGATCCGGAGCGAATAGGGGGCTTCGCCTCTGGC

CCAGCCCTCCCGCTGATCCCCCAGCCAGCGGTCCGCAACCCTTGCCGCATCCACGAAACTTTGCCCATAG

CAGCGGGCGGGCACTTTGCACTGGAACTTACAACACCCGAGCAAGGACGCGACTCTCCCGACGCGGGGAG

GCTATTCTGCCCATTTGGGGACACTTCCCCGCCGCTGCCAGGACCCGCTTCTCTGAAAGGCTCTCCTTGC

AGCTGCTTAGACGCTGGATTTTTTTCGGGTAGTGGAAAACCAGCAGCCTCCCGCGACGATGCCCCTCAAC

GTTAGCTTCACCAACAGGAACTATGACCTCGACTACGACTCGGTGCAGCCGTATTTCTACTGCGACGAGG

AGGAGAACTTCTACCAGCAGCAGCAGCAGAGCGAGCTGCAGCCCCCGGCGCCCAGCGAGGATATCTGGAA

GAAATTCGAGCTGCTGCCCACCCCGCCCCTGTCCCCTAGCCGCCGCTCCGGGCTCTGCTCGCCCTCCTAC

GTTGCGGTCACACCCTTCTCCCTTCGGGGAGACAACGACGGCGGTGGCGGGAGCTTCTCCACGGCCGACC

AGCTGGAGATGGTGACCGAGCTGCTGGGAGGAGACATGGTGAACCAGAGTTTCATCTGCGACCCGGACGA

CGAGACCTTCATCAAAAACATCATCATCCAGGACTGTATGTGGAGCGGCTTCTCGGCCGCCGCCAAGCTC

GTCTCAGAGAAGCTGGCCTCCTACCAGGCTGCGCGCAAAGACAGCGGCAGCCCGAACCCCGCCCGCGGCC

ACAGCGTCTGCTCCACCTCCAGCTTGTACCTGCAGGATCTGAGCGCCGCCGCCTCAGAGTGCATCGACCC

CTCGGTGGTCTTCCCCTACCCTCTCAACGACAGCAGCTCGCCCAAGTCCTGCGCCTCGCAAGACTCCAGC

GCCTTCTCTCCGTCCTCGGATTCTCTGCTCTCCTCGACGGAGTCCTCCCCGCAGGGCAGCCCCGAGCCCC

TGGTGCTCCATGAGGAGACACCGCCCACCACCAGCAGCGACTCTGAGGAGGAACAAGAAGATGAGGAAGA

AATCGATGTTGTTTCTGTGGAAAAGAGGCAGGCTCCTGGCAAAAGGTCAGAGTCTGGATCACCTTCTGCT

GGAGGCCACAGCAAACCTCCTCACAGCCCACTGGTCCTCAAGAGGTGCCACGTCTCCACACATCAGCACA

ACTACGCAGCGCCTCCCTCCACTCGGAAGGACTATCCTGCTGCCAAGAGGGTCAAGTTGGACAGTGTCAG

AGTCCTGAGACAGATCAGCAACAACCGAAAATGCACCAGCCCCAGGTCCTCGGACACCGAGGAGAATGTC

AAGAGGCGAACACACAACGTCTTGGAGCGCCAGAGGAGGAACGAGCTAAAACGGAGCTTTTTTGCCCTGC

GTGACCAGATCCCGGAGTTGGAAAACAATGAAAAGGCCCCCAAGGTAGTTATCCTTAAAAAAGCCACAGC

ATACATCCTGTCCGTCCAAGCAGAGGAGCAAAAGCTCATTTCTGAAGAGGACTTGTTGCGGAAACGACGA

GAACAGTTGAAACACAAACTTGAACAGCTACGGAACTCTTGTGCGTAAGGAAAAGTAAGGAAAACGATTC

CTTCTAACAGAAATGTCCTGAGCAATCACCTATGAACTTGTTTCAAATGCATGATCAAATGCAACCTCAC

-continued

AACCTTGGCTGAGTCTTGAGACTGAAAGATTTAGCCATAATGTAAACTGCCTCAAATTGGACTTTGGGCA

TAAAAGAACTTTTTTATGCTTACCATCTTTTTTTTTTCTTTAACAGATTTGTATTTAAGAATTGTTTTTA

AAAAATTTTAAGATTTACACAATGTTTCTCTGTAAATATTGCCATTAAATGTAAATAACTTTAATAAAAC

GTTTATAGCAGTTACACAGAATTTCAATCCTAGTATATAGTACCTAGTATTATAGGTACTATAAACCCTA

ATTTTTTTTATTTAAGTACATTTTGCTTTTTAAAGTTGATTTTTTTCTATTGTTTTTAGAAAAAAATAAAA

TAACTGGCAAATATATCATTGAGCCAAATCTTAAGTTGTGAATGTTTTGTTTCGTTTCTTCCCCCTCCCA

ACCACCACCATCCCTGTTTGTTTTCATCAATTGCCCCTTCAGAGGGTGGTCTTAAGAAAGGCAAGAGTTT

TCCTCTGTTGAAATGGGTCTGGGGGCCTTAAGGTCTTTAAGTTCTTGGAGGTTCTAAGATGCTTCCTGGA

GACTATGATAACAGCCAGAGTTGACAGTTAGAAGGAATGGCAGAAGGCAGGTGAGAAGGTGAGAGGTAGG

CAAAGGAGATACAAGAGGTCAAAGGTAGCAGTTAAGTACACAAAGAGGCATAAGGACTGGGGAGTTGGGA

GGAAGGTGAGGAAGAAACTCCTGTTACTTTAGTTAACCAGTGCCAGTCCCCTGCTCACTCCAAACCCAGG

AATTCTGCCCAGTTGATGGGGACACGGTGGGAACCAGCTTCTGCTGCCTTCACAACCAGGCGCCAGTCCT

GTCCATGGGTTATCTCGCAAACCCCAGAGGATCTCTGGGAGGAATGCTACTATTAACCCTATTTCACAAA

CAAGGAAATAGAAGAGCTCAAAGAGGTTATGTAACTTATCTGTAGCCACGCAGATAATACAAAGCAGCAA

TCTGGACCCATTCTGTTCAAAACACTTAACCCTTCGCTATCATGCCTTGGTTCATCTGGGTCTAATGTGC

TGAGATCAAGAAGGTTTAGGACCTAATGGACAGACTCAAGTCATAACAATGCTAAGCTCTATTTGTGTCC

CAAGCACTCCTAAGCATTTTATCCCTAACTCTACATCAACCCCATGAAGGAGATACTGTTGATTTCCCCA

TATTAGAAGTAGAGAGGGAAGCTGAGGCACACAAAGACTCATCCACATGCCCAAGATTCACTGATAGGGA

AAAGTGGAAGCGAGATTTGAACCCAGGCTGTTTACTCCTAACCTGTCCAAGCCACCTCTCAGACGACGGT

AGGAATCAGCTGGCTGCTTGTGAGTACAGGAGTTACAGTCCAGTGGGTTATGTTTTTTAAGTCTCAACAT

CTAAGCCTGGTCAGGCATCAGTTCCCCTTTTTTTGTGATTTATTTTGTTTTTATTTTGTTGTTCATTGTT

TAATTTTTCCTTTTACAATGAGAAGGTCACCATCTTGACTCCTACCTTAGCCATTTGTTGAATCAGACTC

ATGACGGCTCCTGGGAAGAAGCCAGTTCAGATCATAAAATAAAACATATTTATTCTTTGTCATGGGAGTC

ATTATTTTAGAAACTACAAACTCTCCTTGCTTCCATCCTTTTTTACATACTCATGACACATGCTCATCCT

GAGTCCTTGAAAAGGTATTTTTGAACATGTGTATTAATTATAAGCCTCTGAAAACCTATGGCCCAAACCA

GAAATGATGTTGATTATATAGGTAAATGAAGGATGCTATTGCTGTTCTAATTACCTCATTGTCTCAGTCT

CAAAGTAGGTCTTCAGCTCCCTGTACTTTGGGATTTTAATCTACCACCACCCATAAATCAATAAATAATT

ACTTTCTTTGA

NM_006509.4 *Homo sapiens* RELB proto-oncogene, NF-kB subunit (RELB), mRNA (SEQ ID NO: 18)

GCAGCCCCGGGCGCCGCGCGTCCTGCCCGGCCTGCGGCCCCAGCCCTTGCGCCGCTCGTCCGACCCGCGA

TCGTCCACCAGACCGTGCCTCCCGGCCGCCCGGCCGGCCCGCGTGCATGCTTCGGTCTGGGCCAGCCTCT

GGGCCGTCCGTCCCCACTGGCCGGGCCATGCCGAGTCGCCGCGTCGCCAGACCGCCGGCTGCGCCGGAGC

TGGGGGCCTTAGGGTCCCCCGACCTCTCCTCACTCTCGCTCGCCGTTTCCAGGAGCACAGATGAATTGGA

GATCATCGACGAGTACATCAAGGAGAACGGCTTCGGCCTGGACGGGGGACAGCCGGGCCCGGGCGAGGGG

CTGCCACGCCTGGTGTCTCGCGGGGCTGCGTCCCTGAGCACGGTCACCCTGGGCCCTGTGGCGCCCCCAG

CCACGCCGCCGCCTTGGGGCTGCCCCCTGGGCCGACTAGTGTCCCCAGCGCCGGGCCCGGGCCCGCAGCC

GCACCTGGTCATCACGGAGCAGCCCAAGCAGCGCGGCATGCGCTTCCGCTACGAGTGCGAGGGCCGCTCG

GCCGGCAGCATCCTTGGGGAGAGCAGCACCGAGGCCAGCAAGACGCTGCCCGCCATCGAGCTCCGGGATT

GTGGAGGGCTGCGGGAGGTGGAGGTGACTGCCTGCCTGGTGTGGAAGGACTGGCCTCACCGAGTCCACCC

CCACAGCCTCGTGGGGAAAGACTGCACCGACGGCATCTGCAGGGTGCGGCTCCGGCCTCACGTCAGCCCC

-continued

CGGCACAGTTTTAACAACCTGGGCATCCAGTGTGTGAGGAAGAAGGAGATTGAGGCTGCCATTGAGCGGA

AGATTCAACTGGGCATTGACCCCTACAACGCTGGGTCCCTGAAGAACCATCAGGAAGTAGACATGAATGT

GGTGAGGATCTGCTTCCAGGCCTCATATCGGGACCAGCAGGGACAGATGCGCCGGATGGATCCTGTGCTT

TCCGAGCCCGTCTATGACAAGAAATCCACAAACACATCAGAGCTGCGGATTTGCCGAATTAACAAGGAAA

GCGGGCCGTGCACCGGTGGCGAGGAGCTCTACTTGCTCTGCGACAAGGTGCAGAAAGAGGACATATCAGT

GGTGTTCAGCAGGGCCTCCTGGGAAGGTCGGGCTGACTTCTCCCAGGCCGACGTGCACCGCCAGATTGCC

ATTGTGTTCAAGACGCCGCCCTACGAGGACCTGGAGATTGTCGAGCCCGTGACAGTCAACGTCTTCCTGC

AGCGGCTCACCGATGGGGTCTGCAGCGAGCCATTGCCTTTCACGTACCTGCCTCGCGACCATGACAGCTA

CGGCGTGGACAAGAAGCGGAAACGGGGGATGCCCGACGTCCTTGGGGAGCTGAACAGCTCTGACCCCCAT

GGCATCGAGAGCAAACGGCGGAAGAAAAAGCCGGCCATCCTGGACCACTTCCTGCCCAACCACGGCTCAG

GCCCGTTCCTCCCGCCGTCAGCCCTGCTGCCAGACCCTGACTTCTTCTCTGGCACCGTGTCCCTGCCCGG

CCTGGAGCCCCCTGGCGGGCCTGACCTCCTGGACGATGGCTTTGCCTACGACCCTACGGCCCCCACACTC

TTCACCATGCTGGACCTGCTGCCCCCGGCACCGCCACACGCTAGCGCTGTTGTGTGCAGCGGAGGTGCCG

GGGCCGTGGTTGGGGAGACCCCCGGCCCTGAACCACTGACACTGGACTCGTACCAGGCCCCGGGCCCCGG

GGATGGAGGCACCGCCAGCCTTGTGGGCAGCAACATGTTCCCCAATCATTACCGCGAGGCGGCCTTTGGG

GGCGGCCTCCTATCCCCGGGGCCTGAAGCCACGTAGCCCCGCGATGCCAGAGGAGGGGCACTGGGTGGGG

AGGGAGGTGGAGGAGCCGTGCAATCCCAACCAGGATGTCTAGCACCCCCATCCCCTTGGCCCTTCCTCAT

GCTTCTGAAGTGGACATATTCAGCCTTGGCGAGAAGCTCCGTTGCACGGGTTTCCCCTTGAGCCCATTTT

ACAGATGAGGAAACTGAGTCCGGAGAGGAAAAGGGACATGGCTCCCGTGCACTAGCTTGTTACAGCTGCC

TCTGTCCCCACATGTGGGGGCACCTTCTCCAGTAGGATTCGGAAAAGATTGTACATATGGGAGGAGGGGG

CAGATTCCTGGCCCTCCCTCCCCAGACTTGAAGGTGGGGGGTAGGTTGGTTGTTCAGAGTCTTCCCAATA

AAGATGAGTTTTTGAGCC

NM_002309.5 *Homo sapiens* LIF interleukin 6 family cytokine (LIF), transcript variant 1, mRNA (SEQ ID NO: 19)

ATGAACCTCTGAAAACTGCCGGCATCTGAGGTTTCCTCCAAGGCCCTCTGAAGTGCAGCCCATAATGAAG

GTCTTGGCGGCAGGAGTTGTGCCCCTGCTGTTGGTTCTGCACTGGAAACATGGGGCGGGGAGCCCCCTCC

CCATCACCCCTGTCAACGCCACCTGTGCCATACGCCACCCATGTCACAACAACCTCATGAACCAGATCAG

GAGCCAACTGGCACAGCTCAATGGCAGTGCCAATGCCCTCTTTATTCTCTATTACACAGCCCAGGGGGAG

CCGTTCCCCAACAACCTGGACAAGCTATGTGGCCCCAACGTGACGGACTTCCCGCCCTTCCACGCCAACG

GCACGGAGAAGGCCAAGCTGGTGGAGCTGTACCGCATAGTCGTGTACCTTGGCACCTCCCTGGGCAACAT

CACCCGGGACCAGAAGATCCTCAACCCCAGTGCCCTCAGCCTCCACAGCAAGCTCAACGCCACCGCCGAC

ATCCTGCGAGGCCTCCTTAGCAACGTGCTGTGCCGCCTGTGCAGCAAGTACCACGTGGGCCATGTGGACG

TGACCTACGGCCCTGACACCTCGGGTAAGGATGTCTTCCAGAAGAAGAAGCTGGGCTGTCAACTCCTGGG

GAAGTATAAGCAGATCATCGCCGTGTTGGCCCAGGCCTTCTAGCAGGAGGTCTTGAAGTGTGCTGTGAAC

CGAGGGATCTCAGGAGTTGGGTCCAGATGTGGGGGCCTGTCCAAGGGTGGCTGGGGCCCAGGGCATCGCT

AAACCCAAATGGGGGCTGCTGGCAGACCCCGAGGGTGCCTGGCCAGTCCACTCCACTCTGGGCTGGGCTG

TGATGAAGCTGAGCAGAGTGGAAACTTCCATAGGGAGGGAGCTAGAAGAAGGTGCCCCTTCCTCTGGGAG

ATTGTGGACTGGGGAGCGTGGGCTGGACTTCTGCCTCTACTTGTCCCTTTGGCCCCTTGCTCACTTTGTG

CAGTGAACAAACTACACAAGTCATCTACAAGAGCCCTGACCACAGGGTGAGACAGCAGGGCCCAGGGGAG

TGGACCAGCCCCCAGCAAATTATCACCATCTGTGCCTTTGCTGCCCCTTAGGTTGGGACTTAGGTGGGCC

AGAGGGGCTAGGATCCCAAAGGACTCCTTGTCCCCTAGAAGTTTGATGAGTGGAAGATAGAGAGGGGCCT

-continued

CTGGGATGGAAGGCTGTCTTCTTTTGAGGATGATCAGAGAACTTGGGCATAGGAACAATCTGGCAGAAGT

TTCCAGAAGGAGGTCACTTGGCATTCAGGCTCTTGGGGAGGCAGAGAAGCCACCTTCAGGCCTGGGAAGG

AAGACACTGGGAGGAGGAGAGGCCTGGAAAGCTTTGGTAGGTTCTTCGTTCTCTTCCCCGTGATCTTCCC

TGCAGCCTGGGATGGCCAGGGTCTGATGGCTGGACCTGCAGCAGGGGTTTGTGGAGGTGGGTAGGGCAGG

GGCAGGTTGCTAAGTCAGGTGCAGAGGTTCTGAGGGACCCAGGCTCTTCCTCTGGGTAAAGGTCTGTAAG

AAGGGGCTGGGGTAGCTCAGAGTAGCAGCTCACATCTGAGGCCCTGGGAGGCCTTGTGAGGTCACACAGA

GGTACTTGAGGGGGACTGGAGGCCGTCTCTGGTCCCCAGGGCAAGGGAACAGCAGAACTTAGGGTCAGGG

TCTCAGGGAACCCTGAGCTCCAAGCGTGCTGTGCGTCTGACCTGGCATGATTTCTATTTATTATGATATC

CTATTTATATTAACTTATTGGTGCTTTCAGTGGCCAAGTTAATTCCCCTTTCCCTGGTCCCTACTCAACA

AAATATGATGATGGCTCCCGACACAAGCGCCAGGGCCAGGGCTTAGCAGGGCCTGGTCTGGAAGTCGACA

ATGTTACAAGTGGAATAAGCCTTACGGGTGAAGCTCAGAGAAGGGTCGGATCTGAGAGAATGGGGAGGCC

TGAGTGGGAGTGGGGGGCCTTGCTCCACCCCCCCCCCATCCCCTACTGTGACTTGCTTTAGGGTGTCAGGG

TCCAGGCTGCAGGGGCTGGGCCAATTTGTGGAGAGGCCGGGTGCCTTTCTGTCTTGATTCCAGGGGGCTG

GTTCACACTGTTCTTGGGCGCCCCAGCATTGTGTTGTGAGGCGCACTGTTCCTGGCAGATATTGTGCCCC

CTGGAGCAGTGGGCAAGACAGTCCTTGTGGCCCACCCTGTCCTTGTTTCTGTGTCCCCATGCTGCCTCTG

AAATAGCGCCCTGGAACAACCCTGCCCCTGCACCCAGCATGCTCCGACACAGCAGGGAAGCTCCTCCTGT

GGCCCGGACACCCATAGACGGTGCGGGGGGCCTGGCTGGGCCAGACCCCAGGAAGGTGGGGTAGACTGGG

GGGATCAGCTGCCCATTGCTCCCAAGAGGAGGAGAGGGAGGCTGCAGATGCCTGGGACTCAGACCAGGAA

GCTGTGGGCCCTCCTGCTCCACCCCCATCCCACTCCCACCCATGTCTGGGCTCCCAGGCAGGGAACCCGA

TCTCTTCCTTTGTGCTGGGGCCAGGCGAGTGGAGAAACGCCCTCCAGTCTGAGAGCAGGGGAGGGAAGGA

GGCAGCAGAGTTGGGGCAGCTGCTCAGAGCAGTGTTCTGGCTTCTTCTCAAACCCTGAGCGGGCTGCCGG

CCTCCAAGTTCCTCCGACAAGATGATGGTACTAATTATGGTACTTTTCACTCACTTTGCACCTTTCCCTG

TCGCTCTCTAAGCACTTTACCTGGATGGCGCGTGGGCAGTGTGCAGGCAGGTCCTGAGGCCTGGGGTTGG

GGTGGAGGGTGCGGCCCGGAGTTGTCCATCTGTCCATCCCAACAGCAAGACGAGGATGTGGCTGTTGAGA

TGTGGGCCACACTCACCCTTGTCCAGGATGCAGGGACTGCCTTCTCCTTCCTGCTTCATCCGGCTTAGCT

TGGGGCTGGCTGCATTCCCCCAGGATGGGCTTCGAGAAAGACAAACTTGTCTGGAAACCAGAGTTGCTGA

TTCCACCCGGGGGGCCCGGCTGACTCGCCCATCACCTCATCTCCCTGTGGACTTGGGAGCTCTGTGCCAG

GCCCACCTTGCGGCCCTGGCTCTGAGTCGCTCTCCCACCCAGCCTGGACTTGGCCCCATGGGACCCATCC

TCAGTGCTCCCTCCAGATCCCGTCCGGCAGCTTGGCGTCCACCCTGCACAGCATCACTGAATCACAGAGC

CTTTGCGTGAAACAGCTCTGCCAGGCCGGGAGCTGGGTTTCTCTTCCCTTTTTATCTGCTGGTGTGGACC

ACACCTGGGCCTGGCCGGAGGAAGAGAGAGTTTACCAAGAGAGATGTCTCCGGGCCCTTATTTATTATTT

AAACATTTTTTTAAAAAGCACTGCTAGTTTACTTGTCTCTCCTCCCCATCGTCCCCATCGTCCTCCTTGT

CCCTGACTTGGGGCACTTCCACCCTGACCCAGCCAGTCCAGCTCTGCCTTGCCGGCTCTCCAGAGTAGAC

ATAGTGTGTGGGGTTGGAGCTCTGGCACCCGGGGAGGTAGCATTTCCCTGCAGATGGTACAGATGTTCCT

GCCTTAGAGTCATCTCTAGTTCCCCACCTCAATCCCGGCATCCAGCCTTCAGTCCCGCCCACGTGCTAGC

TCCGTGGGCCCACCGTGCGGCCTTAGAGGTTTCCCTCCTTCCTTTCCACTGAAAAGCACATGGCCTTGGG

TGACAAATTCCTCTTTGATGAATGTACCCTGTGGGGATGTTTCATACTGACAGATTATTTTTATTTATTC

AATGTCATATTTAAAATATTTATTTTTTATACCAAATGAATACTTTTTTTTTAAGAAAAAAAAGAGAAA

TGAATAAAGAATCTACTCTTG

-continued

NM_001077494.3 *Homo sapiens* nuclear factor kappa B subunit 2 (NFKB2), transcript variant 1, mRNA (SEQ ID NO: 20)

CCGCAACCAGAGCCGCCGCCACGGTGAGTGGCTGGATTCAGACCCCTGGGTGGCCGGGACAAGAGAAAAG

AGGGAGGAGGGCCTTTAGCGGACAGCGCCTGGGGCTGGAGAGCAGCAGCTGCACACAGCCGGAAAGGGCG

CGCAGGCGACGACACTCGGATCCACGTCGACACCGTTGTACAAAGATACGCGGACCCGCGGGCGTCTAAA

ATTCTGGGAAGCAGAACCTGGCCGGAGCCACTAGACAGAGCCGGGCCTAGCCCAGAGACATGGAGAGTTG

CTACAACCCAGGTCTGGATGGTATTATTGAATATGATGATTTCAAATTGAACTCCTCCATTGTGGAACCC

AAGGAGCCAGCCCCAGAAACAGCTGATGGCCCCTACCTGGTGATCGTGGAACAGCCTAAGCAGAGAGGCT

TCCGATTTCGATATGGCTGTGAAGGCCCCTCCCATGGAGGACTGCCCGGTGCCTCCAGTGAGAAGGGCCG

AAAGACCTATCCCACTGTCAAGATCTGTAACTACGAGGGACCAGCCAAGATCGAGGTGGACCTGGTAACA

CACAGTGACCCACCTCGTGCTCATGCCCACAGTCTGGTGGGCAAGCAATGCTCGGAGCTGGGGATCTGCG

CCGTTTCTGTGGGGCCCAAGGACATGACTGCCCAATTTAACAACCTGGGTGTCCTGCATGTGACTAAGAA

GAACATGATGGGGACTATGATACAAAAACTTCAGAGGCAGCGGCTCCGCTCTAGGCCCCAGGGCCTTACG

GAGGCCGAGCAGCGGGAGCTGGAGCAAGAGGCCAAAGAACTGAAGAAGGTGATGGATCTGAGTATAGTGC

GGCTGCGCTTCTCTGCCTTCCTTAGAGCCAGTGATGGCTCCTTCTCCCTGCCCCTGAAGCCAGTCATCTC

CCAGCCCATCCATGACAGCAAATCTCCGGGGGCATCAAACCTGAAGATTTCTCGAATGGACAAGACAGCA

GGCTCTGTGCGGGGTGGAGATGAAGTTTATCTGCTTTGTGACAAGGTGCAGAAAGATGACATTGAGGTTC

GGTTCTATGAGGATGATGAGAATGGATGGCAGGCCTTTGGGGACTTCTCTCCCACAGATGTGCATAAACA

GTATGCCATTGTGTTCCGGACACCCCCCTATCACAAGATGAAGATTGAGCGGCCTGTAACAGTGTTTCTG

CAACTGAAACGCAAGCGAGGAGGGGACGTGTCTGATTCCAAACAGTTCACCTATTACCCTCTGGTGGAAG

ACAAGGAAGAGGTGCAGCGGAAGCGGAGGAAGGCCTTGCCCACCTTCTCCCAGCCCTTCGGGGGTGGCTC

CCACATGGGTGGAGGCTCTGGGGGTGCAGCCGGGGGCTACGGAGGAGCTGGAGGAGGTGGCAGCCTCGGT

TTCTTCCCCTCCTCCCTGGCCTACAGCCCCTACCAGTCCGGCGCGGGCCCCATGGGCTGCTACCCGGGAG

GCGGGGGCGGGGCGCAGATGGCCGCCACGGTGCCCAGCAGGGACTCCGGGGAGGAAGCCGCGGAGCCGAG

CGCCCCCTCCAGGACCCCCCAGTGCGAGCCGCAGGCCCCGGAGATGCTGCAGCGAGCTCGAGAGTACAAC

GCGCGCCTGTTCGGCCTGGCGCAGCGCAGCGCCCGAGCCCTACTCGACTACGGCGTCACCGCGGACGCGC

GCGCGCTGCTGGCGGGACAGCGCCACCTGCTGACGGCGCAGGACGAGAACGGAGACACACCACTGCACCT

AGCCATCATCCACGGGCAGACCAGTGTCATTGAGCAGATAGTCTATGTCATCCACCACGCCCAGGACCTC

GGCGTTGTCAACCTCACCAACCACCTGCACCAGACGCCCCTGCACCTGGCGGTGATCACGGGGCAGACGA

GTGTGGTGAGCTTTCTGCTGCGGGTAGGTGCAGACCCAGCTCTGCTGGATCGGCATGGAGACTCAGCCAT

GCATCTGGCGCTGCGGGCAGGCGCTGGTGCTCCTGAGCTGCTGCGTGCACTGCTTCAGAGTGGAGCTCCT

GCTGTGCCCCAGCTGTTGCATATGCCTGACTTTGAGGGACTGTATCCAGTACACCTGGCGGTCCGAGCCC

GAAGCCCTGAGTGCCTGGATCTGCTGGTGGACAGTGGGGCTGAAGTGGAGGCCACAGAGCGGCAGGGGGG

ACGAACAGCCTTGCATCTAGCCACAGAGATGGAGGAGCTGGGGTTGGTCACCCATCTGGTCACCAAGCTC

CGGGCCAACGTGAACGCTCGCACCTTTGCGGGAAACACACCCCTGCACCTGGCAGCTGGACTGGGGTACC

CGACCCTCACCCGCCTCCTTCTGAAGGCTGGTGCTGACATCCATGCTGAAAACGAGGAGCCCCTGTGCCC

ACTGCCTTCACCCCCTACCTCTGATAGCGACTCGGACTCTGAAGGGCCTGAGAAGGACACCCGAAGCAGC

TTCCGGGGCCACACGCCTCTTGACCTCACTTGCAGCACCAAGGTGAAGACCTTGCTGCTAAATGCTGCTC

AGAACACCATGGAGCCACCCCTGACCCCGCCCAGCCCAGCAGGGCCGGGACTGTCACTTGGTGATACAGC

TCTGCAGAACCTGGAGCAGCTGCTAGACGGGCCAGAAGCCCAGGGCAGCTGGGCAGAGCTGGCAGAGCGT

CTGGGGCTGCGCAGCCTGGTAGACACGTACCGACAGACAACCTCACCCAGTGGCAGCCTCCTGCGCAGCT

-continued

ACGAGCTGGCTGGCGGGGACCTGGCAGGTCTACTGGAGGCCCTGTCTGACATGGGCCTAGAGGAGGGAGT

GAGGCTGCTGAGGGGTCCAGAAACCCGAGACAAGCTGCCCAGCACAGCAGAGGTGAAGGAAGACAGTGCG

TACGGGAGCCAGTCAGTGGAGCAGGAGGCAGAGAAGCTGGGCCCACCCCCTGAGCCACCAGGAGGGCTCT

GCCACGGGCACCCCCAGCCTCAGGTGCACTGACCTGCTGCCTGCCCCCAGCCCCCTTCCCGGACCCCCTG

TACAGCGTCCCCACCTATTTCAAATCTTATTTAACACCCCACACCCACCCCTCAGTTGGGACAAATAAAG

GATTCTCATGGGAAGGGGAGGACCCCTCCTTCCCAACTTATGGCA

NM_005253.4 *Homo sapiens* FOS like 2, AP-1 transcription factor subunit (FOSL2), mRNA (SEQ ID NO: 21)

GTAGTGACTCATCTCGGGCAGAGCGCTAGGGCTCCGAGCGAACCAGCGAGCGAGCGAACGAGCGGCGCTC

GGCGGGGACAGAAAGAGGGAGAGAGAGAGAGAGAGAGAGGGAGAGGCGCGGCCGGGCGAGGCGGGCCCGT

CCGGGAGCGGGCTCCGGGGAAGGGGTGCGGGTCTGGGCGCCGGAGCGGGGAGCGGGGCCGCGTCCCTCTC

AGCGCCAGCTCTACTTGAGCCCCACGAGCCGCTGTCCCCCTGGCGCGCTCGGGGCCGCGGGACGGGCGCA

CGCCGCCTTCTCCTAGTCAAGTATCCGAGCCGCCCCGAAACTCGGGCGGCGAGTCGGCCACGGGAAGTTT

ATTCTCCGGCTCCTTTTCTAAAAGGAAGAAACAGAAGTTTCTCCCAGCGGACAGCTTTTCTTTCCGCCTT

TTTGGCCCTGTCTGAAATCGGGGGTCCCCAGGGCTGGCAGGCCAGGCTCGCTGGGCTCCTAATCTTTTTT

TTAATTTCCAATTTTTGATTGGGCCGTGGGTCCCCGCTGAGCTCCGGCTGCGCGCGGGGGCGGGAGGGCG

CGCGCAGGGGAGGGACCGAGAGACGCGCCGACTTTTTAGAGGGAGGGATCGGGTGGACAACTGGTCCCGC

GGCGCTCGCAGAGCCGGAAAGAAGTGCTGTAAGGGACGCTCGGGGGACGCTGTTCCTGAGGTGTCGCCGC

CTCCCTGTCCTCGCCCTCCGCGGTGGGGGAGAAACCCAGGAGCGAAGCCCAGAGCCCGCGGCGCGGCCGG

CGGACGAACGAGCGCGCAGCAGCCGGTGCGCGGCCGCGGCGAGGGCGGGGGAAGAAAAACACCCTGTTTC

CTCTCCGGCCCCCACCGCGGATCATGTACCAGGATTATCCCGGGAACTTTGACACCTCGTCCCGGGGCAG

CAGCGGCTCTCCTGCGCACGCCGAGTCCTACTCCAGCGGCGGCGGCGGCCAGCAGAAATTCCGGGTAGAT

ATGCCTGGCTCAGGCAGTGCATTCATCCCCACCATCAACGCCATCACGACCAGCCAGGACCTGCAGTGGA

TGGTGCAGCCCACAGTGATCACCTCCATGTCCAACCCATACCCTCGCTCGCACCCCTACAGCCCCCTGCC

GGGCCTGGCCTCTGTCCCTGGACACATGGCCCTCCCAAGACCTGGCGTGATCAAGACCATTGGCACCACC

GTGGGCCGCAGGAGGAGAGATGAGCAGCTGTCTCCTGAAGAGGAGGAGAAGCGTCGCATCCGGCGGGAGA

GGAACAAGCTGGCTGCAGCCAAGTGCCGGAACCGACGCCGGGAGCTGACAGAGAAGCTGCAGGCGGAGAC

AGAGGAGCTGGAGGAGGAGAAGTCAGGCCTGCAGAAGGAGATTGCTGAGCTGCAGAAGGAGAAGGAGAAG

CTGGAGTTCATGTTGGTGGCTCACGGCCCAGTGTGCAAGATTAGCCCCGAGGAGCGCCGATCGCCCCCAG

CCCCTGGGCTGCAGCCCATGCGCAGTGGGGGTGGCTCGGTGGGCGCTGTAGTGGTGAAACAGGAGCCCCT

GGAAGAGGACAGCCCCTCGTCCTCGTCGGCGGGGCTGGACAAGGCCCAGCGCTCTGTCATCAAGCCCATC

AGCATTGCTGGGGGCTTCTACGGTGAGGAGCCCCTGCACACCCCCATCGTGGTGACCTCCACACCTGCTG

TCACTCCGGGCACCTCGAACCTCGTCTTCACCTATCCTAGCGTCCTGGAGCAGGAGTCACCCGCATCTCC

CTCCGAATCCTGCTCCAAGGCTCACCGCAGAAGCAGTAGCAGCGGGGACCAATCATCAGACTCCTTGAAC

TCCCCCACTCTGCTGGCTCTGTAACCCAGTGCACCTCCCTCCCCAGCTCCGGAGGGGGTCCTCCTCGCTC

CTCCTTCCCAGGGACCAGCACCTTCAAGCGCTCCAGGGCCGTGAGGGCAAGAGGGGGACCTGCCACCAGG

GAGCTTCCTGGCTCTGGGGGACCCAGGTGGGACTTAGCAGTGAGTATTGGAAGACTTGGGTTGATCTCTT

AGAAGCCATGGGACCTCCTCCCTCATTCATCTTGCAAGCAAATCCCATTTCTTGAAAAGCCTTGGAGAAC

TCGGTTTGGTAGACTTGGACATCTCTCTGGCTTCTGAAGAGCCTGAAGCTGGCCTGGACCATTCCTGTCC

CTTTGTTACCATACTGTCTCTGGAGTGATGGTGTCCTTCCCTGCCCCACCACGCATGCTCAGTGCCTTTT

GGTTTCACCTTCCCTCGACTTGACCCTTTCCTCCCCCAGCGTCAGTTTCACTCCCTCTTGGTTTTTATCA

-continued

AATTTGCCATGACATTTCATCTGGGTGGTCTGAATATTAAAGCTCTTCATTTCTGGAGATGGGGCAGCAG

GTGGCTCTTCTGCTGGGGCTGACTTGTCCAGAAGGGGACAAAGTGCAATACAGAGCCTTCCCTACCCTGA

CGCCTCCCAGTCATCATCTCCAGAACTCCCAGCGGGGCTCCCTGAGCTCTCAAGGAGATGCTGCCATCAC

TGGGAGGCTCAGAGGACCCTTCCTGCCCACCTTCGGAGACGGCTTCTGGAGGAACGGCTTGGCCAGAAGA

CAGGGTGTGAGTGAGACAGTGGGGCACAGGTTGGGTTTGCCAAACGCCTAATTACCAGGCCAGGAAGCAT

GCCAACAAAGCCACACGGGTGTCCTAGCCAGCTTCCCTTCACCTGGTGTCTTGAGTAGGGCGTCTCCTGT

AATTACTGCCTTGCCATTCTGCCCCTGGACCCTTCTCTCCGGACCAGGGAGGCGTCCCTCCCTAGGAGCC

ACACATTATACTCCAAGTCCCTGCCGGGCTCCGCCTTTCCCCCACCCTGGCTCTCAGGGTGACGCCACCC

ACAGAGATTTAATGAGCGTGGGCCTGGACCTTCCCCAGATGCTGCCAGGCAGCCCCTCCCCAAGCCTCAA

AGAAGCATTTGCTGAGGATGGAGAGGCAGGGGAGGGAGGCGGGAGGCCGTCACTGGAGTGGCGTCTGCAG

CAGCTGCTGCCCCAGCACCCGCTCAGCCTGTCCTGGCTGCTCACCTCCCCGCAGGGCACCGGGCCTTTCC

TGCCCTCTGTGGTCATCTGCCACCTGCTGGATCAAGTGCTTTCTCTTTTACACTCCCCTGTCCCCACCCC

AGTGCACTCTTCTGGCCCAGGCAGCAAGCAAGCTGTGAACAGCTGGCCTGAGCTGTCGCTGTGGCTTGTG

GCTCATGCGCCATTCCTGGTTGTCTGTTGAATCTTTCTGGCTGCTGGAATTGGAGATAGGATGTTTTGCT

TCCCACTGCAGGAGAGCTGCCCCCTTTCACGGGGTTGGGGAAGGGTCCCCCTGGCCTCCAGCAGGAGCAC

AGCTCAGCAGGGTCCCTGCTGCCCACCCCTCTGAGCCTTTTCTCCCCAGGGTATGGCTCCTGCTGAGTTT

CTTGTCCAGCAGGGCCTTGACAGGAATCCAGGGAGTAGCTCCTGGCCAGAACCAGCCTCTGCGGGGCTTG

TGCTCTGCAAAGACTCTGCTGCTGGGGATTCAGCTCTAGAGGTCACAGTATCCTCGTTTGAAAGATAATT

AAGATCCCCCGTGGAGAAAGCAGTGACACATTCACACAGCTGTTCCCTCGCATGTTATTTCATGAACATG

ACCTGTTTTCGTGCACTAGACACACAGAGTGGAACAGCCGTATGCTTAAAGTACATGGGCCAGTGGGACT

GGAAGTGACCTGTACAAGTGATGCAGAAAGGAGGGTTTCAAAGAAAAAGGATTTTGTTTAAAATACTTTA

AAAATGTTATTTCCTGCATCCCTTGGCTGTGATGCCCCTCTCCCGATTTCCCAGGGGCTCTGGGAGGGAC

CCTTCTAAGAAGATTGGGCAGTTGGGTTTCTGGCTTGAGATGAATCCAAGCAGCAGAATGAGCCAGGAGT

AGCAGGAGATGGGCAAAGAAAACTGGGGTGCACTCAGCTCTCACAGGGGTAATCATCTCAAGTGGTATTT

GTAGCCAAGTGGGAGCTATTTTCTTTTTTGTGCATATAGATATTTCTTAAATGAAGCTGCTTTCTTGTCT

TTTATTTCTAAAAGCCCCCTTATACCCCACTTTGTGCAGCAAAGATCCCCGTGCAGGTCACAGCCTGATT

TGTGGCCAGGCTGGACAAATTCCTGAGGCACAACTTGGCTTCAGTTCAGATTTCAAGCTGTGTTGGTGTT

GGGACCAGCAGAAGGCAAACGTCCAGCCAACACACAGGACTGTAAGAGGACTCTGAGCTACGTGCCCTGT

GAAGACCCCCAGGCTTTGTCATAGGAGGTCGTTCAGCTTCCCCAAAGTCAGAGGTGATTTGATTTGGGGA

AGACTGAATATTCACACCTAAGTCGTGAGCATATCCTGAGTTTTACTTCCTTATGGCTTGCCCTCCAAGT

TCTCTCTCTCATACACACACACACCCTTGCTCCAGAATCACCAGACACCTCCATGGCTCCAGCTATGGGA

ACAGCTGCATTGGGGCTGCCTTTCTGTTTGGCTTAGGAACTTCTGTGCTTCTTGTGGCTCCACTCGCGAG

GCAGCTCGGAGGTGTGGACTCCGATTGGGCTGCAGGCAGCTCTGGGACGGCACAGGGCGGGCGCTCTGAT

CAGCTCGTGTAAAACACACCGTCTTCTTGGCCTCCTGGCCAGTCTTTCTGCGAATAGTCCTCTCCCTGGC

CAGTTGAATGGGGGAAGCTGCTGGCACAGGAAGGAGAGGCGATCCCGGCTGAGGCTTAGGAAATTGCTGG

AGCCGGCTCCAAGCAGATAATTCACTGGGGAGGTTTTCAGAGTCAAACATCATTCTGCCTGTGTTGGGGG

CCAGGTGTGTCACACAAGCATCTCAAAGTCAAAAGCCATCTGGGGCTGCTGCTTCTGTTTCTCAGGCTCT

GGGGAAAGGAATCTCCCTCTCCTCTCACTTGATTCCAAGTGTGGTTGAATTGTCTGGAGCACTGGGACTT

TTTTTCTCTTTTCCTTGATGGACCAACAGTGCAAATGCAATCTCGCCATTTAACTTTCAGGTCGATTTCC

TTTCCTGATCAGACATCTTTGTGCCCCCTTTAGGAAGGAAAAGAATACACCTACGATGTGCCAGGCACTG

-continued

TGTTAGGCGCTTTTATATAGATCCTCGTTAGGATGAGACTAAGGGATGAGGACATCTCTTTATAAAAGGC

CCCTAAGTAATGGATAAACAGAAACACTTAGAGGTGAGAAGGTCTGTCTTCAAGATCCAAGGTAAGATTG

CCTTCAGTCTGATGTTTGTTCTCAAGGACTTATCCCCTACAATATTCTCCCACTCCATACTTCTCCTTCT

ACCCCACCATGTGCTCCCGTGCACTCCTCAGATGGTCAGAGGGGTAACCCAAGTCCTTAGAGAATTTGGG

GACCAATAGAATATGTGATGTGTGAATTTTCTTTAAAAAACTTAAGGAGTCTTTGCTACCTTCTGCTTGT

TGAGTTGTTTTGGCATTCATATTAAAAGCCAGCATCTCACTATTTATTGACAGGTTGGGCTGTGTGTGTG

CGCATGTGTGTATACATTTCCAGGCGTGCCTGTGTCCTGTAGCTTTTTAAAAGGAAACCCAGTCATCCCA

CTATGAATCTGGCATCTTCTTATGCTTCTAGTGTTTTGGCCATACATCAACCAAGGGGTTTAATTTATCC

AATGCTTGACGACATGTTCAGGAGGGGCTGGATCAAATTTTGAGAGGGTTATGGAAAGGGAGGGGGAGA

AGAAATTGACATTTATTTTATTATTTATTTTAAATGTTTACATCTTCTTTATGTTGTATCAAGCCTGAAT

AGAAACTGATAGCATTAAAATACTCCGTTCCTCTCTCTCTTCTCGCTTCCTTTTTTTTTTTTTTTTTTTAAA

TTTAGGATAACACATTTTTGTTTCTAAAGTGATTTGTGATTTGTGCTGTATAAACTGTATAAAAGGTTCT

GTTTTTAAAGGTGGATTTTCATTCCTCTGGGGACAGTGGTCGCCAAGACATCTACATTGTAAGAGAACAC

AGTGGAAGATCCTGTCCTGATTCTCAAAAATTATTTTCTCTGTATGATTAAAAGTTTATTCCATTTATTT

TAGTTTGTGTTTACTTGATTTTGAGGAAGAAAATATTTGACTTTGTGTAAAGAGTAGGGTATCAGGGTGT

CTTTTCTGCCGTGGGAGATGTGTATATATATAGTATTTTGGTGTATAGTAGAAAATAAGCTTTGTGCATC

TGTATTTGAGATATGTTAATGACGTGGAGTAAAGTCAGCTGTAAGACTCTGGAGGCAAACAAGTTGTATA

TGGTTCATATGGCTCTATGGGGAATTTAATTACCTTTCTGGGCACTTTTTTTTTTTTTTTTTTTTTAAGT

AATGGTGAAATGGTCCCATTGGAGAGTCTCCTAAATAGACCTTCCAGGCAGAACCGCAAGCTCAAAATCT

TTGTATAGTTTTGAAAATTGAGGAGTAGCTTTGTTTGGAAGCCTTTCTGGTGGTGGTTTTTGTTGTTGTT

GTTGTTTTGTTGTTTTACTATATGTAATACAAGCCTACAGTATTTGCACTAAAGAAAGCTTGTTAGAAAA

AGCTTGCTGCTATGGAAGAAAGAACATATTAAAACTTCTTTCCCTTGCGATTTTTTTGGGGGAGGGGGGT

TAGCATTTCCACTTTCAGTTGAGTAGCATTTTGTAGAATAAAATGAATTAAGATTGAAGAGCC

NM_001675.4 *Homo sapiens* activating transcription factor 4 (ATF4), transcript variant 1, mRNA (SEQ ID NO: 22)

AGCCATTTCTACTTTGCCCGCCCACAGATGTAGTTTTCTCTGCGCGTGTGCGTTTTCCCTCCTCCCCGCC

CTCAGGGTCCACGGCCACCATGGCGTATTAGGGGCAGCAGTGCCTGCGGCAGCATTGGCCTTTGCAGCGG

CGGCAGCAGCACCAGGCTCTGCAGCGGCAACCCCCAGCGGCTTAAGCCATGGCGTGAGTACCGGGGCGGG

TCGTCCAGCTGTGCTCCTGGGGCCGGCGCGGGTTTTGGATTGGTGGGGTGCGGCCTGGGGCCAGGGCGGT

GCCGCCAAGGGGGAAGCGATTTAACGAGCGCCCGGGACGCGTGGTCTTTGCTTGGGTGTCCCCGAGACGC

TCGCGTGCCTGGGATCGGGAAAGCGTAGTCGGGTGCCCGGACTGCTTCCCCAGGAGCCCTACAGCCCTCG

GACCCCGAGCCCCGCAAGGGTCCCAGGGGTCTTGGCTGTTGCCCCACGAAACGTGGCAGGAACCAAGATG

GCGGCGGCAGGGCGGCGGCGCGGGCGTGAGTCAAGGGCGGGCGGTGGGCGGGGCGCGGCCGCCCTGGCCG

TATTTGGACGTGGGGACGGAGCGCTTTCCTCTTGGCGGCCGGTGGAAGAATCCCCTGGTCTCCGTGAGCG

TCCATTTTGTGGAACCTGAGTTGCAAGCAGGGAGGGGCAAATACAACTGCCCTGTTCCCGATTCTCTAGA

TGGCCGATCTAGAGAAGTCCCGCCTCATAAGTGGAAGGATGAAATTCTCAGAACAGCTAACCTCTAATGG

GAGTTGGCTTCTGATTCTCATTCAGGCTTCTCACGGCATTCAGCAGCAGCGTTGCTGTAACCGACAAAGA

CACCTTCGAATTAAGCACATTCCTCGATTCCAGCAAAGCACCGCAACATGACCGAAATGAGCTTCCTGAG

CAGCGAGGTGTTGGTGGGGGACTTGATGTCCCCCTTCGACCAGTCGGGTTTGGGGGCTGAAGAAAGCCTA

GGTCTCTTAGATGATTACCTGGAGGTGGCCAAGCACTTCAAACCTCATGGGTTCTCCAGCGACAAGGCTA

AGGCGGGCTCCTCCGAATGGCTGGCTGTGGATGGGTTGGTCAGTCCCTCCAACAACAGCAAGGAGGATGC

-continued

CTTCTCCGGGACAGATTGGATGTTGGAGAAAATGGATTTGAAGGAGTTCGACTTGGATGCCCTGTTGGGT

ATAGATGACCTGGAAACCATGCCAGATGACCTTCTGACCACGTTGGATGACACTTGTGATCTCTTTGCCC

CCCTAGTCCAGGAGACTAATAAGCAGCCCCCCCAGACGGTGAACCCAATTGGCCATCTCCCAGAAAGTTT

AACAAAACCCGACCAGGTTGCCCCCTTCACCTTCTTACAACCTCTTCCCCTTTCCCCAGGGGTCCTGTCC

TCCACTCCAGATCATTCCTTTAGTTTAGAGCTGGGCAGTGAAGTGGATATCACTGAAGGAGATAGGAAGC

CAGACTACACTGCTTACGTTGCCATGATCCCTCAGTGCATAAAGGAGGAAGACACCCCTTCAGATAATGA

TAGTGGCATCTGTATGAGCCCAGAGTCCTATCTGGGGTCTCCTCAGCACAGCCCCTCTACCAGGGGCTCT

CCAAATAGGAGCCTCCCATCTCCAGGTGTTCTCTGTGGGTCTGCCCGTCCCAAACCTTACGATCCTCCTG

GAGAGAAGATGGTAGCAGCAAAAGTAAAGGGTGAGAAACTGGATAAGAAGCTGAAAAAAATGGAGCAAAA

CAAGACAGCAGCCACTAGGTACCGCCAGAAGAAGAGGGCGGAGCAGGAGGCTCTTACTGGTGAGTGCAAA

GAGCTGGAAAAGAAGAACGAGGCTCTAAAAGAGAGGGCGGATTCCCTGGCCAAGGAGATCCAGTACCTGA

AAGATTTGATAGAAGAGGTCCGCAAGGCAAGGGGGAAGAAAAGGGTCCCCTAGTTGAGGATAGTCAGGAG

CGTCAATGTGCTTGTACATAGAGTGCTGTAGCTGTGTGTTCCAATAAATTATTTTGTAGGGAAAGTAAAA

AAAAAAAAAAA

NM_001282101.2 *Homo sapiens* Yes1 associated transcriptional regulator (YAP1), transcript variant 9, mRNA (SEQ ID NO: 23)

CTCAGTCGGGCGCAGCCGCCGCCAGGGAAAAGAAAGGGAGGAAGGAAGGAACAAGAAAAGGAAATAAAGA

GAAAGGGGAGGCGGGGAAAGGCAACGAGCTGTCCGGCCTCCGTCAAGGGAGTTGGAGGGAAAAAGTTCTC

AGGCGCCGCAGGTCCGAGTGCCTCGCAGCCCCTCCCGAGGCGCAGCCGCCAGACCAGTGGAGCCGGGGCG

CAGGGCGGGGGCGGAGGCGCCGGGGCGGGGGATGCGGGGCCGCGGCGCAGCCCCCCGGCCCTGAGAGCGA

GGACAGCGCCGCCCGGCCCGCAGCCGTCGCCGCTTCTCCACCTCGGCCCGTGGAGCCGGGGCGTCCGGGC

GTAGCCCTCGCTCGCCTGGGTCAGGGGGTGCGCGTCGGGGGAGGCAGAAGCCATGGATCCCGGGCAGCAG

CCGCCGCCTCAACCGGCCCCCCAGGGCCAAGGGCAGCCGCCTTCGCAGCCCCCGCAGGGGCAGGGCCCGC

CGTCCGGACCCGGGCAACCGGCACCCGCGGCGACCCAGGCGGCGCCGCAGGCACCCCCCGCCGGGCATCA

GATCGTGCACGTCCGCGGGGACTCGGAGACCGACCTGGAGGCGCTCTTCAACGCCGTCATGAACCCCAAG

ACGGCCAACGTGCCCCAGACCGTGCCCATGAGGCTCCGGAAGCTGCCCGACTCCTTCTTCAAGCCGCCGG

AGCCCAAATCCCACTCCCGACAGGCCAGTACTGATGCAGGCACTGCAGGAGCCCTGACTCCACAGCATGT

TCGAGCTCATTCCTCTCCAGCTTCTCTGCAGTTGGGAGCTGTTTCTCCTGGGACACTGACCCCCACTGGA

GTAGTCTCTGGCCCAGCAGCTACACCCACAGCTCAGCATCTTCGACAGTCTTCTTTTGAGATACCTGATG

ATGTACCTCTGCCAGCAGGTTGGGAGATGGCAAAGACATCTTCTGGTCAGAGATACTTCTTAAATCACAT

CGATCAGACAACAACATGGCAGGACCCCAGGAAGGCCATGCTGTCCCAGATGAACGTCACAGCCCCCACC

AGTCCACCAGTGCAGCAGAATATGATGAACTCGGCTTCAGGTCCTCTTCCTGATGGATGGGAACAAGCCA

TGACTCAGGATGGAGAAATTTACTATATAAACCATAAGAACAAGACCACCTCTTGGCTAGACCCAAGGCT

TGACCCTCGTTTTGCCATGAACCAGAGAATCAGTCAGAGTGCTCCAGTGAAACAGCCACCACCCCTGGCT

CCCCAGAGCCCACAGGGAGGCGTCATGGGTGGCAGCAACTCCAACCAGCAGCAACAGATGCGACTGCAGC

AACTGCAGATGGAGAAGGAGAGGCTGCGGCTGAAACAGCAAGAACTGCTTCGGCAGGTGAGGCCACAGGC

AATGCGGAATATCAATCCCAGCACAGCAAATTCTCCAAAATGTCAGGAGTTAGCCCTGCGTAGCCAGTTA

CCAACACTGGAGCAGGATGGTGGGACTCAAAATCCAGTGTCTTCTCCCGGGATGTCTCAGGAATTGAGAA

CAATGACGACCAATAGCTCAGATCCTTTCCTTAACAGTGGCACCTATCACTCTCGAGATGAGAGTACAGA

CAGTGGACTAAGCATGAGCAGCTACAGTGTCCCTCGAACCCCAGATGACTTCCTGAACAGTGTGGATGAG

ATGGATACAGGTGATACTATCAACCAAAGCACCCTGCCCTCACAGCAGAACCGTTTCCCAGACTACCTTG

-continued

```
AAGCCATTCCTGGGACAAATGTGGACCTTGGAACACTGGAAGGAGATGGAATGAACATAGAAGGAGAGGA
GCTGATGCCAAGTCTGCAGGAAGCTTTGAGTTCTGACATCCTTAATGACATGGAGTCTGTTTTGGCTGCC
ACCAAGCTAGATAAAGAAAGCTTTCTTACATGGTTATAGAGCCCTCAGGCAGACTGAATTCTAAATCTGT
GAAGGATCTAAGGAGACACATGCACCGGAAATTTCCATAAGCCAGTTGCAGTTTTCAGGCTAATACAGAA
AAAGATGAACAAACGTCCAGCAAGATACTTTAATCCTCTATTTTGCTCTTCCTTGTCCATTGCTGCTGTT
AATGTATTGCTGACCTCTTTCACAGTTGGCTCTAAAGAATCAAAAGAAAAAAACTTTTTATTTCTTTTGC
TATTAAAACTACTGTTCATTTTGGGGGCTGGGGGAAGTGAGCCTGTTTGGATGATGGATGCCATTCCTTT
TGCCCAGTTAAATGTTCACCAATCATTTTAACTAAATACTCAGACTTAGAAGTCAGATGCTTCATGTCAC
AGCATTTAGTTTGTTCAACAGTTGTTTCTTCAGCTTCCTTTGTCCAGTGGAAAAACATGATTTACTGGTC
TGACAAGCCAAAAATGTTATATCTGATATTAAATACTTAATGCTGATTTGAAGAGATAGCTGAAACCAAG
GCTGAAGACTGTTTTACTTTCAGTATTTTCTTTTCCTCCTAGTGCTATCATTAGTCACATAATGACCTTG
ATTTTATTTTAGGAGCTTATAAGGCATGAGACAATTTCCATATAAATATATTAATTATTGCCACATACTC
TAATATAGATTTTGGTGGATAATTTTGTGGGTGTGCATTTTGTTCTGTTTTGTTGGGTTTTTTGTTTTTT
TTGTTTTTGGCAGGGTCGGTGGGGGGGTTGGTTGGTTGGTTGGTTTTGTCGGAACCTAGGCAAATGACCA
TATTAGTGAATCTGTTAATAGTTGTAGCTTGGGATGGTTATTGTAGTTGTTTTGGTAAAATCTTCATTTC
CTGGTTTTTTTTACCACCTTATTTAAATCTCGATTATCTGCTCTCTCTTTTATATACATACACACACCCA
AACATAACATTTATAATAGTGTGGTAGTGGAATGTATCCTTTTTTAGGTTTCCCTGCTTTCCAGTTAATT
TTTAAAATGGTAGCGCTTTGTATGCATTTAGAATACATGACTAGTAGTTTATATTTCACTGGTAGTTTAA
ATCTGGTTGGGGCAGTCTGCAGATGTTTGAAGTAGTTTAGTGTTCTAGAAAGAGCTATTACTGTGGATAG
TGCCTAGGGGAGTGCTCCACGCCCTCTGGGCATACGGTAGATATTATCTGATGAATTGGAAAGGAGCAAA
CCAGAAATGGCTTTATTTTCTCCCTTGGACTAATTTTTAAGTCTCGATTGGAATTCAGTGAGTAGGTTCA
TAATGTGCATGACAGAAATAAGCTTTATAGTGGTTTACCTTCATTTAGCTTTGGAAGTTTTCTTTGCCTT
AGTTTTGGAAGTAAATTCTAGTTTGTAGTTCTCATTTGTAATGAACACATTAACGACTAGATTAAAATAT
TGCCTTCAAGATTGTTCTTACTTACAAGACTTGCTCCTACTTCTATGCTGAAAATTGACCCTGGATAGAA
TACTATAAGGTTTTGAGTTAGCTGGAAAAGTGATCAGATTAATAAATGTATATTGGTAGTTGAATTTAGC
AAAGAAATAGAGATAATCATGATTATACCTTTATTTTTACAGGAAGAGATGATGTAACTAGAGTATGTGT
CTACAGGAGTAATAATGGTTTCCAAAGAGTATTTTTTAAAGGAACAAAACGAGCATGAATTAACTCTTCA
ATATAAGCTATGAAGTAATAGTTGGTTGTGAATTAAAGTGGCACCAGCTAGCACCTCTGTGTTTTAAGGG
TCTTTCAATGTTTCTAGAATAAGCCCTTATTTTCAAGGGTTCATAACAGGCATAAAATCTCTTCTCCTGG
CAAAAGCTGCTATGAAAAGCCTCAGCTTGGGAAGATAGATTTTTTTCCCCCCAATTACAAAATCTAAGTA
TTTTGGCCCTTCAATTTGGAGGAGGGCAAAAGTTGGAAGTAAGAAGTTTTATTTTAAGTACTTTCAGTGC
TCAAAAAAATGCAATCACTGTGTTGTATATAATAGTTCATAGGTTGATCACTCATAATAATTGACTCTAA
GGCTTTTATTAAGAAAACAGCAGAAAGATTAAATCTTGAATTAAGTCTGGGGGGAAATGGCCACTGCAGA
TGGAGTTTTAGAGTAGTAATGAAATTCTACCTAGAATGCAAAATTGGGTATATGAATTACATAGCATGTT
GTTGGGATTTTTTTTAATGTGCAGAAGATCAAAGCTACTTGGAAGGAGTGCCTATAATTTGCCAGTAGCC
ACAGATTAAGATTATATCTTATATATCAGCAGATTAGCTTTAGCTTAGGGGGAGGGTGGGAAAGTTTGGG
GGGGGGGTTGTGAAGATTTAGGGGGACCTTGATAGAGAACTTTATAAACTTCTTTCTCTTTAATAAAGAC
TTGTCTTACACCGTGCTGCCATTAAAGGCAGCTGTTCTAGAGTTTCAGTCACCTAAGTACACCCACAAAA
CAATATGAATATGGAGATCTTCCTTTACCCCTCAACTTTAATTTGCCCAGTTATACCTCAGTGTTGTAGC
AGTACTGTGATACCTGGCACAGTGCTTTGATCTTACGATGCCCTCTGTACTGACCTGAAGGAGACCTAAG
AGTCCTTTCCCTTTTTGAGTTTGAATCATAGCCTTGATGTGGTCTCTTGTTTTATGTCCTTGTTCCTAAT
```

-continued

```
GTAAAAGTGCTTAACTGCTTCTTGGTTGTATTGGGTAGCATTGGGATAAGATTTTAACTGGGTATTCTTG
AATTGCTTTTACAATAAACCAATTTTATAATCTTTAAATTTATCAACTTTTTACATTTGTGTTATTTTCA
GTCAGGGCTTCTTAGATCTACTTATGGTTGATGGAGCACATTGATTTGGAGTTTCAGATCTTCCAAAGCA
CTATTTGTTGTAATAACTTTTCTAAATGTAGTGCCTTTAAAGGAAAAATGAACACAGGGAAGTGACTTTG
CTACAAATAATGTTGCTGTGTTAAGTATTCATATTAAATACATGCCTTCTATATGGAACATGGCAGAAAG
ACTGAAAAATAACAGTAATTAATTGTGTAATTCAGAATTCATACCAATCAGTGTTGAAACTCAAACATTG
CAAAAGTGGGTGGCAATATTCAGTGCTTAACACTTTTCTAGCGTTGGTACATCTGAGAAATGAGTGCTCA
GGTGGATTTTATCCTCGCAAGCATGTTGTTATAAGAATTGTGGGTGTGCCTATCATAACAATTGTTTTCT
GTATCTTGAAAAAGTATTCTCCACATTTTAAATGTTTTATATTAGAGAATTCTTTAATGCACACTTGTCA
AATATATATATATAGTACCAATGTTACCTTTTTATTTTTTGTTTTAGATGTAAGAGCATGCTCATATGTT
AGGTACTTACATAAATTGTTACATTATTTTTTCTTATGTAATACCTTTTTGTTTGTTTATGTGGTTCAAA
TATATTCTTTCCTTAAACTCTTC
```

The present disclosure also provides an antisense nucleic acid comprising a nucleic acid sequence that is complementary to and specifically hybridizes with a portion of any one of SEQ ID NOs: 15-23, thereby reducing or inhibiting gene expression. The antisense nucleic acid may be antisense RNA, or antisense DNA. Antisense nucleic acids based on the known gene sequences of SLC4A11, OC2, MYC, RELB, LIF, NFKB2, FOSL2, ATF4, and YAP can be readily designed and engineered using methods known in the art. In some embodiments, the antisense nucleic acid comprises the nucleic acid sequence of SEQ ID NO: 3, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, or a complement thereof.

Antisense nucleic acids are molecules which are complementary to a sense nucleic acid strand, e.g., complementary to the coding strand of a double-stranded DNA molecule (or cDNA) or complementary to an mRNA sequence. Accordingly, an antisense nucleic acid can form hydrogen bonds with a sense nucleic acid. The antisense nucleic acid can be complementary to an entire coding strand of a gene selected from among SLC4A11, OC2, MYC, RELB, LIF, NFKB2, FOSL2, ATF4, or YAP, or to a portion thereof, e.g., all or part of the protein coding region (or open reading frame). In some embodiments, the antisense nucleic acid is an oligonucleotide which is complementary to only a portion of the coding region of a SLC4A11, OC2, MYC, RELB, LIF, NFKB2, FOSL2, ATF4, or YAP mRNA. In certain embodiments, an antisense nucleic acid molecule can be complementary to a noncoding region of the coding strand of a SLC4A11, OC2, MYC, RELB, LIF, NFKB2, FOSL2, ATF4, or YAP mRNA. In some embodiments, the noncoding region refers to the 5' and 3' untranslated regions that flank the coding region and are not translated into amino acids. For example, the antisense oligonucleotide can be complementary to the region surrounding the translation start site of a SLC4A11, OC2, MYC, RELB, LIF, NFKB2, FOSL2, ATF4, or YAP mRNA. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides. Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thouridine, 5-carboxymethylaminometh-yluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-metnylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutosine, pseudouracil, queosine, 2-thiocytosine, 5-methyl-2-thiouracil, 2-thlouracil, 4-thiouracil, 5-methyluracil, uracil-5-oxyacetic acid methylester, uracil-5-cxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules may be administered to a subject or generated in situ such that they hybridize with or bind to cellular mRNA and/or genomic DNA encoding the protein of interest to thereby inhibit expression of the protein, e.g., by inhibiting transcription and/or translation. The hybridization can occur via Watson-Crick base pairing to form a stable duplex, or in the case of an antisense nucleic acid molecule which binds to DNA duplexes, through specific interactions in the major groove of the double helix.

In some embodiments, the antisense nucleic acid molecules are modified such that they specifically bind to receptors or antigens expressed on a selected cell surface, e.g., by linking the antisense nucleic acid molecules to peptides or antibodies which bind to cell surface receptors or antigens. In some embodiments, the antisense nucleic acid molecule is an alpha-anomeric nucleic acid molecule. An alpha-anomeric nucleic acid molecule forms specific double-stranded hybrids with complementary RNA in which, contrary to the usual β-units, the strands run parallel to each other (Gaultier et al., *Nucleic Acids. Res.* 15:6625-6641(1987)). The antisense nucleic acid molecule can also comprise a 2'-O-methylribonucleotide (Inoue et al., *Nucleic Acids Res.* 15:6131-6148 (1987)) or a chimeric RNA-DNA analogue (Inoue et al., *FEBS Lett.* 215:327-330 (1987)).

The present disclosure also provides a short hairpin RNA (shRNA) or small interfering RNA (siRNA) comprising a nucleic acid sequence that is complementary to and specifically hybridizes with a portion of any one of SEQ ID NOs: 15-23, thereby reducing or inhibiting gene expression. In some embodiments, the shRNA or siRNA is about 18, 19, 20, 21, 22, 23, 24, 25, 26, 27, 28 or 29 base pairs in length. Double-stranded RNA (dsRNA) can induce sequence-specific post-transcriptional gene silencing (e.g., RNA interference (RNAi)) in many organisms such as *C. elegans, Drosophila,* plants, mammals, oocytes and early embryos. RNAi is a process that interferes with or significantly reduces the number of protein copies made by an mRNA. For example, a double-stranded siRNA or shRNA molecule is engineered to complement and hydridize to a mRNA of a target gene. Following intracellular delivery, the siRNA or shRNA molecule associates with an RNA-induced silencing complex (RISC), which then binds and degrades a complementary target mRNA (such as SLC4A11, OC2, MYC, RELB, LIF, NFKB2, FOSL2, ATF4, or YAP mRNA). In some embodiments, the shRNA or siRNA comprises the nucleic acid sequence of SEQ ID NO: 3, SEQ ID NO: 5, SEQ ID NO: 6, SEQ ID NO: 7, SEQ ID NO: 8, SEQ ID NO: 9, SEQ ID NO: 11, SEQ ID NO: 12, or SEQ ID NO: 13.

The present disclosure also provides a ribozyme comprising a nucleic acid sequence that is complementary to and specifically hybridizes with a portion of any one of SEQ ID NOs: 15-23, thereby reducing or inhibiting gene expression. Ribozymes are catalytic RNA molecules with ribonuclease activity which are capable of cleaving a complementary single-stranded nucleic acid, such as an mRNA. Thus, ribozymes (e.g., hammerhead ribozymes (described in Haselhoff and Gerlach, *Nature* 334:585-591 (1988))) can be used to catalytically cleave SLC4A11, OC2, MYC, RELB, LIF, NFKB2, FOSL2, ATF4, or YAP transcripts, thereby inhibiting translation of SLC4A11, OC2, MYC, RELB, LIF, NFKB2, FOSL2, ATF4, or YAP.

A ribozyme having specificity for a SLC4A11, OC2, MYC, RELB, LIF, NFKB2, FOSL2, ATF4, or YAP-encoding nucleic acid can be designed based upon a target nucleic acid sequence disclosed herein. For example, a derivative of a Tetrahymena L-19 IVS RNA can be constructed in which the nucleotide sequence of the active site is complementary to the nucleotide sequence to be cleaved in a SLC4A11, OC2, MYC, RELB, LIF, NFKB2, FOSL2, ATF4, or YAP-encoding mRNA. See, e.g., U.S. Pat. Nos. 4,987,071 and 5,116,742. Alternatively, SLC4A11, OC2, MYC, RELB, LIF, NFKB2, FOSL2, ATF4, or YAP mRNA can be used to select a catalytic RNA having a specific ribonuclease activity from a pool of RNA molecules. See, e.g., Bartel and Szostak (1993) *Science* 261:1411-1418, incorporated herein by reference.

The present disclosure also provides a synthetic guide RNA (sgRNA) comprising a nucleic acid sequence that is complementary to and specifically hybridizes with a portion of any one of SEQ ID NOs: 15-23. Guide RNAs for use in CRISPR-Cas systems are typically generated as a single guide RNA comprising a crRNA segment and a tracrRNA segment. The crRNA segment and a tracrRNA segment can also be generated as separate RNA molecules. The crRNA segment comprises the targeting sequence that binds to a portion of any one of SEQ ID NOs: 15-23, and a stem portion that hybridizes to a tracrRNA. The tracrRNA segment comprises a nucleotide sequence that is partially or completely complementary to the stem sequence of the crRNA and a nucleotide sequence that binds to the CRISPR enzyme. In some embodiments, the crRNA segment and the tracrRNA segment are provided as a single guide RNA. In some embodiments, the crRNA segment and the tracrRNA segment are provided as separate RNAs. The combination of the CRISPR enzyme with the crRNA and tracrRNA make up a functional CRISPR-Cas system. Exemplary CRISPR-Cas systems for targeting nucleic acids, are described, for example, in WO2015/089465.

In some embodiments, a synthetic guide RNA is a single RNA represented as comprising the following elements:

5'-X1-X2-Y—Z-3' where X1 and X2 represent the crRNA segment, where X1 is the targeting sequence that binds to a portion of any one of SEQ ID NOs: 15-23, X2 is a stem sequence the hybridizes to a tracrRNA, Z represents a tracrRNA segment comprising a nucleotide sequence that is partially or completely complementary to X2, and Y represents a linker sequence. In some embodiments, the linker sequence comprises two or more nucleotides and links the crRNA and tracrRNA segments. In some embodiments, the linker sequence comprises 2, 3, 4, 5, 6, 7, 8, 9, 10 or more nucleotides. In some embodiments, the linker is the loop of the hairpin structure formed when the stem sequence hybridized with the tracrRNA.

In some embodiments, a synthetic guide RNA is provided as two separate RNAs where one RNA represents a crRNA segment: 5'-X1-X2-3' where X1 is the targeting sequence that binds to a portion of any one of SEQ ID NOs: 15-23, X2 is a stem sequence the hybridizes to a tracrRNA, and one RNA represents a tracrRNA segment, Z, that is a separate RNA from the crRNA segment and comprises a nucleotide sequence that is partially or completely complementary to X2 of the crRNA.

Exemplary crRNA stem sequences and tracrRNA sequences are provided, for example, in WO/2015/089465, which is incorporated by reference herein. In general, a stem sequence includes any sequence that has sufficient complementarity with a complementary sequence in the tracrRNA to promote formation of a CRISPR complex at a target sequence, wherein the CRISPR complex comprises the stem sequence hybridized to the tracrRNA. In general, degree of complementarity is with reference to the optimal alignment of the stem and complementary sequence in the tracrRNA, along the length of the shorter of the two sequences. Optimal alignment may be determined by any suitable alignment algorithm, and may further account for secondary structures, such as self-complementarity within either the stem sequence or the complementary sequence in the tracrRNA. In some embodiments, the degree of complementarity between the stem sequence and the complementary sequence in the tracrRNA along the length of the shorter of the two when optimally aligned is about or more than about 25%, 30%, 40%, 50%, 60%, 70%, 80%, 90%, 95%, 97.5%, 99%, or higher. In some embodiments, the stem sequence is about or more than about 5, 6, 7, 8, 9, 10, 11, 12, 13, 14, 15, 16, 17, 18, 19, 20, 25, 30, 40, 50, or more nucleotides in length. In some embodiments, the stem sequence and complementary sequence in the tracrRNA are contained within a single RNA, such that hybridization between the two produces a transcript having a secondary structure, such as a hairpin. In some embodiments, the tracrRNA has additional complementary sequences that form hairpins. In some embodiments, the tracrRNA has at least two or more hairpins. In some embodiments, the tracrRNA has two, three, four or five hairpins. In some embodiments, the tracrRNA has at most five hairpins.

In a hairpin structure, the portion of the sequence 5' of the final "N" and upstream of the loop corresponds to the crRNA stem sequence, and the portion of the sequence 3' of the loop corresponds to the tracrRNA sequence. Further non-limiting examples of single polynucleotides comprising a guide sequence, a stem sequence, and a tracr sequence are as follows (listed 5' to 3'), where "N" represents a base of a guide sequence (e.g. a modified oligonucleotide provided herein), the first block of lower case letters represent stem sequence, and the second block of lower case letters represent the tracrRNA sequence, and the final poly-T sequence represents the transcription terminator:

```
(a)
                                        (SEQ ID NO: 24)
NNNNNNNNNNNNNNNNNNNNgtttttgtactctcaagatttaGAAAtaaa

tcttgcagaagctacaaagataaggcttcatgccgaaatcaacaccctgt

cattnatggcagggtgttncgttatttaaTTTTTT;

(b)
                                        (SEQ ID NO: 25)
NNNNNNNNNNNNNNNNNNNNgtttttgtactctcaGAAAtgcagaagcta

caaagataaggcttcatgccgaaatcaacaccctgtcattnatggcaggg

tgttncgttatttaaTTTTTT;

(c)
                                        (SEQ ID NO: 26)
NNNNNNNNNNNNNNNNNNNNgtttttgtactctcaGAAAtgcagaagcta

caaagataaggcttcatgccgaaatcaacaccctgtcattnatggcaggg

tgtTTTTTT;

(d)
                                        (SEQ ID NO: 27)
NNNNNNNNNNNNNNNNNNNNgttttagagctaGAAAtagcaagttaaaat

aaggctagtccgttatcaacttgaaaaagtggcaccgagtcggtgcTTTT

TT;

(e)
                                        (SEQ ID NO: 28)
NNNNNNNNNNNNNNNNNNNNgttttagagctaGAAATAGcaagttaaaat

aaggctagtccgttatcaacttgaaaaagtgTTTTTTT;
and

(f)
                                        (SEQ ID NO: 29)
NNNNNNNNNNNNNNNNNNNNgttttagagctagAAATAGcaagttaaaat

aaggctagtccgttatcaTTTTTTTT.
```

Selection of suitable oligonucleotides for use in as a targeting sequence in a CRISPR Cas system depends on several factors including the particular CRISPR enzyme to be used and the presence of corresponding proto-spacer adjacent motifs (PAMs) downstream of the target sequence in the target nucleic acid. The PAM sequences direct the cleavage of the target nucleic acid by the CRISPR enzyme. In some embodiments, a suitable PAM is 5'-NRG or 5'-NNGRR (where N is any Nucleotide) for SpCas9 or SaCas9 enzymes (or derived enzymes), respectively. Generally the PAM sequences should be present between about 1 to about 10 nucleotides of the target sequence to generate efficient cleavage of the target nucleic acid. Thus, when the guide RNA forms a complex with the CRISPR enzyme, the complex locates the target and PAM sequence, unwinds the DNA duplex, and the guide RNA anneals to the complementary sequence on the opposite strand. This enables the Cas9 nuclease to create a double-strand break. In some embodiments, the sgRNA comprises the nucleic acid sequence of SEQ ID NO: 3, SEQ ID NO: 5, SEQ ID NO: 6, SEQ ID NO: 7, SEQ ID NO: 8, SEQ ID NO: 9, SEQ ID NO: 11, SEQ ID NO: 12, or SEQ ID NO: 13.

A variety of CRISPR enzymes are available for use in conjunction with the disclosed guide RNAs of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any chimeras, mutants, homologs or orthologs. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified variants thereof. In some embodiments, the CRISPR enzyme cleaves both strands of the target nucleic acid at the Protospacer Adjacent Motif (PAM) site. In some embodiments, the CRISPR enzyme is a nickase, which cleaves only one strand of the target nucleic acid.

Methods of the Present Technology

The following discussion is presented by way of example only, and is not intended to be limiting.

In one aspect, the present disclosure provides a method for detecting the presence of high-plasticity cell state (HPCS) in a biological sample obtained from a lung cancer patient comprising: detecting the presence of HPCS in the biological sample by detecting SLC4A11 mRNA or polypeptide levels in the biological sample that are at least 5% higher compared to a reference sample. In certain embodiments, the SLC4A11 mRNA or polypeptide levels in the biological sample are increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 100% compared to a reference sample. Alternatively, the present disclosure provides a method for detecting the presence of high-plasticity cell state (HPCS) in a biological sample obtained from a lung cancer patient comprising: detecting the presence of HPCS in the biological sample by detecting SLC4A11 mRNA or polypeptide levels in the biological sample that are at least 0.5-fold higher compared to a reference sample. In certain embodiments, the SLC4A11 mRNA or polypeptide levels in the biological sample are increased by at least 0.5-fold, at least 1.0 fold, at least 1.5-fold, at least 2.0 fold, at least 2.5-fold, at least 3.0 fold, at least 3.5-fold, at least 4.0 fold, at least 4.5-fold, at least 5.0 fold, at least 5.5-fold, at least 6.0 fold, at least 6.5-fold, at least 7.0 fold, at least 7.5-fold, at least 8.0 fold, at least 8.5-fold, at least 9.0 fold, at least 9.5-fold, or at least 10.0 fold compared to a reference sample. The reference sample may be obtained from a healthy control subject or may contain a predetermined level of the SLC4A11 mRNA or polypeptide. In some embodiments of the methods disclosed herein, the polypeptide levels are detected via Western Blotting, flow cytometry, Enzyme-linked immunosorbent assay (ELISA), dot blotting, immunohistochemistry, immunofluorescence, immunoprecipitation, immunoelectrophoresis, High-performance liquid chromatography (HPLC), or mass-spectrometry. In certain embodiments of the methods disclosed herein, the mRNA levels are detected via in situ hybridization, reverse transcriptase polymerase chain reaction (RT-PCR), RNA-Seq, Northern blotting, microarray, dot or slot blots, fluorescent in situ hybridization (FISH), electrophoresis, chromatography, or mass spectroscopy. Additionally or alternatively, in some embodiments, the biological sample is obtained from a patient diagnosed with or at risk for lung adenocarcinoma. The biological sample may be tissues (e.g., lung cancer biopsy), cells or biological fluids (blood, plasma, saliva, urine, serum etc.) present within a subject.

One aspect of the present technology includes methods of treating or eliminating HPCS in lung cancer patients. In some embodiments, HPCS harbors high tumorigenic capacity, is drug resistant, and is associated with poor patient prognosis. In some embodiments, HPCS in lung cancer tumors is characterized by elevated expression levels and/or increased activity of SLC4A11, OC2, MYC, RELB, LIF, NFKB2, FOSL2, ATF4, and/or YAP. In some embodiments, the subjects are diagnosed with non-small cell lung cancer (NSCLC). The main subtypes of NSCLC are lung adenocarcinoma (LUAD), squamous cell carcinoma (SCC), and large cell carcinoma.

In one aspect, the present disclosure provides a method for inhibiting lung tumor cell proliferation in a subject in need thereof, comprising administering to the subject a therapeutically effective amount of an immunotherapeutic agent comprising an antibody or antigen binding fragment that specifically binds to SLC4A11 disclosed herein, or a SLC4A11-, OC2-, MYC-, RELB-, LIF-, NFKB2-, FOSL2-, ATF4-, or YAP-specific inhibitory nucleic acid disclosed herein. In certain embodiments, the immunotherapeutic agent comprising an antibody or antigen binding fragment that specifically binds to SLC4A11 is an antibody drug conjugate, a Bi-specific T-cell engager (BiTE), a CAR T cell, or a tri-specific natural killer cell engager. In some embodiments, the SLC4A11-, OC2-, MYC-, RELB-, LIF-, NFKB2-, FOSL2-, ATF4-, or YAP-specific inhibitory nucleic acid is selected from the group consisting of antisense oligonucleotide, sgRNA, shRNA, and siRNA. Additionally or alternatively, in some embodiments, the lung tumors exhibit HPCS that is characterized by elevated expression levels and/or increased activity of SLC4A11, OC2, MYC, RELB, LIF, NFKB2, FOSL2, ATF4, and/or YAP. Additionally or alternatively, in some embodiments, the subject is diagnosed as having, suspected as having, or at risk of having lung cancer.

In therapeutic applications, compositions or medicaments comprising a SLC4A11-, OC2-, MYC-, RELB-, LIF-, NFKB2-, FOSL2-, ATF4-, or YAP-specific inhibitory nucleic acid disclosed herein or an immunotherapeutic agent comprising an antibody or antigen binding fragment that specifically binds to SLC4A11 disclosed herein, are administered to a subject suspected of having, or already suffering from lung cancer, in an amount sufficient to cure, or at least partially arrest, the symptoms of the disease, including its complications and intermediate pathological phenotypes in development of the disease.

Subjects suffering from lung cancer can be identified by any or a combination of diagnostic or prognostic assays known in the art. For example, typical symptoms of lung cancer include, but are not limited to, incessant coughing, chest pain, shortness of breath, wheezing, coughing up blood, chronic fatigue, weight loss with no known cause, repeated bouts of pneumonia and swollen or enlarged lymph nodes (glands) inside the chest in the area between the lungs.

In some embodiments, the subject may exhibit one or more mutations in KRAS, BRAF, P53, EGFR, PIK3CA, HER2, DDR2, PIK3CA, PTEN or H3F3A and/or one or more chromosomal alterations (e.g., an inversion, translocation, duplication, or gene fusion) such as gene amplifications in MET, HER2, FGFR1, or PDGFRA and/or gene rearrangements in ALK, NTRK, NRG1, ROS1, or RET. Such mutations and chromosomal alterations are detectable using techniques known in the art.

In some embodiments, treatment with the therapeutic agent described herein (e.g., SLC4A11-, OC2-, MYC-, RELB-, LIF-, NFKB2-, FOSL2-, ATF4-, or YAP-specific inhibitory nucleic acid or an immunotherapeutic agent comprising an antibody or antigen binding fragment that specifically binds to SLC4A11) will result in the amelioration or elimination of one or more of the following symptoms: incessant coughing, chest pain, shortness of breath, wheezing, coughing up blood, chronic fatigue, weight loss with no known cause, repeated bouts of pneumonia and swollen or enlarged lymph nodes (glands) inside the chest in the area between the lungs.

In certain embodiments, subjects with lung cancer characterized by elevated expression levels and/or increased activity of SLC4A11, OC2, MYC, RELB, LIF, NFKB2, FOSL2, ATF4, and/or YAP, and/or subjects exhibiting HPCS in lung cancer tumors that are treated with the therapeutic agent described herein (e.g., SLC4A11-, OC2-, MYC-, RELB-, LIF-, NFKB2-, FOSL2-, ATF4-, or YAP-specific inhibitory nucleic acid or an immunotherapeutic agent comprising an antibody or antigen binding fragment that specifically binds to SLC4A11) will show reduced lung tumor cell proliferation and/or increased survival compared to untreated lung cancer subjects. In certain embodiments, lung cancer subjects exhibiting HPCS that are treated with any of the therapeutic agents of the present technology will show SLC4A11, OC2, MYC, RELB, LIF, NFKB2, FOSL2, ATF4, and/or YAP expression levels that are reduced compared to untreated lung cancer subjects.

In one aspect, the present disclosure provides a method for monitoring the efficacy of a therapeutic agent in eliminating HPCS in a subject diagnosed with lung cancer comprising: (a) detecting SLC4A11 protein levels in a test sample obtained from the subject after the subject has been administered the therapeutic agent; and (b) determining that the therapeutic agent is effective when the SLC4A11 protein levels in the test sample are reduced compared to that observed in a control sample obtained from the subject prior to administration of the therapeutic agent. The therapeutic agent may be an antisense oligonucleotide, a sgRNA, a shRNA, a ribozyme, or a siRNA that specifically inhibits expression of SLC4A11, OC2, MYC, RELB, LIF, NFKB2, FOSL2, ATF4, and/or YAP. Alternatively, the therapeutic agent is an immunotherapeutic agent comprising an antibody or antigen binding fragment that specifically binds to SLC4A11, such as an antibody drug conjugate, a Bi-specific T-cell engager (BiTE), a CAR T cell, or a tri-specific natural killer cell engager. The test sample may be tissues, cells or biological fluids (blood, plasma, saliva, urine, serum etc.) present within a subject.

Alternatively, Tigit or Integrin α2 expression levels may be used to determine efficacy of the therapeutic agents disclosed herein in the subject. Accordingly, in certain embodiments, the method further comprises detecting expression levels of Tigit or Integrin α2 in the subject, wherein a decrease in Tigit or Integrin α2 expression levels relative to those observed in the subject prior to treatment is indicative of the therapeutic efficacy of the therapeutic agent.

In one aspect, the present technology provides a method for preventing or delaying the onset of HPCS in lung cancer patients. In some embodiments, HPCS in lung cancer tumors is characterized by elevated expression levels and/or increased activity of SLC4A11, OC2, MYC, RELB, LIF, NFKB2, FOSL2, ATF4, and/or YAP.

Subjects at risk or susceptible to lung cancer include those that exhibit one or more mutations in KRAS, BRAF, P53, EGFR, PIK3CA, HER2, DDR2, PIK3CA, PTEN or H3F3A and/or one or more chromosomal alterations (e.g., an inversion, translocation, duplication, or gene fusion) such as gene amplifications in MET, HER2, FGFR1, or PDGFRA and/or gene rearrangements in ALK, NTRK, NRG1, ROS1, or RET. In some embodiments, the subjects are diagnosed with non-small cell lung cancer (NSCLC). The main subtypes of NSCLC are lung adenocarcinoma (LUAD), squamous cell carcinoma (SCC), and large cell carcinoma. Such subjects can be identified by, e.g., any or a combination of diagnostic or prognostic assays known in the art.

In prophylactic applications, pharmaceutical compositions or medicaments comprising a SLC4A11-, OC2-, MYC-, RELB-, LIF-, NFKB2-, FOSL2-, ATF4-, or YAP-specific inhibitory nucleic acid disclosed herein or an immunotherapeutic agent comprising an antibody or antigen binding fragment that specifically binds to SLC4A11 disclosed herein are administered to a subject susceptible to, or otherwise at risk of lung cancer patients, in an amount sufficient to eliminate or reduce the risk, or delay the onset of HPCS in lung cancer, including biochemical, histologic and/or behavioral symptoms of the disease, its complications and intermediate pathological phenotypes presenting during development of the disease. Administration of a prophylactic agent (e.g., SLC4A11-, OC2-, MYC-, RELB-, LIF-, NFKB2-, FOSL2-, ATF4-, or YAP-specific inhibitory nucleic acid or an immunotherapeutic agent comprising an antibody or antigen binding fragment that specifically binds to SLC4A11) can occur prior to the manifestation of symptoms characteristic of HPCS in lung tumors, such that the HPCS in lung tumors is prevented or, alternatively, delayed in its progression.

In some embodiments, treatment with the prophylactic agent described herein (e.g., SLC4A11-, OC2-, MYC-, RELB-, LIF-, NFKB2-, FOSL2-, ATF4-, or YAP-specific inhibitory nucleic acid or an immunotherapeutic agent comprising an antibody or antigen binding fragment that specifically binds to SLC4A11) will prevent or delay the onset of one or more of the following symptoms: incessant coughing, chest pain, shortness of breath, wheezing, coughing up blood, chronic fatigue, weight loss with no known cause, repeated bouts of pneumonia and swollen or enlarged lymph nodes (glands) inside the chest in the area between the lungs. In certain embodiments, lung cancer subjects exhibiting HPCS that are treated with any of the therapeutic agents of the present technology will show SLC4A11, OC2, MYC, RELB, LIF, NFKB2, FOSL2, ATF4, and/or YAP expression levels that resemble those observed in healthy control subjects.

For therapeutic and/or prophylactic applications, a composition comprising an immunotherapeutic agent comprising an antibody or antigen binding fragment that specifically binds to SLC4A11, or a SLC4A11-, OC2-, MYC-, RELB-, LIF-, NFKB2-, FOSL2-, ATF4-, or YAP-specific inhibitory nucleic acid disclosed herein, is administered to the subject. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered one, two, three, four, or five times per day. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered more than five times per day. Additionally or alternatively, in some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered every day, every other day, every third day, every fourth day, every fifth day, or every sixth day. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered weekly, bi-weekly, tri-weekly, or monthly. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered for a period of one, two, three, four, or five weeks. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered for six weeks or more. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered for twelve weeks or more. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered for a period of less than one year. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered for a period of more than one year. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered throughout the subject's life.

In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 1 week or more. In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 2 weeks or more. In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 3 weeks or more. In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 4 weeks or more. In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 6 weeks or more. In some embodiments of the methods of the present technology, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily for 12 weeks or more. In some embodiments, the immunotherapeutic agent comprising an antibody or antigen binding fragment that specifically binds to SLC4A11, or the SLC4A11-, OC2-, MYC-, RELB-, LIF-, NFKB2-, FOSL2-, ATF4-, or YAP-specific inhibitory nucleic acid is administered daily throughout the subject's life.

Determination of the Biological Effect of the Therapeutic Agents of the Present Technology In various embodiments, suitable in vitro or in vivo assays are performed to determine the effect of a specific therapeutic agent of the present technology (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) and whether its administration is indicated for treatment. In various embodiments, in vitro assays can be performed with representative animal models, to determine if a given therapeutic agent exerts the desired effect on reducing or eliminating signs of HPCS in lung cancer. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more therapeutic agents (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP).

Animal models of lung cancer (e.g., Kras$^{G12D/+}$ p53$^{\Delta/\Delta}$) may be generated using techniques known in the art. Such models may be used to demonstrate the biological effect of therapeutic agents (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) in the prevention and treatment of HPCS in lung cancer, and for determining what comprises a therapeutically effective amount of the one or more therapeutic agents disclosed herein in a given context.

Modes of Administration and Effective Dosages

Any method known to those in the art for contacting a cell, organ or tissue with one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be employed. Suitable methods include in vitro, ex vivo, or in vivo methods. In vivo methods typically include the administration of one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) to a mammal, suitably a human. When used in vivo for therapy, the one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) are administered to the subject in effective amounts (i.e., amounts that have desired therapeutic effect). The dose and dosage regimen will depend upon the degree of the disease state of the subject, the characteristics of the particular therapeutic agent used (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP), e.g., its therapeutic index, and the subject's history.

The effective amount may be determined during preclinical trials and clinical trials by methods familiar to physicians and clinicians. An effective amount of one or more therapeutic agents (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) useful in the methods may be administered to a mammal in need thereof by any of a number of well-known methods for administering pharmaceutical compounds. The therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be administered systemically or locally.

The one or more therapeutic agents described herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) can be incorporated into pharmaceutical compositions for administration, singly or in combination, to a subject for the treatment or prevention of HPCS in lung cancer. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.,* 33:337-462 (1988); Anselem, et al., *Liposome Technology,* CRC Press (1993)). Liposomal formulations can delay clearance and increase cellular uptake (See Reddy, *Ann. Pharmacother.,* 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly a-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems,"*Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more therapeutic agent (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) concentrations in a carrier range from 0.2 to 2000 micrograms per delivered milliliter An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more therapeutic agents (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, one or more of the therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be combined with one or more additional therapies for the prevention or treatment of HPCS in lung cancer. Additional therapeutic agents include, but are not limited to, chemotherapeutic agents, immune checkpoint inhibitors, antibody drug conjugates, immunomodulating/stimulating antibodies, tumor specific monoclonal antibodies (e.g., daratumumab, trastuzumab), radiation therapy, cell-mediated immunotherapy, anti-cancer nucleic acids or proteins, anti-cancer viruses or microorganisms, and any combinations thereof.

In some embodiments, the one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be separately, sequentially or simultaneously administered with at least one additional therapeutic agent selected from the group consisting of alkylating agents, topoisomerase inhibitors, endoplasmic reticulum stress inducing agents, antimetabolites, mitotic inhibitors, nitrogen mustards, nitrosoureas, alkylsulfonates, platinum agents, taxanes, vinca agents, anti-estrogen drugs, aromatase inhibitors, ovarian suppression agents, VEGF/VEGFR inhibitors, EGFR-tyrosine kinase inhibitors, phosphatidylinositol 3-kinase/protein kinase B (PI3K/Akt) inhibitors, PARP inhibitors, cytostatic alkaloids, cytotoxic antibiotics, antimetabolites, endocrine/hormonal agents, bisphosphonate therapy agents, phenphormin and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent.

Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacrine, etoposide phosphate, teniposide, azacitidine (Vidaza), decitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, axitinib, dasatinib, imatinib, nilotinib, pazopanib, sunitinib, or combinations thereof.

Examples of antimetabolites include 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof.

Examples of taxanes include accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, and mixtures thereof.

Examples of DNA alkylating agents include cyclophosphamide, chlorambucil, melphalan, bendamustine, uramustine, estramustine, carmustine, lomustine, nimustine, ranimustine, streptozotocin; busulfan, mannosulfan, and mixtures thereof.

Examples of topoisomerase I inhibitor include SN-38, ARC, NPC, camptothecin, topotecan, 9-nitrocamptothecin, exatecan, lurtotecan, lamellarin D9-aminocamptothecin, rubifen, gimatecan, diflomotecan, BN80927, DX-8951f, MAG-CPT, and mixtures thereof. Examples of topoisomerase II inhibitors include amsacrine, etoposide, etoposide phosphate, teniposide, daunorubicin, mitoxantrone, amsacrine, ellipticines, aurintricarboxylic acid, doxorubicin, and HU-331 and combinations thereof.

Examples of EGFR-tyrosine kinase inhibitors include, but are not limited to, gefitinib, erlotinib, PKI-166, GW-572016, Canertinib, EKB-569, ZD6474 and lapatinib, Examples of PI3K/Akt inhibitors include, but are not limited to, alpelisib, AMG319, apitolisib, AZD8186, BKM120, BGT226, bimiralisib, buparlisib, CH5132799, copanlisib, CUDC-907, dactolisisb, duvelisib, GDC-0941, GDC-0084, gedatolisib, GSK2292767, GSK2636771, idelalisib, IPI-549, leniolisib, LY294002, LY3023414, nemiralisib, omipalisib, PF-04691502, pictilisib, pilaralisib, PX866, RV-1729, SAR260301, SAR245408, serabelisib, SF1126, sonolisib, taselisib, umbralisib, voxtalisib, VS-5584, wortmannin, WX-037, ZSTK474, MK-2206, A-674563, A-443654, acetoxy-tirucallic acid, 3α- and 3β-acetoxy-tirucallic acids, afuresertib (GSK2110183), 4-amino-pyrido[2,3-d]pyrimidine derivative API-1,3-aminopyrrolidine, anilinotriazole derivatives, ARQ751, ARQ 092, AT7867, AT13148, 7-azaindole, AZD5363, (−)-balanol derivatives, BAY 1125976, Boc-Phe-vinyl ketone, CCT128930, 3-chloroacetylindole, diethyl 6-methoxy-5,7-dihydroindolo [2,3-b]carbazole-2,10-dicarboxylate, diindolylmethane, 2,3-diphenylquinoxaline derivatives, DM-PIT-1, edelfosine, erucylphosphocholine, erufosine, frenolicin B, GSK-2141795, GSK690693, H-8, H-89, 4-hydroxynonenal, ilmofosine, imidazo-1,2-pyridine derivatives, indole-3-carbinol, ipatasertib, kalafungin, lactoquinomycin, medermycin, 3-methyl-xanthine, miltefosine, 1,6-naphthyridinone derivatives, NL-71-101, N-[(1-methyl-1H-pyrazol-4-yl)carbonyl]-N'-(3-bromophenyl)-thiourea, OSU-A9, perifosine, 3-oxo-tirucallic acid, PH-316, 3-phenyl-3H-imidazo[4,5-b]pyridine derivatives, 6-phenylpurine derivatives, PHT-427, PIT-1, PIT-2,2-pyrimidyl-5-amidothiophene derivative, pyrrolo[2,3-d]pyrimidine derivatives, quinoline-4-carboxamide, 2-[4-(cyclohexa-1,3-dien-1-yl)-1H-pyrazol-3-yl]phenol, spiroindoline derivatives, triazolo[3,4-f][1,6]naphthyridin-3(2H)-one derivative, triciribine, triciribine mono-phosphate active analogue, and uprosertib.

Additionally or alternatively, in some embodiments, the therapeutic agents of the present technology (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP) may be separately, sequentially or simultaneously administered with at least one additional immuno-modulating/stimulating antibody including but not limited to anti-PD-1/anti-PD-L1 antibody (e.g., pembrolizumab, nivolumab, cemiplimab, atezolizumab, dostarlimab, durvalumab, avelumab, Envafolimab, BMS-936559, CK-301, CD-1001, SHR-1316, CBT-502, BGB-A333), anti-PD-L2 antibody, anti-CTLA-4 antibody, anti-TIM3 antibody, anti-4-1BB antibody, anti-CD73 antibody, anti-GITR antibody, and anti-LAG-3 antibody.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits for the prevention and/or treatment of HPCS in lung cancer comprising one or more therapeutic agents disclosed herein (e.g., an immunotherapeutic agent comprising an antibody or antigen binding fragment that specifically binds to SLC4A11 or inhibitory nucleic acids that specifically target one or more genes selected from among SLC4A11, OC2, MYC, RELB, LIF, NFKB2, FOSL2, ATF4, and YAP). In some embodiments, the kits comprise a nucleic acid sequence selected from the group consisting of SEQ ID NOs: 3, 5-9, 11-13 or any complement thereof. Optionally, the above described components of the kits of the present technology are packed in suitable containers and labeled for the prevention and/or treatment of HPCS in lung cancer.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way.

Example 1: Materials and Methods

In situ Hybridization. Single-molecule mRNA in situ hybridization was performed on formalin-fixed paraffin embedded tissues using RNAscope® 2.5 HD Detection Kit (catalog #322360; Advanced Cell Diagnostics, Newark, Calif.) per the manufacturer's instructions. Protease digestion times were 30 minutes for human LUAD tumor tissues. Freshly cut 4 μm paraffin sections were stained using probe RNAscope® Probe-Hs-SLC4A11 (catalog #583931; Advanced Cell Diagnostics, Newark, Calif.).

Figure 2:
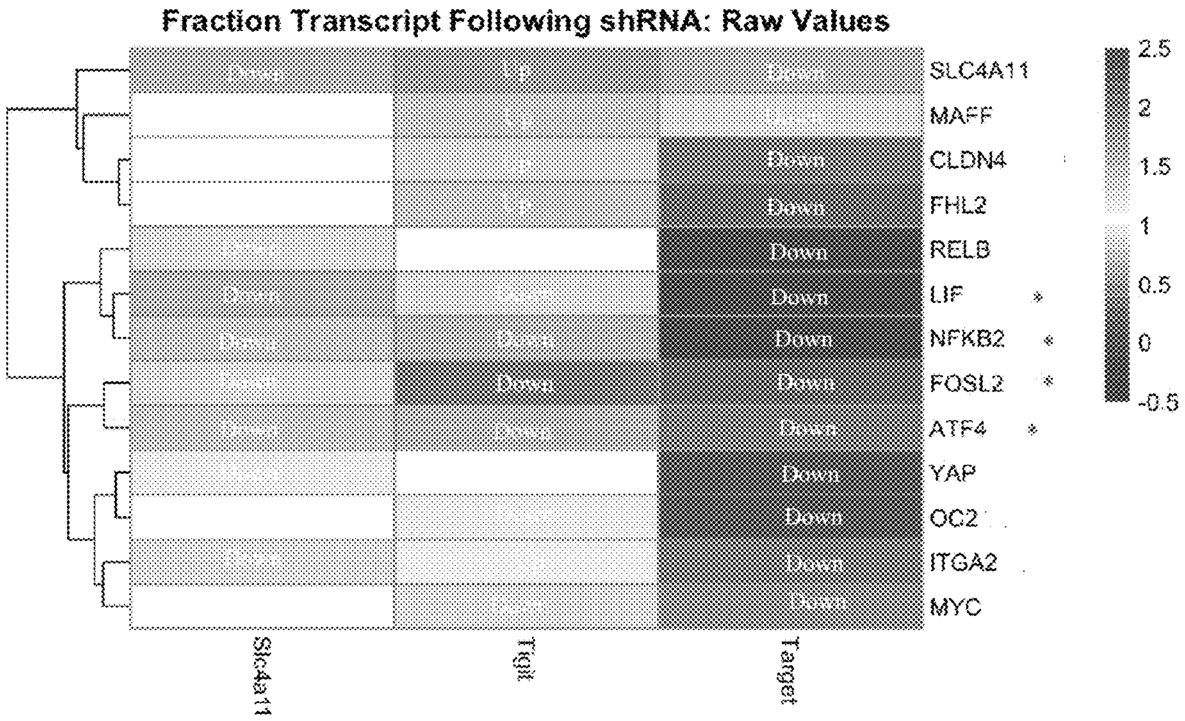
FIG. 2 highlights transcription factors controlling high-plasticity cell state (HPCS) markers Tigit and Slc4a11. $Kras^{G12D/+}$ $p53^{\Delta/\Delta}$ (KP) mouse lung cancer cells were transduced with an "all-in-one" lentiviral vector harboring a doxycycline-inducible short hairpin RNA (shRNA) targeting a candidate gene of interest ("Target" in the heat map) as well as a puromycin resistance gene. Cells were selected in puromycin for 5 days, followed by incubation in doxycycline to induce shRNA expression and target repression. The drop in shRNA target gene levels is represented in the right-most column. The columns on the left and in the middle show levels of Slc4a11 and Tigit gene expression. These genes are markers of HPCS. Candidates that suppress both marker genes (red asterisks) are particularly interesting because these candidates are more likely to impact the cell state as a whole. OC2=Onecut2.
Figure 4A:
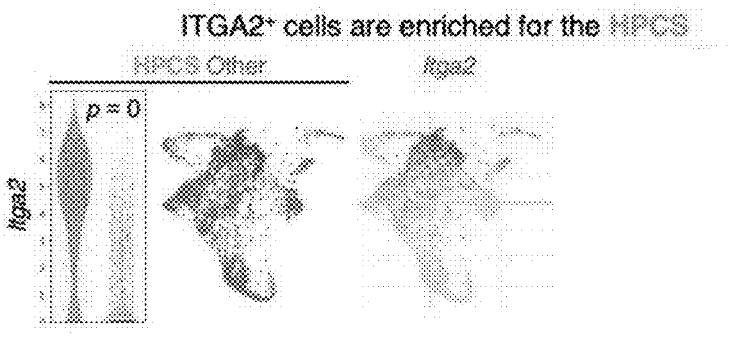
FIGS. 4A-4D show MYC and ONECUT2 activity in the HPCS.
Figure 4B:
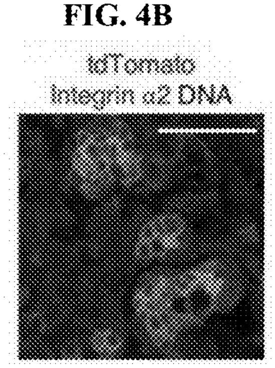
Figure 4C:
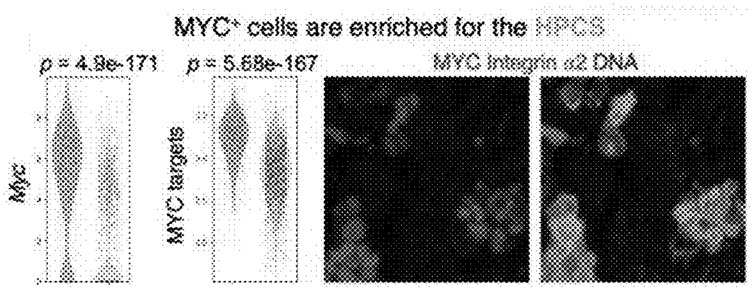
Figure 4D:
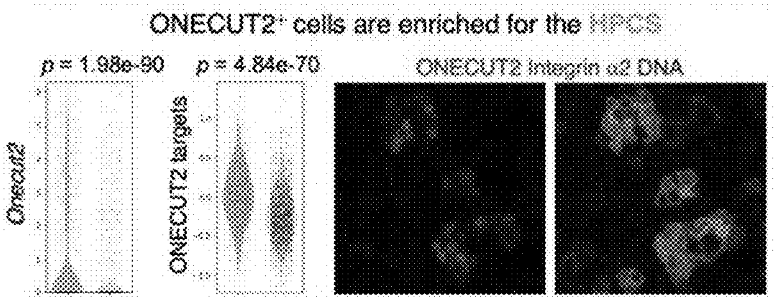

Expression of Dox-inducible shRNA in a $Kras^{G12D/+}$ (KP) LUAD cell line with HPCS features. Mouse KP lung cancer cells were transduced with an "all-in-one" lentiviral vector harboring a doxycycline-inducible short hairpin RNA (shRNA) targeting a candidate gene of interest ("Target" in the heat map; FIG. 2) as well as a puromycin resistance gene. Cells were selected in puromycin for 5 days, followed by incubation in doxycycline for 48 hours to induce shRNA expression and target repression. The sequences of the target-specific shRNAs is shown in FIG. 3.

Figure 1B:
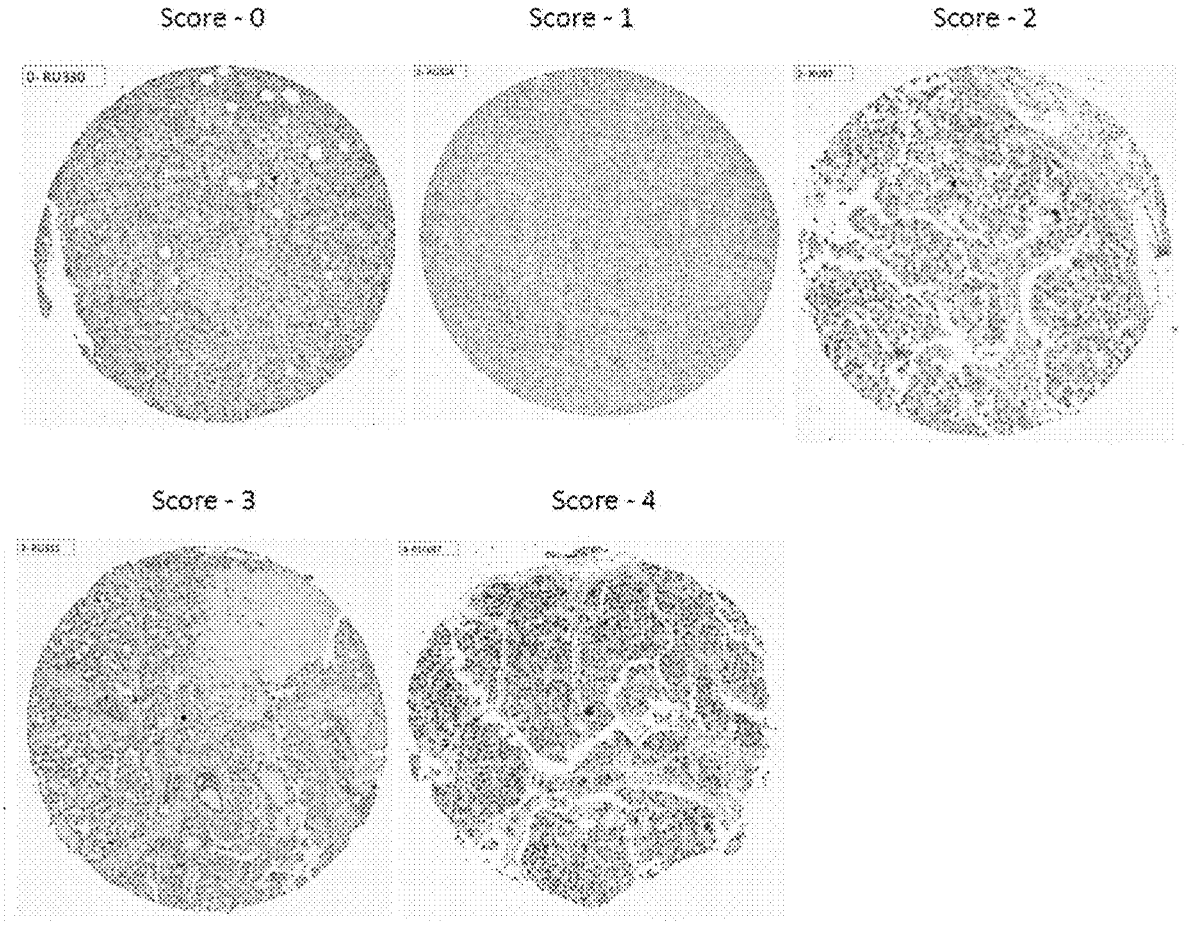

Example 2: Identification of Biomarkers for HPCS in Human Lung Adenocarcinomas and Transcription Factors Regulating the Same FIGS. 1A-B show that SLC4A11 is expressed in a subset of cells in a majority of human lung adenocarcinomas (LUAD), and thus can be exploited as a biomarker for HPCS in LUAD.

FIG. 2 reveals that inhibition of transcription factors RELB Proto-Oncogene, NF-KB Subunit (RELB), Leukemia Inhibitory Factor (LIF), Nuclear Factor Kappa B Subunit 2 (NFKB2), FOS Like 2, AP-1 Transcription Factor Subunit (FOSL2), Activating transcription factor 4 (ATF4), Yes Associated Protein 1 (YAP) reduced the expression of SLC4A11 in KP LUAD cells that exhibit HPCS features. Further, LIF, NFKB2, FOSL2, and ATF4 also downregulated expression levels of Tigit, another biomarker of HPCS. OC2 and MYC transcription factors reduced Tigit expression, but had no effect on SLC4A11 expression.

Example 3: Targeting HPCS in LUAD by Eliminating SLC4A11 Expressing Cells Inhibits Tumor Progression LSL-KrasG12D;p53lox/lox mice will be treated with one or more anti-SLC4A11 immunotherapeutic agents (e.g., antibody drug conjugates, Bi-specific T-cell engagers (BiTEs), CAR T cells, tri-specific natural killer cell engagers (TriNKETs)) at varying doses. The anti-SLC4A11 immunotherapeutic agents may be derived from commercially available SLC4A11 antibodies (e.g., PA5-19207 (Thermo Fisher Scientific, Waltham Mass.), ABN1718 (MilliporeSigma, Burlington Mass.).

For in vitro treatment experiments, anti-tumor efficacy of the above mentioned immunotherapeutic agents will be evaluated in human and mouse lung cancer cell lines or organoids systems.

It is anticipated that the $Kras^{G12D/+}$ mice that are treated with one or more of the immunotherapeutic agents will exhibit reduced tumor progression and/or improved survival compared to untreated $Kras^{G12D/+}$ $p53^{\Delta/\Delta}$ control animals.

Example 4: MYC and ONECUT2 are Candidate Drivers of the HPCS

Figure 5A:
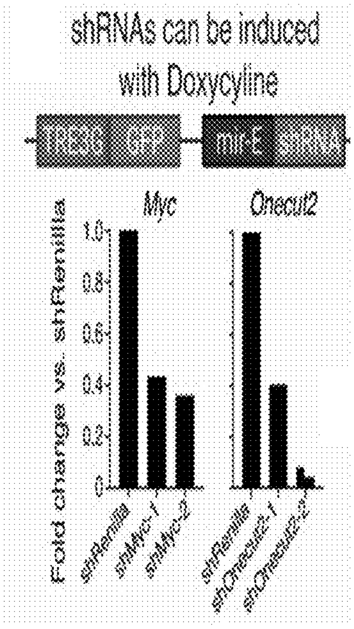
FIGS. 5A-5C show MYC and ONECUT2 functional experiments. All cell lines contained an endogenous rtTA3.
Figure 5B:
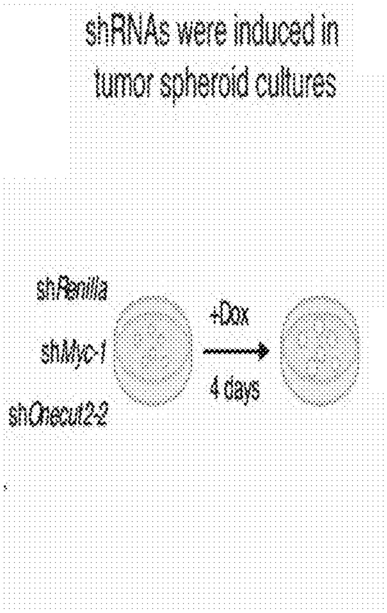
Figure 5C:
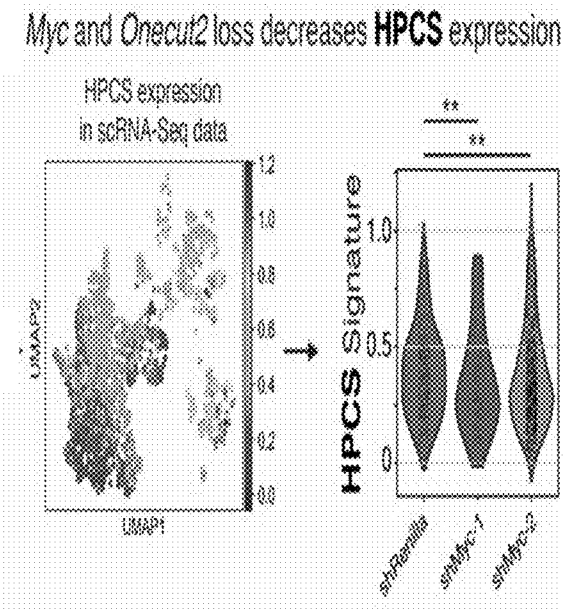

By analyzing two orthogonal KP LUAD datasets via SCENIC analysis (Aibar, S. et al., *Nat. Methods* (2017), doi:10.1038/nmeth.4463; Van de Sande, B. et al., *Nat. Protoc.* 157:15, 2247-2276 (2020)) and performing a custom integrated analysis of mouse and human LUAD gene expression modules (Marjanovic et al., *Cancer Cell* 38,229-246 (2020); Zhang, X. et al., *Nucleic Acids Res.* (2019), doi:10.1093/nar/gky900; Subramanian, A. et al., *Proc. Natl. Acad. Sci. U.S.A.* (2005) doi:10.1073/pnas.0506580102) with the mSigDB (Liberzon, A. et al., *Bioinformatics* 27, 1739-1740 (2011); Liberzon, A. et al., *Cell Syst.* (2015), doi:10.1016/j.cels.2015.12.004), MYC and ONECUT2 were identified as putative drivers of the HPCS in lung cancer. Both MYC and ONECUT2 exhibit high concordance with the HPCS and colocalize with integrin α2, a surface marker for the HPCS (FIGS. 4A-4D). To test the functional role of MYC and ONECUT2 in the HPCS, a set of inducible shRNA hairpins targeting Myc and Onecut2 were designed and tested using an in vitro KP LUAD cell line containing a third-generation reverse tetracycline-controlled transactivator (rtTA3) (Das, A. T. et al., *J. Biol. Chem.* 279, 18776-18782 (2004)) (FIG. 5A). Tumor spheroids with endogenous rtTA3 and inducible shRNA hairpins against Myc, Onecut2, or Renilla (control) were placed on doxycycline for 4 days and then harvested for scRNA-Seq analysis. Suppression of Myc or Onecut2 decreased the expression of the HPCS relative to control (FIGS. 5B-5C).

Example 5 In Vivo Perturb-Seq Experiments

Figure 6G:
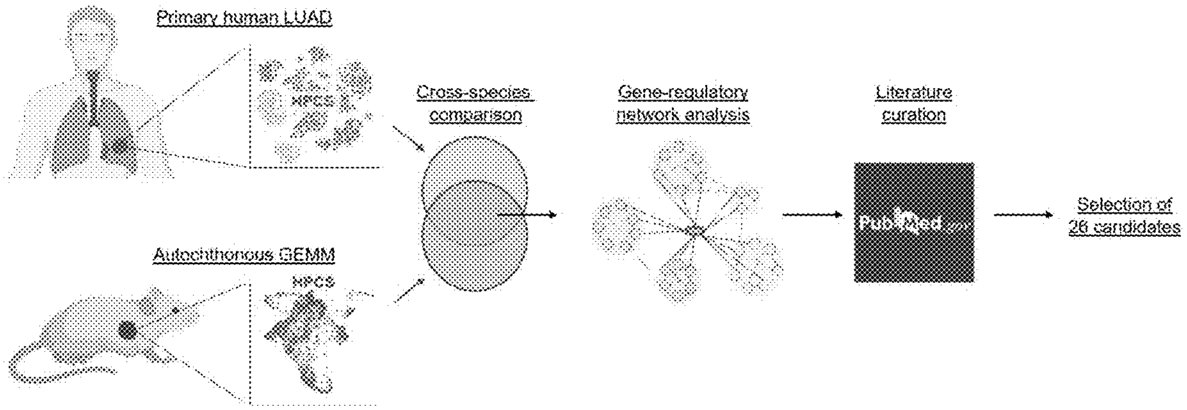
FIG. 6G depicts strategy for identification of drivers of the HPCS.

FIG. 6G depicts strategy for identification of drivers of the HPCS in lung cancer. Genes of interest were identified using SCENIC analysis on two orthogonal KP LUAD datasets as well as by manual curation. A series of vectors, each containing a doxycycline-inducible promoter linked to a GFP and specific mir-E promoted shRNA to a gene of interest were constructed. Each of the vectors contained a Cre recombinase (FIG. 6A), as well as a degenerate molecular barcode and an shRNA-specific barcode (FIG. 6B). For controls, shRNAs targeting shRenilla as well as an empty vector shRNA were used. A library of viruses for each shRNA-specific vector was constructed using standard methods and then each viral library was tittered using a KP LUAD cell line. The viruses were then pooled together at equititer and a cell line was infected with two concentrations of the viral mix. DNA was obtained from the infected progeny and custom PCR primers were used to amplify the degenerate molecular barcodes. The PCR amplicons were gel-purified and then sequenced by Next-Generation Sequencing. Counts of the amplicons were then analyzed to determine the level or representation for each shRNA-specific virus. ShRNA-specific viruses were then pooled again based on empiric infection levels in the cell lines before being used for in vivo experiments.

Figure 6H:
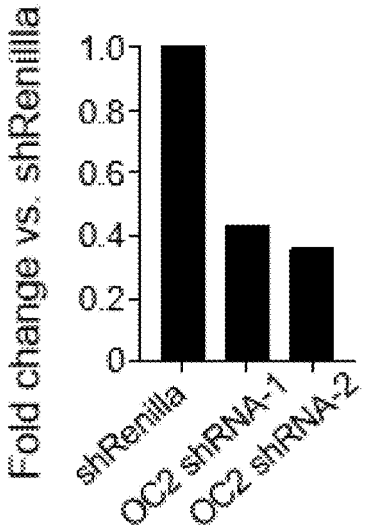
FIG. 6H demonstrates that knockdown of OC2 results in loss of HPCS.

A total of 30 KP-RIK (FIG. 6C) mice were infected through intratracheal inhalation of pooled lentivirus comprising the shRNA constructs of FIG. 6A at 25k TU/μl (FIG. 6D). 5 mice were used as controls to harvest tissue for DNA sequencing without doxycycline exposure. At ~16 weeks post infection, the rest of the mice received intraperitoneal injections of 50 mg/kg Doxycycline and placed on Doxycycline feed. About 1 week (final time TBD) after doxycycline induction, tumors were harvested from the lungs of the remaining 25 mice. Using a dissection microscope, about 100 GFP+/RIK+ roughly equal sized tumors (FIG. 6E) were plucked, pooled, and dissociated into single cell suspension using a mixture of Dispase II/Collagenase Type IV/Dnase I. Cells were stained with flow antibodies and FACS sorted for Live/$CD45^-$/$CD31^-$/$TER\text{-}119^-$/$CD11b^-$/$CD11c^-$/$mKate2^+$/$GFP^+$ tumor cells (FIG. 6F) and 10× Chromium droplet-based sequencing was performed. Barcoded sequences were demultiplexed using a custom software pipeline written in Python and were made compatible with analysis with SCANPY to determine levels of tumors arising from specific shRNA constructs. ScRNA-Seq data was analyzed from each shRNA construct and compared against prior cell state classifications. Under this screen, shRNA constructs against genes important for the HPCS are expected to have lower representation compared to shRNA constructs with no effect and the control shRNA sequences. The results demonstrate that ONECUT2 is a driver of HPCS in vivo in LUAD (FIG. 6H).

STATEMENT OF SUPPORT

This invention was made in part with a grant from the Rita Allen Foundation.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIG.s and tables, to the extent they are not inconsistent with the explicit teachings of this specification.

The invention claimed is:

1. A method for inhibiting high-plasticity cell state (HPCS) in heterogeneous lung tumors in a patient in need thereof comprising administering to the patient an effective amount of monotherapy with an inhibitory nucleic acid, wherein the inhibitory nucleic acid specifically hybridizes to RELB, LIF, NFKB2, FOSL2, ATF4, or OC2, wherein the inhibitory nucleic acid is a siRNA, an antisense nucleic acid, a shRNA, a sgRNA, or a ribozyme, and wherein the heterogeneous lung tumors comprise Integrin α2-and SLC4A11-expressing HPCS tumor cells.

2. The method of claim 1, wherein the inhibitory nucleic acid comprises a nucleic acid sequence selected from the group consisting of: SEQ ID NO: 5, SEQ ID NO: 6, SEQ ID NO: 7, SEQ ID NO: 8, SEQ ID NO: 9, SEQ ID NO: 13, or a complement thereof.

3. The method of claim 1, wherein the patient displays elevated expression levels of OC2, MYC, RELB, LIF, NFKB2, FOSL2, ATF4, and/or YAP protein in lung tumor cells prior to treatment.

4. The method of claim 1, further comprising detecting HPCS in the heterogeneous lung tumors by detecting the presence of Integrin α2-and SLC4A11-expressing tumor cells.

5. The method of claim 1, wherein the patient is diagnosed with or at risk for non-small cell lung cancer (NSCLC).

6. The method of claim 5, wherein the NSCLC is lung adenocarcinoma (LUAD), squamous cell carcinoma (SCC), or large cell carcinoma.

7. The method of claim 1, wherein the signs or symptoms of lung cancer comprise one or more of incessant coughing, chest pain, shortness of breath, wheezing, coughing up blood, chronic fatigue, weight loss with no known cause, repeated bouts of pneumonia, and swollen or enlarged lymph nodes (glands) inside chest area between the lungs.

8. The method of claim 1, wherein the patient harbors one or more mutations in KRAS, BRAF, P53, EGFR, PIK3CA, HER2, DDR2, PIK3CA, PTEN or H3F3A.

9. The method of claim 1, wherein the patient harbors one or more gene amplifications in MET, HER2, FGFRI, or PDGFRA, and/or one or more gene rearrangements in ALK, NTRK, NRGI, ROSI, or RET.

10. The method of claim 1, wherein the inhibitory nucleic acid is administered orally, topically, intranasally, systemically, intravenously, subcutaneously, intraperitoneally, intradermally, intraocularly, iontophoretically, transmucosally, or intramuscularly.

11. A method for reducing tumorigenic potential in heterogenous lung tumors in a patient in need thereof comprising administering to the patient an effective amount of monotherapy with an inhibitory nucleic acid, wherein the inhibitory nucleic acid specifically hybridizes to RELB, LIF, NFKB2, FOSL2, ATF4, or OC2, wherein the inhibitory nucleic acid is a siRNA, an antisense nucleic acid, a shRNA, a sgRNA, or a ribozyme, and wherein the heterogeneous lung tumors comprise Integrin α2-and SLC4A11-expressing HPCS tumor cells.

* * * * *

SEQUENCE LISTING

<160> NUMBER OF SEQ ID NOS: 30

<210> SEQ ID NO 1
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tgctgttgac agtgagcgac agcgtcatca ccatcgtcaa tagtgaagcc acagatgtat 60
tgacgatggt gatgacgctg gtgcctactg cctcgga 97

<210> SEQ ID NO 2
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tgctgttgac agtgagcgat acccgcaaga tggaatacaa tagtgaagcc acagatgtat 60
tgtattccat cttgcgggta ctgcctactg cctcgga 97

<210> SEQ ID NO 3
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
tgctgttgac agtgagcgat cgcaagtatc tgaaattgaa tagtgaagcc acagatgtat 60
tcaatttcag atacttgcga gtgcctactg cctcgga 97

<210> SEQ ID NO 4
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
tgctgttgac agtgagcgac tcgtggatgt tgtagttgta tagtgaagcc acagatgtat 60
acaactacaa catccacgag gtgcctactg cctcgga 97

<210> SEQ ID NO 5
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tgctgttgac agtgagcgac aggaccacag atgaattgga tagtgaagcc acagatgtat 60
ccaattcatc tgtggtcctg gtgcctactg cctcgga 97

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tgctgttgac agtgagcgcg acaggtagca taaagtagaa tagtgaagcc acagatgtat 60
tctactttat gctacctgtc ttgcctactg cctcgga 97

<210> SEQ ID NO 7
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tgctgttgac agtgagcgac agagatatgg acaattgcta tagtgaagcc acagatgtat 60
agcaattgtc catatctctg gtgcctactg cctcgga 97

<210> SEQ ID NO 8
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
tgctgttgac agtgagcgac agaaggagaa ggagaagcta tagtgaagcc acagatgtat 60
agcttctcct tctccttctg ctgcctactg cctcgga 97

```
<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

tgctgttgac agtgagcgat ggagttagtt tgacagctaa tagtgaagcc acagatgtat     60

tagctgtcaa actaactcca gtgcctactg cctcgga                              97


<210> SEQ ID NO 10
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

tgctgttgac agtgagcgca acccggactg tgcaaagtta tagtgaagcc acagatgtat     60

aactttgcac agtccgggtt ttgcctactg cctcgga                              97


<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

tgctgttgac agtgagcgcc gacgagacct tcatcaagaa tagtgaagcc acagatgtat     60

tcttgatgaa ggtctcgtcg ttgcctactg cctcgga                              97


<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

tgctgttgac agtgagcgcc acaacgatca gacaacaaca tagtgaagcc acagatgtat     60

gttgttgtct gatcgttgtg atgcctactg cctcgga                              97


<210> SEQ ID NO 13
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

tgctgttgac agtgagcgac acaacgaaga tatacagaaa tagtgaagcc acagatgtat     60

ttctgtatat cttcgttgtg ctgcctactg cctcgga                              97


<210> SEQ ID NO 14
<211> LENGTH: 97
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 14

```
tgctgttgac agtgagcgca ggaattataa tgcttatcta tagtgaagcc acagatgtat     60

agataagcat tataattcct atgcctactg cctcgga                              97
```

<210> SEQ ID NO 15
<211> LENGTH: 3245
<212> TYPE: DNA
<213> ORGANISM: Homo sapiens

<400> SEQUENCE: 15

```
cttttggacc aacggctctg gcttccaggc ggccgggacg cggtcccagg actggagacc     60

gttgcctgtc ggcccccgtg tgacccgggg cgcgtgacgg gggtcggggg aactgcgcct    120

gcaatgggcg tttatggccc ccaggaccgg tctgagagtg agaagaggga tgtgcagaga    180

gatcccccgc cttggcatcc gaggagagag ggggagaggc ccgctcgggc ccggtccctt    240

cctctcgctg cagcggggca gggttttctc aggaaaacct ggattagcga acatgaaaac    300

tctcccacca tgtcgcagaa tggatacttc gaggattcaa gctactacaa gtgtgacaca    360

gatgacacct tcgaagcccg agaggagatc ctgggggatg aggccttcga cactgccaac    420

tcctccatcg tgtctggcga gagtatccgt ttttttgtca atgtcaacct tgagatgcag    480

gccaccaaca ctgagaatga agcgacttcc ggtggctgtg tgctcctgca cacctcccga    540

aagtacctga agttaaagaa cttcaaggaa gagatccgtg cgcaccgcga cctagatggc    600

ttcctggcgc aggccagcat cgtcctgaac gagacggcca cctccctgga taacgtgctg    660

cggaccatgc ttcgccgctt cgccagggac cctgacaaca atgagcccaa ctgcaacctg    720

gacctgctca tggccatgct cttcaccgat gccggggcac ccatgcgggg taaagtccac    780

ctgctgtcag ataccatcca aggggtcacc gccacagtga caggggtgcg gtaccagcag    840

tcgtggctct gcatcatctg taccatgaag gccctacaga agcggcacgt gtgcatcagc    900

cgcctggttc gcccacagaa ctgggggggag aattcctgtg aggttcggtt cgtcatcctg    960

gtgctggccc cacccaagat gaaaagcact aagactgcga tggaggtggc gcgcacgttt   1020

gccaccatgt tctcggatat cgccttccgc cagaagctcc tggagacccg cacagaggag   1080

gaattcaagg aggccttggt gcatcagaga cagctgctca ccatggtgag ccacggtcca   1140

gtggcgccga gaacgaagga acgcagcaca gtctccctcc ctgcccacag acacccagag   1200

cccccaaagt gcaaggactt tgtccctttt gggaagggca tccgggagga catcgcacgc   1260

aggttcccct tgtacccctt ggacttcact gatggcatta ttgggaaaaa caaggctgtg   1320

ggcaaataca tcaccaccac cctgttcctc tacttcgcct gcctcctgcc caccatcgct   1380

ttcgggtctc tcaatgacga gaacacagac ggggccatcg acgtgcagaa gaccatagcc   1440

gggcagagca tcgggggcct gctctacgcg ctcttctctg ggcagccatt ggtgattctg   1500

ctgaccaccg cgcccctggc gctctacatc caggtgattc gtgtcatctg tgatgactat   1560

gacctggact tcaactcctt ctacgcatgg acgggcctgt ggaatagttt cttccttgcg   1620

ctttatgcct tttcaacct cagcctggtc atgagtctct tcaagaggtc gacggaggag    1680

atcatcgccc tcttcatttc catcacgttt gtgctggatg ccgtcaaggg cacggttaaa   1740

atcttctgga agtactacta tgggcattac ttggacgact atcacacaaa aaggacttca   1800

tcccttgtca gcctgtcagg cctcggcgcc agcctcaacg ccagcctcca cactgccctc   1860
```

```
aacgccagct tcctcgccag ccccacggag ctgccctcgg ccacacactc aggccaggcg   1920

accgccgtgc tcagcctcct catcatgctg ggcacgctct ggctgggcta caccctctac   1980

caattcaaga agagccccta cctgcacccc tgcgtgcgag agatcctgtc cgactgcgcc   2040

ctgcccatcg cggtgctcgc cttctccctc atcagctccc atggcttccg ggaaatcgag   2100

atgagcaagt tccgctacaa ccccagcgag agcccctttg cgatggcgca gatccagtcg   2160

ctgtccctga gggccgtcag cggtgccatg ggcctcggct tcctgctgtc catgctcttc   2220

ttcatcgagc agaacttggt ggccgccttg gtgaatgcac cggagaacag gctggtgaag   2280

ggcactgcct accactggga cctcctgctc ctcgccatca tcaacacagg gctgtctctg   2340

tttgggctgc cttggatcca tgccgcctac ccccactccc cgctgcacgt gcgagccctg   2400

gccttagtgg aggagcgtgt ggagaacgga cacatctatg acacgattgt gaacgtgaag   2460

gagacgcggc tgacctcgct gggcgccagc gtcctggtgg gcctgtccct gttgctgctg   2520

ccggtcccgc ttcagtggat ccccaagccc gtgctctatg gcctcttcct ctacatcgcg   2580

ctcacctccc tcgatggcaa ccagctcgtc cagcgcgtgg ccctgctgct caaggagcag   2640

actgcgtacc ccccgacaca ctacatccgg agggtgcccc agaggaagat ccactacttc   2700

acgggcctgc aggtgcttca gctgctgctg ctgtgtgcct tcggcatgag ctccctgccc   2760

tacatgaaga tgatctttcc cctcatcatg atcgccatga tccccatccg ctatatcctg   2820

ctgccccgaa tcattgaagc caagtacttg gatgtcatgg acgctgagca caggccttga   2880

ctggcagacc ctgcccacgc cccattcgcc agccctccac gtcctcccag gctggctctg   2940

gagctgtgag ggaggtgta ggtgtgtggg tgactgctct gtgctgcgcc ttctcatggc   3000

tgactcaggc ctggggcatc tgggcattgt aggggtgcag tggtatgtgc ccacccctct   3060

cccattatcc tttagcttta ggccaagagc gttgctcagg gcagcttctg cccagggtgg   3120

gtgggactga gcaggatgga ttttcttttg ataaaagagt cgatgcctga aagagaaacc   3180

atttccttga ttgtgtaagg aacttgctgg acgcacatta gagaataaag ctcctgtttc   3240

taggc                                                               3245
```

```
<210> SEQ ID NO 16
<211> LENGTH: 16433
<212> TYPE: DNA
<213> ORGANISM: Homo sapiens

<400> SEQUENCE: 16

agagcccttc tggacagctc ccgctcaccc aaacagaaga cgtcggcgcc ggagcgggct     60

cggacatggc gaggctgcga gccggcccga gcggcggggc ccggtgatcc ctccctccct    120

ccccgtcccc tcccctctcc cgcacgcacg ccccgtccgc ccccaccccg cccccacccc    180

gggcgagccc gcccgcagcc cggggcgcac acccgcacgc gcactcctct ccactcactc    240

ccgcgcccgc ccccactccc gcagccgagc cccgccacgc gcgccttgcc cgcccgccgg    300

ccgcccccgc cgcccccgcc gcccccgggc cctgatggac tgaatgaagg ctgcctacac    360

cgcctatcga tgcctcacca aagacctaga aggctgcgcc atgaacccgg agctgacaat    420

ggaaagtctg ggcactttgc acgggccggc cggcggcggc agtggcgggg gcggcggcgg    480

gggcggcggg ggcggcggcg ggggcccggg ccatgagcag gagctgctgg ccagccccag    540

cccccaccac gcgggccgcg gcgccgctgg ctcgctgcgg ggccctccgc cgcctccaac    600

cgcgcaccag gagctgggca cggcggcagc ggcggcagcg gcggcgtcgc gctcggccat    660
```

```
ggtcaccagc atggcctcga tcctggacgg cggcgactac cggcccgagc tctccatccc    720
gctgcaccac gccatgagca tgtcctgcga ctcgtctccg cctggcatgg gcatgagcaa    780
cacctacacc acgctgacac cgctccagcc gctgccaccc atctccaccg tgtctgacaa    840
gttccaccac cctcacccgc accaccatcc gcaccaccac caccaccacc accaccagcg    900
cctgtccggc aacgtcagcg gcagcttcac cctcatgcgc gacgagcgcg ggctcccggc    960
catgaacaac ctctacagtc cctacaagga gatgcccggc atgagccaga gcctgtcccc   1020
gctggccgcc acgccgctgg gcaacgggct aggcggcctc cacaacgcgc agcagagtct   1080
gcccaactac ggtccgccgg gccacgacaa aatgctcagc cccaacttcg acgcgcacca   1140
cactgccatg ctgacccgcg gtgagcaaca cctgtcccgc ggcctgggca ccccacctgc   1200
ggccatgatg tcgcacctga acggcctgca ccacccgggc cacactcagt ctcacgggcc   1260
ggtgctggca cccagtcgcg agcggccacc ctcgtcctca tcgggctcgc aggtggccac   1320
gtcgggccag ctggaagaaa tcaacaccaa agaggtggcc cagcgcatca cagcggagct   1380
gaagcgctac agtatccccc aggcgatctt tgcgcagagg gtgctgtgcc ggtctcaggg   1440
gactctctcc gacctgctcc ggaatccaaa accgtggagt aaactcaaat ctggcaggga   1500
gaccttccgc aggatgtgga agtggcttca ggagcccgag ttccagcgca tgtccgcctt   1560
acgcctggca gcgtgcaaac gcaaagagca agaaccaaac aaagacagga acaattccca   1620
gaagaagtcc cgcctggtgt tcactgacct ccaacgccga acactcttcg ccatcttcaa   1680
ggagaacaaa cgcccgtcaa aggagatgca gatcaccatt tcccagcagc tgggcctgga   1740
gctcacaacc gtcagcaact tcttcatgaa cgcccggcgc cgcagcctgg agaagtggca   1800
agacgatctg agcacagggg gctcctcgtc cacctccagc acgtgtacca aagcatgatg   1860
gaaggactct cacttgggca caagtcacct ccaaatgagg acaacagata ccaaaagaaa   1920
acaaaggaaa aagacaccgg attcctagct ggggcccttc actggtgatt tgaaagcaca   1980
attctcttgc aaagaaactt atattctagc tgtaatcata ggccaggtgt tcttcttttg   2040
tttttaatgg ctatggagtc caagtgcaag ctgaaaaatt aatctcttag aaccagacac   2100
tgttctctga gcatgctaag catcccagaa acccaaatgg ggccttcctg gagcgagtta   2160
attccagtat ggtgtcaacc aagctcggga ttgcttaaaa tatcatccat cccacttcag   2220
gtcctgtcag cttcttgcag tcagagttcc tatgagtaac aataggagtt tggcctatgt   2280
aaggactctg agtttaggct tccaagatac aacaataaga gaagaatcta gcaacgagaa   2340
tgacctcatt tgctttccac atgcttagcc tcattatacc atgttatgtc caagttcaca   2400
gccacaacat cagaatggta attactgagc acaagtttta aatatggacg ttaaaaaaaa   2460
aaatccaagg acctgttttt ccaacccaga catcttttca ttgaatgatt tagaaagctt   2520
taagttgatc cagcttacaa ttttttttt ctttacctcc tggaaatctc atatggtctt   2580
ggatccgtca aaaaaaccag tcagttcact tgcgctcaaa gtatcaagca caacaaagat   2640
aaacagaagt gaggaaggtt ctgggttcac tacatctgga ttttcaagac acctattgtg   2700
aagtcattag ggaattgatg agaatatggc ttcaagcaca ttttgcagtt tgctacaaat   2760
tctgttgtac ataatgcaga cgcacactca ggaggccaat ttaactgtta acagtgcatg   2820
gagcgaatgc agcattttaa aagatctagg tttttttagg tcattaatgt gtccttggtt   2880
gatcagtcat ctggtccctc ctactgtgtg ttatgaccac cacgtaatcc attctcgctc   2940
tttctgattt ggggtttttc ctcatccatc ccattagtag ggatgttttc tgtgttttct   3000
agcaagaaaa aaaaatcaat caatcaaacc tgcatacatg ttactcatga ctgtcatcta   3060
```

gtcctaaatc tcttctgttg ttgaatcatc cttgcaaaac agctgaatac atctggagaa 3120
aacacagcac accaaagaag cagaatactg caaaccaaag acatttatga cttgtcattt 3180
tctagcctaa aaatactgtg attactttta gaaatcagaa aacctctgca actccgaatg 3240
gcattcagct cttgcatttg gcgcatcatc gggctgagcg gaccagctac accaaggaca 3300
ttagccaagc cacccagagg ggtggctttg ccacaccagt tgtcaccttc ccatagcaag 3360
tggaagagcg cccacagaac tctgggagat tgcaaaggtc acaatgtgca tatttaccag 3420
tgaatggccc cgggtggggc cacgtggggg tgttcaaagc aagccaaacg ctgcaatcat 3480
tctttacaga cacttgagac tgactttttt atgaattact tagtcgaaac caaagaaact 3540
ttttctgcac ctacttctgc aacaaacaaa actgtcccat taaaatgaat aaataaatcc 3600
gtaaatcaat ggaaatcacc accaataaga aggaagcacg ccagaaaata aacgaaaaca 3660
aaaacaggga gacacactgt gttcaaacag acctcttggg acatttttttg gaagcagatt 3720
ttaaagaaag ggttgagaca aagatagaaa taaggaagag cctcagtggc tgctgcttca 3780
tttgacaact cacacggtaa tcttaaagct gaagattgtc tttaatttgt gcctatgcag 3840
tttttcaaaa gaacacggaa cagagcaaca gaaacctcaa cagctacaat accaaagatg 3900
aggatttctc acacctttg tttcagttca ttatctcctc ttgcctggct aaaatactaa 3960
tagcgccatt gaactgtata aaggtaatca attatgtttc tctgagcaac aaaaggaaag 4020
ggccatttat ttgattttat tgtttcattt caattttgtc ttatggtttt ttgccccaac 4080
atggaatctc tcaaaagttt ccatggactc caagtttaag atgttgggat attgaacagt 4140
tctctctgct cagcagaggg tagggaataa cattatcact tgaatgttct ttgcttaacc 4200
cttagacttg gttccttcta tgttcagagt ctcatcatca ggggaaggaa agggagtgag 4260
ggtcagggat aggggtcttg gtgatgcatc ctctcccgag ccacagaacc aaagagttta 4320
tagaggaatt tacagcctcg ttttcatgtg attgctacat cctaacaggg cttcatttgg 4380
gggtgggggg aaacatgtaa aaataattgc cagtttctac ttttctatta gctttttaaa 4440
aatcagctgt aaagttgcat ttctaaagaa agatatatat aatatataaa atacatatat 4500
agatcaactt gacattggtg ataaccaaaa ttattgctgt ccaaattcat gtcttgtttt 4560
ggtccagtgc ttcatttgct aagtattcgg ttcagaattt ttctcatttc tcatgccatt 4620
ccagagttaa tttgccactg tggatgattt gaagtattca gatctctatg gaagtttctg 4680
ggacaggttt aaagtcaaga tcaagcattt tagcatttaa cctgttgata aatggatcca 4740
tggtgtacat gagttttatt tgtattcgga gtcatctcta ttctatccct cagcctcgat 4800
taaggtggtg agtgaagtgc atccaacaga ctcggcccag aactgggtcc tgacagtggg 4860
gtgctcatct tctgtaactg ttgggaaggc tcggtggtcc attttcacca gttaaagaat 4920
atgaggccag cccagaaatc tgttctccag gagctgccct gtcccatctg ggtgtgccag 4980
accccctcag tgagcaggtc caccaaaggg acttctcaca ggggaagccc aactcctgtt 5040
gcaatgggtt gatagatttc ctcagggtgg taattaccaa ttcgtatttt gacaagccta 5100
tgtgcaacca cagctggcac tggggtgggc agtggtgttg ggtgggatgg gggagagtgt 5160
ctcaatcctg aagagaaaat ataaagcagg ttttggggag acttctggag tcctgcccct 5220
agagagcccc attgttgttc tttgtgcccc ctcctcattc cccctatgtg ggtctcccta 5280
tgcaggagct gtgagagaat gtgactctcc acaattttta taattcatcc ttcctaggag 5340
attgttcatt ggctcttccc ttgtgtccct ttgtcccttg ctcatactcc atgtttcctt 5400

-continued

```
tgtcaaagga ctaagaaaag agcatatttc agcagaggag tgttcccatg tgggttgatt   5460
tcaacttggg tatttctaaa agagtccttg tgacatgtgt ccagtggaaa tggttgctct   5520
tttccagact ggattgagga atggagcctg tttgatttgg ttagtgattc tttgacatac   5580
taatctcagc gtttgggtct ccagcatcct ctgaagatgt ctagactagt agaggctgcc   5640
tttgtgacct gacattacaa cattggtcaa accagtcctc tgataatcag aagaacatgt   5700
cataattgtt taaaaaaaaa aaaaaggcaa gaatttctct ccaaggagct ttaataaatg   5760
tctcattcca gataatgtca taccagagaa aagtgcttgc ttttagaaaa ttatttacat   5820
acatatataa atatatatgt gtatctatac agttatgtat caaaatttta agccctgcag   5880
aatttcaatt tgttagaaat ctaacagaaa aaaatttcta tattgaaagg taatagaatt   5940
taacccagtg agtttactca aggattttta aatttaagtt aataatttca gagaaaataa   6000
ccatttgggt gtggttatag tttagtatcc attacctcaa tccaaggaaa attccaggca   6060
ttcctcaacc atcaggaaaa ggtacagtgt gaaggaacag ttctcagcca aatttcacat   6120
tcttgaggca acagaaatca aaacactcag agccattgag tggaaaaaca atttacttta   6180
ttcctttaca caaataggct tgcattgttt ttgttttaat gtgattttgg tactagggat   6240
ataattattt cattccagga aataataaaa aaaaacagac agagccaata catttctttt   6300
tttaaaggaa acagcaacaa caataaaaac tcagcaccaa tatttaaaag cttttccaaa   6360
atgtaaaaga agtgtttagc ttgcaccatg cataaaggtg caggctagtt gaaccaggaa   6420
gcatggcact tcctctggag aaatccagaa agagttgctt ctaagctccc ttttccccct   6480
gcaggctctt ggcaattgta ggctttagca aatccagaat aattttcaat tcaagctaaa   6540
ataaaatcaa catttggaat gtaaatctga tacacacaca cttttctaag tcaaacaaca   6600
tatttcaaaa ccaaaaataa ataccttta gataatcagt tattttcttt gtctatactg   6660
ggcacccacc tactagtgcc agtaaattca agttgaacag atttttaaaa tcactattat   6720
ctgggtatgg gggaaacttc cccacttttg aaaatgttgg tagaattata ggaatgtctg   6780
tttgattatc attaccaaag tgtcatgaca gtatgccttt gtagtgaact cggattttca   6840
ggagtttgaa tagttggata ttttaaaatc taagaagaaa aggcctgttt ccaatgttgt   6900
tgaagaataa tgaactctat taaaaagtgg agaaaaagat aatacatgtg gtcaaggttg   6960
accacaaggc ccaggcacaa ctaccttggc gataatcttc tagattcgta acaggttaga   7020
gctgactttt tgtttttgtt gttgctgatg ctgtgtgatt cagacttctc agcctaacca   7080
ggaagagtaa gtggaaatgg tagatgaaga aggggtagag ctggtgtatc tataactttc   7140
tgatatttgt ctgccaaact tgatatatta gtaatttttt tatctttagc taagatcaag   7200
tcacccctga aacaacagga gattctagtt ttaaaataag gccacaaaaa tccttacgga   7260
atgaagaatg gcaccccagt tggttgtata agtctcataa gataatgatg ttgattttaa   7320
atatggatgt ctcaatgcct gttttctatc aatgatttgt ttgtttccaa ggtcggggag   7380
ggaaagaggg gagggtttat ctgttttaga aagtctcaga atacttataa aatacagaag   7440
tagttattaa aatatatagg acctcacata ggtagataca gaacttacca ttgaggctga   7500
tgggctgttg tgtgaatcac acaggacctt aaatgaggct cattattctc acacaccaaa   7560
atgactctga cagcctgaag cagttattgc tagagcccaa gctttccttg gaggttttgg   7620
agttaggttg attggaagta accagctaat accttttcta gtggagaaaa agacattgct   7680
accagcttgt tcatcccata gaagtcttcc actctgctcc atttttagca gcaagcattt   7740
catgtagcat aaaccttggc agataagtgt gcctaaggtt tatacagtct gtccgcttgg   7800
```

atgtatacaa atttagatac atattttaac atgtgttctc atagatgact ttataacaac 7860
acacattacc tataggtgtc tagactgtgt acatacaagt gtgtacagac aagcttcata 7920
cgtatatact gtaatccgtt acaacaaata aattttaaat catcgtttaa catgtatgtg 7980
gtacttctac agtgtacatt gttttcatta tttattgtaa cattgaaaac cacagtgcag 8040
ggaaaacaaa agtatcccag catcttcatc ctgtacactt ggaattaatt tcatttgggc 8100
atatccaaga taaactcaac tttcaagaaa tcttgtatat tatttaatca tctgtgttag 8160
gatgacacct atgattgatg acttcggttg aatagcttta ttctggattt ttcataacta 8220
aagctaaatc caaagacctg aaaaaggaca aaaagaaaaa aaaaaaaaga aaaaacaaag 8280
aaaaagaaga aaaaataata aagtcaagcg caaactgatg gggagacagt gggctctggt 8340
ttccaggatt gagacaatgg tactgcggtc ttggggagac tgcgttagct agtggggagt 8400
ggtgattttt ttcatgcttg tcacatctaa atggtcttta acatgagaaa gttttagagg 8460
ttataatttc ctgctttgtt tttatttaga ctatcaaatg aagttataca tgttgtcagt 8520
caaaaaatga agacaccctc tgccccaccc cacagaatgc tttttatctt gtctctttgg 8580
gttatgaccc aacaagctaa gtaccattaa tgtaattaac ttatttaaat tagttcctag 8640
tacataaatg tataggattt gggtaattat ttaatcatcc ttccttagtt tgattctact 8700
ccttgtactt atttatcaaa acctagacca atggtgcatc agagatgcaa aattctactt 8760
ggaatactct tgaagtttag tttgctttat aaagcagtga aattctgtta cagacaggga 8820
agaaatacag gttacaaaaa gagaatttgg gatattcttc cctcttaaat taacttttaa 8880
aatagtctaa gtaacaattt ttaaattatt taacttaagt tcgcagcccc acctggtacc 8940
aggcgaactt cacctcttaa ttattgtggc cctcggagcc ttcatattgt aacttattta 9000
tttaacttat tcagcatctg tgaaaggtgc actgtatagt ttatattttt aatttaaaac 9060
aacagagagc actgcagttt gtttgctgtc agaacaacag agcaaatttt gtggacaagc 9120
aatgactatt cagcctgaac ctgtgcattc agaaaacata agctgagacc ctgcttcacc 9180
agcctggatt tcggggcttc tatacagaaa ctggaaaaat aaattttaaa aaaatcgtaa 9240
acaaaaagag agaaaccctt acactagctg cttccaagaa tgaactctgt gtgtatgtaa 9300
agcaacaaaa caaaaaagga aaaaaacaaa aagcagaaaa aagaaaaaaa aaatgaaaaa 9360
ctttctattt ctagtgagaa ccaaagaagg ctacctcact gactttttcc atttgtaatt 9420
ttaatcgtgt tgatgacacc aaagatacca aagatttctt tctctgtgcg gtctgcattt 9480
tgcttgtgct cttttataat ttgaacgatt ttctctgaca tatggtatgt acagccacag 9540
ctcagatacc ccaaagaaat aattatctat gcgacggcgg ctgctaattt ggaaagggat 9600
attttctgtg tttctcttat atgtttgctg tctgctcgac atgttcaaga tgcgagttca 9660
gatgctgctg taattggatt ccttaaattc tgattacaaa ttgaggaagg aaactggttg 9720
gaaatggcct tcagtcctag ccatggcctc tatccccgct gggacctgtc acagtaaaga 9780
ctgccaatta ctgaaccaca gaagctctga ccattgagta gttgagctgg aagagacctt 9840
aggaatcatt tagtccaagc cccggtggcc cagaggaatg aaatagttat ccaaatcaaa 9900
taactcttga gagtgaaagc ccacacatgc ctcctggttc ctgccccagt gctccgctta 9960
ttgtacagtg ctacctctgc atgagagcgg tcccacattg acaaatagga tggtggcaat 10020
cctttagcaa tgagcaggga ctggggttta tctcttaaca ttttcagctg taaaattagt 10080
cacaagcatt ttcagtgtcc cattagtaca tagtcacata tggtcggttg cttcgtgaag 10140

-continued

```
gtggcctgtc ttgaaatact agggctcata cgggattttt gccctaggaa aaacatgttg  10200
atcccaatga tgtgatcact tttgaacctt tccattacaa agcattgtat agataacttt  10260
ttaattcagt aggaggagaa agttcattct tggcctgttg gctttgatta ttatgggtac  10320
tttaaagtca gtatttatca agaaagggaa cttgaccacc attggcacat gtgacattta  10380
agctcttcag ccttttcctt tttagttgta ggtgtttaca tttcatttct aagccaactc  10440
tgtatttatg agagaagttt aagccttaca tcatttgata ctaaagggtt atttgtggta  10500
aatgaaaaat gaccccaaaa ttacagagga atatgccagt ttaagaaatg gctacttaaa  10560
gttgcttctc tctttccttc ttactcatga aattaattgg tcttcttcaa gtttctttag  10620
attccattaa atgattaaat cactattaag agccattcat caacgtgatt tgtgtgttag  10680
ccaatgaatc tgtctcagct tttgaccaaa tgggttttag acaaatgcaa agatctgcct  10740
ctagtccata tggctctttt tgagtgctag tattttgcat ttcacataat gtagttattt  10800
tgagctttta aagagagcat ttagacaaag aagcaaagag aggaagggac caatcaactc  10860
atcagttcca tgcatcaaca aagcatagct agtagaggaa tataaatgac agattgacaa  10920
actgtaggaa acactgttac tctctttctg aagttttcaa gcaccatcct atgtgaaagt  10980
tccctcctgt ccaaacaagc tcaaggccca tcttctccct atacaaggca aacctgtaag  11040
gccttccttc caaagagtac attgctttgg ttttcttcct aaattcctat tggaattaga  11100
actctcagaa tccctgggag acagagcaaa gatgacttaa ttcattgagc agcagagctc  11160
cctataagtg aacatcacct tccccatctt tcctactgcc acacccatac gagagaggat  11220
ctagaaagag cgatggcagc ctgaacacag aaaacatccc cacttggcag acctctcctc  11280
agcaatcccc ccagcctcat gcttcacttg caaagtgtga cataaccacg ggacgagtgc  11340
cttgcttgaa ccaaagcaac gatttagcca gtctggacct ctctgtgctt tttttaattc  11400
ttcctgtgaa tacctcagct tcaactgggc ctccatacag tcagttggtg ggcttattgt  11460
actgtggtgc tttgcaatgc aaccctgcaa agaacaagat ttgtactaat accaaaggtt  11520
ctttctctat gtctcctcct ctgcctccct cgttcttccc ttttttctag ttcttcacgg  11580
ttccaaagct ttactatgaa cctgggcatg ttggcaatgc agaccgcgca attccttacc  11640
gaattttctc agatatacct catagacaat agtgtttaga gtaatgttat tatagcgtat  11700
gtaataaatt attcactgtt tcttttggta actgtgattt aaaaaaagaa aaaagaaaaa  11760
aaagctttat acgttttagg ttgtgctttt gtaatagatg aaaaaaggtg cgcttaaaaa  11820
gaaaatgtat gttttttttcc ccctttggat tttatttatg ctggattggg gaaagttgca  11880
gaatgagccc aaagtttaca gtttcatatt ttgctgaaga aacaatctgt gttcatttgc  11940
tctgttgaaa agaataatta ttttctacat ttgtgccact tggtctgaac aattaattgt  12000
tccgtgttaa cagtgtagta ttatgattag caactgccaa tcagtgctat aattttatgc  12060
atgaggctaa aaatttagca gtgtgatgca ttgtggtctt aatagcaaca tttttcattt  12120
tgaactagat cttcccccttt ggttcaatgg actttattta tgcatgggcg cctattgttt  12180
gttagcagtt gtggaacagt tgtgtataca ttaaactgtg aaaatgtaca cagttcagcc  12240
tcagacggtg gtaatattgg ttttattggg agatgtgtca cctcgaaaat accctttaca  12300
tctgttggga tctgaaaatg agtcacattg aattgggttc cagctttata atgagaaacg  12360
ttattcctaa tttttgagtt agccaatttg cattccacaa attgggatcc tcataaccca  12420
aatatatcac cgtatgtgag agggatttga aagcgagtat tgaaaaactc acctttgcat  12480
atttaatttc caccaaaagg agttattttg gctttatgct catgaactta gacctaactg  12540
```

```
gccatgtata tgtagatgca aattcatcta gctgtggccc tctttgatct ctgcttggga  12600
atggctattt ttgactatgc gtggtttctt ctcgtatttt gtgatcaggt cagctcccag  12660
tagaaactca aatggcatca atattactaa ctcttctctg cccacttctc ttttgtccac  12720
tctcctagac attcccacca actgttccag tgatttgggc aaaaatacgc agccatttcc  12780
caaaacttca catgtgcagc tatcatggct gtccctccct agacttggag gtgactctca  12840
cttaattttt acctgcccaa caatgttcca tctaccatct aaaaggtaat ataagaagaa  12900
gttttgaaac ccactttagg aaaaccatct tctttaaatc cttcaattat ctgaggcctc  12960
tatatgtcaa aactattttt cagttgcagg ggattgggca aacttgttct ttcttatact  13020
tgggttcaaa gacccattct ccagtttcat atttcccaaa ccaaaatgct tgacataaag  13080
ccaaatcaac tgccaagcac actttatttt gcataggagt atgcagccta gggaaccttg  13140
gttgaaaagc agcagtctgc tatgcaaaat attggaaatc actgacagtg tagcattcat  13200
attatctgtc aatgagggta tattgggaac gtgctctcgt gaataataaa aagcaacata  13260
tttttatttg gccttataaa ttaggttgtg gtaatgtaaa ctttgatata tagtcttttt  13320
atttttctct tattaatctg ccaaagatgg gaacagatac aagaattttt caaattggct  13380
tttgtaagac aattgatgat tgtaatagtg tttaatcttc cagaaagctt tatatgttgt  13440
tccacaataa aattgatatt tgtttcagca aagttttcct gacactcaca aacccacaaa  13500
ctgttcctct taatgcagat attgtagaat ctacaaagtt caaatccatt tttgatccaa  13560
agaaagtaga ggagtatttg agacatgagt gtacccagcc ctttttttaa tcacaggcaa  13620
tgcatgggtc tggctggtta cactttgcca agaagacttg tcttatgaaa cccaaggtat  13680
attttgttat gccattttat gtccttttct tttaacattg tggaaagtgg tatgttgaat  13740
caagtgtaag ctgagttttc cagacaactg aagtagctac atcatgaatg ttattttgtt  13800
attaaagggt ttttactcag tgctttgtgc caatggatgt ccttttcctt ggagacacat  13860
aactacaaaa ttacctcagc ttggcctggt tttctctcct gccctcttgg ggaaacatgg  13920
gcctggcctg ggaaaaggca ggtcatgggc tggaaggtag gttttggtac taggaagaaa  13980
tctctgtatc tgtcagcttt aaagagaact gggccaaaaa tctctaacct cactctctct  14040
ggactccaac acttccctgc aatcctttgg tcttgagcat gtgccagcat gaaggcagac  14100
tccagttcat acatgaaagg caagaaaaag aaaatagtaa ccttgaatct tctgtgggcc  14160
accaggcact cacctttccc caccttgcac actatccagt caaggctatt gcagcccatc  14220
tggtggcttt acatgggaca ttaccaaagg cttcttcctc catcctgggg ttgcaaagga  14280
tccaggtccc ctccatccag tggggctctt ccacatcaga agtccccctc ccaccatcct  14340
ctgcatcctg tttagctatc ccatctatac cttttggaga tgattattta gaaaacaaag  14400
aaaggtatgg aatggggttt cctattgttt gctaggttat attttagcaa ttctcaattc  14460
tttgatctgg aaaaatacaa gagggaaaag gagaccccac tatctccctg tgctttgctc  14520
ccatctcagg gggcaggggc agtgcacatt gcctatgctg ttgatctgtc ttgggcgaca  14580
ggctgaatca cagctattgc cccagccaaa aacatggccc atcaatgcct actttatctc  14640
tgcttgaaaa tcctattcaa aaagttgtag agtttgaggt ttttatcccc ccatatcctt  14700
tgctttggtc cagtttggcc tttagcataa gagtcagctt tatctctagg aaagtttttt  14760
cagattatga caaggaacct gccacctggg aagaaaagag tccgaagact agcaatcgga  14820
taggtagtca taccattaac agatacttcc ttgaaggtag aatattattt cctttcttta  14880
```

cagttttgtg ttacacaagt ccaagtggtg ccagcaaact tcttaccgtg aaatgttgta 14940
aaacacctgg catactgaaa tttctgaaac aaaaacacaa gctccacatt gataacttga 15000
taaataacca ctaaagttta gatgcaggga ctgagatgat acaggcaaaa tcttggtgtt 15060
ggtttctctt ttaattcgta tcttcgatca cctaaccttt ctcaatccaa gagcagttca 15120
gtcttttctc cccaagtcta ggatgccaaa gagcatcata ggaaaagata attagggatt 15180
gaccagcatt tcaattagtt ctcttcttca tctttgcatt tctcaaaagt gttctcctgg 15240
accagaggga aagagctggt ccattttttt tcattctttc tattcaaatt tttccaccca 15300
gacaatactt tattaacaca gatactgtag atccttcctt ggtcagtgaa ttattacaag 15360
aggagctatc cttccaccaa agtgagtgaa aacaagttcc agtatctttt cttccatcca 15420
gttttgttct cagaatccaa gtcagtcctg ggtcttttct cactttagac cctggcctca 15480
gatgtgttta ttcttgctat ttaaaaatac ctttaaattt cacatgctgg cctgcagaac 15540
ttgcatcctt tgttctatac tgttgactgc ttgatggtat tgaaaggtga ctataatgag 15600
ggaagaaagg aggaggtaaa gagagaagaa tttgtcccag atctgtttaa agtttcaaaa 15660
tttaaaaagg gacccattaa attatgggaa aatggctata gagtgtgagc ctccgttgac 15720
catatgctca aagaccgtac tctgccacct gccttccagg tagctattct agaaactcag 15780
tcctttgtgg aaacccaact accttttaaa agtctctttc cagattccaa aaggacaaga 15840
gatcagagag tcacatatac gcctcttgtt ttattttctt gctttcacgg gtattattgc 15900
caagaaaatc gtagggaaaa actttaaact tttcttttca gttgatccct ttgacatcac 15960
ctctcatgtt taaaatcagg aaaacacacc cctaaaattt gcactctctt ccgttttgaa 16020
aaagaaaacc cacacacaaa tgcacactat taccgtcttt caccctgcgc tatatttcca 16080
aagtgtatta taatccagat attgccccat ctcaaacatg ttaagtcaga ctgtgctgaa 16140
agactttcca gggacggtca acagggtata tgttcagtgg ctgccctgaa atcctggtgg 16200
ggatgaggat cacgcttcat catcaagggg atgcccatcc cctgataagc tcccagtcct 16260
tttggaagat ttctttgaat gttaattgca ttttcagttt tgctcatttc ccaccccaat 16320
gttttgtctg caacatcgct tacactggat tctttctatt tttattccta tcattaaatg 16380
gtagtgctgt aaattctgca attaatgtta aataaactgc tttaattcat tga 16433

<210> SEQ ID NO 17
<211> LENGTH: 3721
<212> TYPE: DNA
<213> ORGANISM: Homo sapiens

<400> SEQUENCE: 17
aactcgctgt agtaattcca gcgagaggca gagggagcga gcgggcggcc ggctagggtg 60
gaagagccgg gcgagcagag ctgcgctgcg ggcgtcctgg gaagggagat ccggagcgaa 120
tagggggctt cgcctctggc ccagccctcc cgctgatccc ccagccagcg gtccgcaacc 180
cttgccgcat ccacgaaact ttgcccatag cagcgggcgg gcactttgca ctggaactta 240
caacacccga gcaaggacgc gactctcccg acgcggggag gctattctgc ccatttgggg 300
acacttcccc gccgctgcca ggacccgctt ctctgaaagg ctctccttgc agctgcttag 360
acgctggatt tttttcgggt agtggaaaac cagcagcctc ccgcgacgat gcccctcaac 420
gttagcttca ccaacaggaa ctatgacctc gactacgact cggtgcagcc gtatttctac 480
tgcgacgagg aggagaactt ctaccagcag cagcagcaga gcgagctgca gcccccggcg 540
cccagcgagg atatctggaa gaaattcgag ctgctgccca ccccgcccct gtcccctagc 600

```
cgccgctccg ggctctgctc gccctcctac gttgcggtca cacccttctc ccttcgggga    660
gacaacgacg gcggtggcgg gagcttctcc acggccgacc agctggagat ggtgaccgag    720
ctgctgggag gagacatggt gaaccagagt ttcatctgcg acccggacga cgagaccttc    780
atcaaaaaca tcatcatcca ggactgtatg tggagcggct tctcggccgc cgccaagctc    840
gtctcagaga agctggcctc ctaccaggct gcgcgcaaag acagcggcag cccgaacccc    900
gcccgcggcc acagcgtctg ctccacctcc agcttgtacc tgcaggatct gagcgccgcc    960
gcctcagagt gcatcgaccc ctcggtggtc ttcccctacc ctctcaacga cagcagctcg   1020
cccaagtcct gcgcctcgca agactccagc gccttctctc cgtcctcgga ttctctgctc   1080
tcctcgacgg agtcctcccc gcagggcagc cccgagcccc tggtgctcca tgaggagaca   1140
ccgcccacca ccagcagcga ctctgaggag gaacaagaag atgaggaaga aatcgatgtt   1200
gtttctgtgg aaaagaggca ggctcctggc aaaaggtcag agtctggatc accttctgct   1260
ggaggccaca gcaaacctcc tcacagccca ctggtcctca agaggtgcca cgtctccaca   1320
catcagcaca actacgcagc gcctccctcc actcggaagg actatcctgc tgccaagagg   1380
gtcaagttgg acagtgtcag agtcctgaga cagatcagca acaaccgaaa atgcaccagc   1440
cccaggtcct cggacaccga ggagaatgtc aagaggcgaa cacacaacgt cttggagcgc   1500
cagaggagga acgagctaaa acggagcttt tttgccctgc gtgaccagat cccggagttg   1560
gaaaacaatg aaaaggcccc caaggtagtt atccttaaaa aagccacagc atacatcctg   1620
tccgtccaag cagaggagca aaagctcatt tctgaagagg acttgttgcg gaaacgacga   1680
gaacagttga aacacaaact tgaacagcta cggaactctt gtgcgtaagg aaaagtaagg   1740
aaaacgattc cttctaacag aaatgtcctg agcaatcacc tatgaacttg tttcaaatgc   1800
atgatcaaat gcaacctcac aaccttggct gagtcttgag actgaaagat ttagccataa   1860
tgtaaactgc ctcaaattgg actttgggca taaaagaact tttttatgct taccatcttt   1920
tttttttctt taacagattt gtatttaaga attgttttta aaaaatttta agatttacac   1980
aatgtttctc tgtaaatatt gccattaaat gtaaataact ttaataaaac gtttatagca   2040
gttacacaga atttcaatcc tagtatatag tacctagtat tataggtact ataaacccta   2100
attttttta tttaagtaca ttttgctttt taaagttgat ttttttctat tgtttttaga   2160
aaaaataaaa taactggcaa atatatcatt gagccaaatc ttaagttgtg aatgttttgt   2220
ttcgtttctt ccccctccca accaccacca tccctgtttg ttttcatcaa ttgccccttc   2280
agagggtggt cttaagaaag gcaagagttt tcctctgttg aaatgggtct gggggcctta   2340
aggtctttaa gttcttggag gttctaagat gcttcctgga gactatgata acagccagag   2400
ttgacagtta gaaggaatgg cagaaggcag gtgagaaggt gagaggtagg caaaggagat   2460
acaagaggtc aaaggtagca gttaagtaca caaagaggca taaggactgg ggagttggga   2520
ggaaggtgag gaagaaactc ctgttacttt agttaaccag tgccagtccc ctgctcactc   2580
caaacccagg aattctgccc agttgatggg gacacggtgg gaaccagctt ctgctgcctt   2640
cacaaccagg cgccagtcct gtccatgggt tatctcgcaa accccagagg atctctggga   2700
ggaatgctac tattaaccct atttcacaaa caaggaaata gaagagctca aagaggttat   2760
gtaacttatc tgtagccacg cagataatac aaagcagcaa tctggaccca ttctgttcaa   2820
aacacttaac ccttcgctat catgccttgg ttcatctggg tctaatgtgc tgagatcaag   2880
aaggtttagg acctaatgga cagactcaag tcataacaat gctaagctct atttgtgtcc   2940
```

```
caagcactcc taagcatttt atccctaact ctacatcaac cccatgaagg agatactgtt   3000
gatttcccca tattagaagt agagagggaa gctgaggcac acaaagactc atccacatgc   3060
ccaagattca ctgataggga aaagtggaag cgagatttga acccaggctg tttactccta   3120
acctgtccaa gccacctctc agacgacggt aggaatcagc tggctgcttg tgagtacagg   3180
agttacagtc cagtgggtta tgttttttaa gtctcaacat ctaagcctgg tcaggcatca   3240
gttccccttt ttttgtgatt tattttgttt ttattttgtt gttcattgtt taatttttcc   3300
ttttacaatg agaaggtcac catcttgact cctaccttag ccatttgttg aatcagactc   3360
atgacggctc ctgggaagaa gccagttcag atcataaaat aaaacatatt tattctttgt   3420
catgggagtc attattttag aaactacaaa ctctccttgc ttccatcctt ttttacatac   3480
tcatgacaca tgctcatcct gagtccttga aaaggtattt ttgaacatgt gtattaatta   3540
taagcctctg aaaacctatg gcccaaacca gaaatgatgt tgattatata ggtaaatgaa   3600
ggatgctatt gctgttctaa ttacctcatt gtctcagtct caaagtaggt cttcagctcc   3660
ctgtactttg ggattttaat ctaccaccac ccataaatca ataaataatt actttctttg   3720
a                                                                   3721
```

<210> SEQ ID NO 18
<211> LENGTH: 2258
<212> TYPE: DNA
<213> ORGANISM: Homo sapiens

<400> SEQUENCE: 18

```
gcagccccgg gcgccgcgcg tcctgcccgg cctgcggccc cagcccttgc gccgctcgtc     60
cgacccgcga tcgtccacca gaccgtgcct cccggccgcc cggccggccc gcgtgcatgc    120
ttcggtctgg gccagcctct gggccgtccg tccccactgg ccgggccatg ccgagtcgcc    180
gcgtcgccag accgccggct gcgccggagc tgggggcctt agggtccccc gacctctcct    240
cactctcgct cgccgtttcc aggagcacag atgaattgga gatcatcgac gagtacatca    300
aggagaacgg cttcggcctg gacgggggac agccgggccc gggcgagggg ctgccacgcc    360
tggtgtctcg cggggctgcg tccctgagca cggtcaccct gggccctgtg gcgcccccag    420
ccacgccgcc gccttggggc tgccccctgg gccgactagt gtccccagcg ccgggcccgg    480
gcccgcagcc gcacctggtc atcacggagc agcccaagca gcgcggcatg cgcttccgct    540
acgagtgcga gggccgctcg gccggcagca tccttgggga gagcagcacc gaggccagca    600
agacgctgcc cgccatcgag ctccgggatt gtggagggct gcgggaggtg gaggtgactg    660
cctgcctggt gtggaaggac tggcctcacc gagtccaccc ccacagcctc gtggggaaag    720
actgcaccga cggcatctgc agggtgcggc tccggcctca cgtcagcccc cggcacagtt    780
ttaacaacct gggcatccag tgtgtgagga agaaggagat tgaggctgcc attgagcgga    840
agattcaact gggcattgac ccctacaacg ctgggtccct gaagaaccat caggaagtag    900
acatgaatgt ggtgaggatc tgcttccagg cctcatatcg ggaccagcag ggacagatgc    960
gccggatgga tcctgtgctt tccgagcccg tctatgacaa gaaatccaca aacacatcag   1020
agctgcggat ttgccgaatt aacaaggaaa gcgggccgtg caccggtggc gaggagctct   1080
acttgctctg cgacaaggtg cagaaagagg acatatcagt ggtgttcagc agggcctcct   1140
gggaaggtcg ggctgacttc tcccaggccg acgtgcaccg ccagattgcc attgtgttca   1200
agacgccgcc ctacgaggac ctggagattg tcgagcccgt gacagtcaac gtcttcctgc   1260
agcggctcac cgatggggtc tgcagcgagc cattgccttt cacgtacctg cctcgcgacc   1320
```

```
atgacagcta cggcgtggac aagaagcgga aacgggggat gcccgacgtc cttggggagc   1380
tgaacagctc tgacccccat ggcatcgaga gcaaacggcg gaagaaaaag ccggccatcc   1440
tggaccactt cctgcccaac cacggctcag gcccgttcct cccgccgtca gccctgctgc   1500
cagaccctga cttcttctct ggcaccgtgt ccctgcccgg cctggagccc cctggcgggc   1560
ctgacctcct ggacgatggc tttgcctacg accctacggc cccccacactc ttcaccatgc  1620
tggacctgct gcccccggca ccgccacacg ctagcgctgt tgtgtgcagc ggaggtgccg   1680
gggccgtggt tggggagacc cccggccctg aaccactgac actggactcg taccaggccc   1740
cgggccccgg ggatggaggc accgccagcc ttgtgggcag caacatgttc cccaatcatt   1800
accgcgaggc ggcctttggg ggcggcctcc tatccccggg gcctgaagcc acgtagcccc   1860
gcgatgccag aggaggggca ctgggtgggg agggaggtgg aggagccgtg caatcccaac   1920
caggatgtct agcaccccca tccccttggc ccttcctcat gcttctgaag tggacatatt   1980
cagccttggc gagaagctcc gttgcacggg tttccccttg agcccatttt acagatgagg   2040
aaactgagtc cggagaggaa aagggacatg gctcccgtgc actagcttgt tacagctgcc   2100
tctgtcccca catgtggggg caccttctcc agtaggattc ggaaaagatt gtacatatgg   2160
gaggaggggg cagattcctg gccctccctc cccagacttg aaggtggggg gtaggttggt   2220
tgttcagagt cttcccaata aagatgagtt tttgagcc                           2258
```

<210> SEQ ID NO 19
<211> LENGTH: 3871
<212> TYPE: DNA
<213> ORGANISM: Homo sapiens

<400> SEQUENCE: 19

```
atgaacctct gaaaactgcc ggcatctgag gtttcctcca aggccctctg aagtgcagcc     60
cataatgaag gtcttggcgg caggagttgt gcccctgctg ttggttctgc actggaaaca    120
tggggcgggg agccccctcc ccatcacccc tgtcaacgcc acctgtgcca tacgccaccc    180
atgtcacaac aacctcatga accagatcag gagccaactg gcacagctca atggcagtgc    240
caatgccctc tttattctct attacacagc ccagggggag ccgttcccca acaacctgga    300
caagctatgt ggccccaacg tgacggactt cccgcccttc cacgccaacg gcacggagaa    360
ggccaagctg gtggagctgt accgcatagt cgtgtacctt ggcacctccc tgggcaacat    420
cacccgggac cagaagatcc tcaaccccag tgccctcagc ctccacagca agctcaacgc    480
caccgccgac atcctgcgag gcctccttag caacgtgctg tgccgcctgt gcagcaagta    540
ccacgtgggc catgtggacg tgacctacgg ccctgacacc tcgggtaagg atgtcttcca    600
gaagaagaag ctgggctgtc aactcctggg gaagtataag cagatcatcg ccgtgttggc    660
ccaggccttc tagcaggagg tcttgaagtg tgctgtgaac cgagggatct caggagttgg    720
gtccagatgt gggggcctgt ccaagggtgg ctggggccca gggcatcgct aaacccaaat    780
gggggctgct ggcagacccc gagggtgcct ggccagtcca ctccactctg ggctgggctg    840
tgatgaagct gagcagagtg gaaacttcca tagggaggga gctagaagaa ggtgcccctt    900
cctctgggag attgtggact ggggagcgtg ggctggactt ctgcctctac ttgtcccttt    960
ggccccttgc tcactttgtg cagtgaacaa actacacaag tcatctacaa gagccctgac   1020
cacagggtga gacagcaggg cccaggggag tggaccagcc cccagcaaat tatcaccatc   1080
tgtgcctttg ctgcccctta ggttgggact taggtgggcc agaggggcta ggatcccaaa   1140
```

-continued

```
ggactccttg tcccctagaa gtttgatgag tggaagatag agaggggcct ctgggatgga   1200
aggctgtctt cttttgagga tgatcagaga acttgggcat aggaacaatc tggcagaagt   1260
ttccagaagg aggtcacttg gcattcaggc tcttggggag gcagagaagc caccttcagg   1320
cctgggaagg aagacactgg gaggaggaga ggcctggaaa gctttggtag gttcttcgtt   1380
ctcttccccg tgatcttccc tgcagcctgg gatggccagg gtctgatggc tggacctgca   1440
gcaggggttt gtggaggtgg gtagggcagg ggcaggttgc taagtcaggt gcagaggttc   1500
tgagggaccc aggctcttcc tctgggtaaa ggtctgtaag aaggggctgg ggtagctcag   1560
agtagcagct cacatctgag gccctgggag gccttgtgag gtcacacaga ggtacttgag   1620
ggggactgga ggccgtctct ggtccccagg gcaagggaac agcagaactt agggtcaggg   1680
tctcagggaa ccctgagctc caagcgtgct gtgcgtctga cctggcatga tttctattta   1740
ttatgatatc ctatttatat taacttattg gtgctttcag tggccaagtt aattcccctt   1800
tccctggtcc ctactcaaca aaatatgatg atggctcccg acacaagcgc cagggccagg   1860
gcttagcagg gcctggtctg gaagtcgaca atgttacaag tggaataagc cttacgggtg   1920
aagctcagag aagggtcgga tctgagagaa tggggaggcc tgagtgggag tggggggcct   1980
tgctccaccc ccccccatcc cctactgtga cttgctttag ggtgtcaggg tccaggctgc   2040
aggggctggg ccaatttgtg gagaggccgg gtgcctttct gtcttgattc caggggggctg   2100
gttcacactg ttcttgggcg ccccagcatt gtgttgtgag gcgcactgtt cctggcagat   2160
attgtgcccc ctggagcagt gggcaagaca gtccttgtgg cccaccctgt ccttgtttct   2220
gtgtccccat gctgcctctg aaatagcgcc ctggaacaac cctgcccctg cacccagcat   2280
gctccgacac agcagggaag ctcctcctgt ggcccggaca cccatagacg gtgcgggggg   2340
cctggctggg ccagacccca ggaaggtggg gtagactggg gggatcagct gcccattgct   2400
cccaagagga ggagagggag gctgcagatg cctgggactc agaccaggaa gctgtgggcc   2460
ctcctgctcc acccccatcc cactcccacc catgtctggg ctcccaggca gggaacccga   2520
tctcttcctt tgtgctgggg ccaggcgagt ggagaaacgc cctccagtct gagagcaggg   2580
gagggaagga ggcagcagag ttggggcagc tgctcagagc agtgttctgg cttcttctca   2640
aaccctgagc gggctgccgg cctccaagtt cctccgacaa gatgatggta ctaattatgg   2700
tacttttcac tcactttgca cctttccctg tcgctctcta agcactttac ctggatggcg   2760
cgtgggcagt gtgcaggcag gtcctgaggc ctggggttgg ggtggagggt gcggcccgga   2820
gttgtccatc tgtccatccc aacagcaaga cgaggatgtg gctgttgaga tgtgggccac   2880
actcaccctt gtccaggatg cagggactgc cttctccttc ctgcttcatc cggcttagct   2940
tggggctggc tgcattcccc caggatgggc ttcgagaaag acaaacttgt ctggaaacca   3000
gagttgctga ttccacccgg ggggcccggc tgactcgccc atcacctcat ctccctgtgg   3060
acttgggagc tctgtgccag gcccaccttg cggccctggc tctgagtcgc tctcccaccc   3120
agcctggact tggccccatg ggacccatcc tcagtgctcc ctccagatcc cgtccggcag   3180
cttggcgtcc accctgcaca gcatcactga atcacagagc ctttgcgtga aacagctctg   3240
ccaggccggg agctgggttt ctcttccctt tttatctgct ggtgtggacc acacctgggc   3300
ctggccggag gaagagagag tttaccaaga gagatgtctc cgggccctta tttattattt   3360
aaacattttt ttaaaaagca ctgctagttt acttgtctct cctccccatc gtccccatcg   3420
tcctccttgt ccctgacttg ggcacttcc accctgaccc agccagtcca gctctgcctt   3480
gccggctctc cagagtagac atagtgtgtg gggttggagc tctggcaccc ggggaggtag   3540
```

```
catttccctg cagatggtac agatgttcct gccttagagt catctctagt tccccacctc   3600

aatcccggca tccagccttc agtcccgccc acgtgctagc tccgtgggcc caccgtgcgg   3660

ccttagaggt ttccctcctt cctttccact gaaaagcaca tggccttggg tgacaaattc   3720

ctctttgatg aatgtaccct gtggggatgt ttcatactga cagattattt ttatttattc   3780

aatgtcatat ttaaaatatt tattttttat accaaatgaa tacttttttt tttaagaaaa   3840

aaaagagaaa tgaataaaga atctactctt g                                 3871


<210> SEQ ID NO 20
<211> LENGTH: 3125
<212> TYPE: DNA
<213> ORGANISM: Homo sapiens

<400> SEQUENCE: 20

ccgcaaccag agccgccgcc acggtgagtg gctggattca gacccctggg tggccgggac     60

aagagaaaag agggaggagg gcctttagcg gacagcgcct ggggctggag agcagcagct    120

gcacacagcc ggaaagggcg cgcaggcgac gacactcgga tccacgtcga caccgttgta    180

caaagatacg cggacccgcg ggcgtctaaa attctgggaa gcagaacctg gccggagcca    240

ctagacagag ccgggcctag cccagagaca tggagagttg ctacaaccca ggtctggatg    300

gtattattga atatgatgat ttcaaattga actcctccat tgtggaaccc aaggagccag    360

ccccagaaac agctgatggc ccctacctgg tgatcgtgga acagcctaag cagagaggct    420

tccgatttcg atatggctgt gaaggcccct cccatggagg actgcccggt gcctccagtg    480

agaagggccg aaagacctat cccactgtca agatctgtaa ctacgaggga ccagccaaga    540

tcgaggtgga cctggtaaca cacagtgacc cacctcgtgc tcatgcccac agtctggtgg    600

gcaagcaatg ctcggagctg gggatctgcg ccgtttctgt ggggcccaag gacatgactg    660

cccaatttaa caacctgggt gtcctgcatg tgactaagaa gaacatgatg ggactatga    720

tacaaaaact tcagaggcag cggctccgct ctaggcccca gggccttacg gaggccgagc    780

agcgggagct ggagcaagag gccaaagaac tgaagaaggt gatggatctg agtatagtgc    840

ggctgcgctt ctctgccttc cttagagcca gtgatggctc cttctccctg cccctgaagc    900

cagtcatctc ccagcccatc catgacagca aatctccggg ggcatcaaac ctgaagattt    960

ctcgaatgga caagacagca ggctctgtgc ggggtggaga tgaagtttat ctgctttgtg   1020

acaaggtgca gaaagatgac attgaggttc ggttctatga ggatgatgag aatggatggc   1080

aggcctttgg ggacttctct cccacagatg tgcataaaca gtatgccatt gtgttccgga   1140

caccccccta tcacaagatg aagattgagc ggcctgtaac agtgtttctg caactgaaac   1200

gcaagcgagg aggggacgtg tctgattcca aacagttcac ctattaccct ctggtggaag   1260

acaaggaaga ggtgcagcgg aagcggagga aggccttgcc caccttctcc cagcccttcg   1320

ggggtggctc ccacatgggt ggaggctctg gggtgcagc cgggggctac ggaggagctg   1380

gaggaggtgg cagcctcggt ttcttcccct cctccctggc ctacagcccc taccagtccg   1440

gcgcgggccc catgggctgc tacccgggag gcgggggcgg ggcgcagatg gccgccacgg   1500

tgcccagcag ggactccggg gaggaagccg cggagccgag cgccccctcc aggacccccc   1560

agtgcgagcc gcaggccccg gagatgctgc agcgagctcg agagtacaac gcgcgcctgt   1620

tcggcctggc gcagcgcagc gcccgagccc tactcgacta cggcgtcacc gcggacgcgc   1680

gcgcgctgct ggcgggacag cgccacctgc tgacggcgca ggacgagaac ggagacacac   1740
```

```
cactgcacct agccatcatc cacgggcaga ccagtgtcat tgagcagata gtctatgtca   1800
tccaccacgc ccaggacctc ggcgttgtca acctcaccaa ccacctgcac cagacgcccc   1860
tgcacctggc ggtgatcacg gggcagacga gtgtggtgag ctttctgctg cgggtaggtg   1920
cagacccagc tctgctggat cggcatggag actcagccat gcatctggcg ctgcgggcag   1980
gcgctggtgc tcctgagctg ctgcgtgcac tgcttcagag tggagctcct gctgtgcccc   2040
agctgttgca tatgcctgac tttgagggac tgtatccagt acacctggcg gtccgagccc   2100
gaagccctga gtgcctggat ctgctggtgg acagtggggc tgaagtggag gccacagagc   2160
ggcagggggg acgaacagcc ttgcatctag ccacagagat ggaggagctg ggggttggtca   2220
cccatctggt caccaagctc cgggccaacg tgaacgctcg cacctttgcg ggaaacacac   2280
ccctgcacct ggcagctgga ctggggtacc cgaccctcac ccgcctcctt ctgaaggctg   2340
gtgctgacat ccatgctgaa aacgaggagc ccctgtgccc actgccttca ccccctacct   2400
ctgatagcga ctcggactct gaagggcctg agaaggacac ccgaagcagc ttccggggcc   2460
acacgcctct tgacctcact tgcagcacca aggtgaagac cttgctgcta aatgctgctc   2520
agaacaccat ggagccaccc ctgaccccgc ccagcccagc agggccggga ctgtcacttg   2580
gtgatacagc tctgcagaac ctggagcagc tgctagacgg gccagaagcc cagggcagct   2640
gggcagagct ggcagagcgt ctggggctgc gcagcctggt agacacgtac cgacagacaa   2700
cctcacccag tggcagcctc ctgcgcagct acgagctggc tggcggggac ctggcaggtc   2760
tactggaggc cctgtctgac atgggcctag aggagggagt gaggctgctg aggggtccag   2820
aaacccgaga caagctgccc agcacagcag aggtgaagga agacagtgcg tacgggagcc   2880
agtcagtgga gcaggaggca gagaagctgg gcccaccccc tgagccacca ggagggctct   2940
gccacgggca cccccagcct caggtgcact gacctgctgc ctgcccccag ccccccttccc  3000
ggaccccctg tacagcgtcc ccacctattt caaatcttat ttaacacccc acacccaccc   3060
ctcagttggg acaaataaag gattctcatg ggaaggggag gacccctcct tcccaactta   3120
tggca                                                               3125
```

<210> SEQ ID NO 21
<211> LENGTH: 6713
<212> TYPE: DNA
<213> ORGANISM: Homo sapiens

<400> SEQUENCE: 21

```
gtagtgactc atctcgggca gagcgctagg gctccgagcg aaccagcgag cgagcgaacg     60
agcggcgctc ggcggggaca gaaagaggga gagagagaga gagagagagg gagaggcgcg    120
gccgggcgag gcgggcccgt ccgggagcgg gctccgggga aggggtgcgg gtctgggcgc    180
cggagcgggg agcggggccg cgtccctctc agcgccagct ctacttgagc cccacgagcc    240
gctgtccccc tggcgcgctc ggggccgcgg gacgggcgca cgccgccttc tcctagtcaa    300
gtatccgagc cgccccgaaa ctcgggcggc gagtcggcca cgggaagttt attctccggc    360
tccttttcta aaaggaagaa acagaagttt ctcccagcgg acagcttttc tttccgcctt    420
tttggccctg tctgaaatcg ggggtcccca gggctggcag gccaggctcg ctgggctcct    480
aatctttttt ttaatttcca atttttgatt gggccgtggg tccccgctga gctccggctg    540
cgcgcggggg cgggagggcg cgcgcagggg agggaccgag agacgcgccg actttttaga    600
gggagggatc gggtggacaa ctggtcccgc ggcgctcgca gagccggaaa gaagtgctgt    660
aagggacgct cgggggacgc tgttcctgag gtgtcgccgc ctccctgtcc tcgccctccg    720
```

```
cggtgggga gaaacccagg agcgaagccc agagcccgcg gcgcggccgg cggacgaacg    780
agcgcgcagc agccggtgcg cggccgcggc gagggcgggg gaagaaaaac accctgtttc    840
ctctccggcc cccaccgcgg atcatgtacc aggattatcc cgggaacttt gacacctcgt    900
cccggggcag cagcggctct cctgcgcacg ccgagtccta ctccagcggc ggcggcggcc    960
agcagaaatt ccgggtagat atgcctggct caggcagtgc attcatcccc accatcaacg   1020
ccatcacgac cagccaggac ctgcagtgga tggtgcagcc cacagtgatc acctccatgt   1080
ccaacccata ccctcgctcg caccccctaca gcccccctgcc gggcctggcc tctgtccctg   1140
gacacatggc cctcccaaga cctggcgtga tcaagaccat tggcaccacc gtgggccgca   1200
ggaggagaga tgagcagctg tctcctgaag aggaggagaa gcgtcgcatc cggcgggaga   1260
ggaacaagct ggctgcagcc aagtgccgga accgacgccg ggagctgaca gagaagctgc   1320
aggcggagac agaggagctg gaggaggaga agtcaggcct gcagaaggag attgctgagc   1380
tgcagaagga gaaggagaag ctggagttca tgttggtggc tcacggccca gtgtgcaaga   1440
ttagccccga ggagcgccga tcgcccccag cccctgggct gcagcccatg cgcagtgggg   1500
gtggctcggt gggcgctgta gtggtgaaac aggagcccct ggaagaggac agcccctcgt   1560
cctcgtcggc ggggctggac aaggcccagc gctctgtcat caagcccatc agcattgctg   1620
ggggcttcta cggtgaggag cccctgcaca cccccatcgt ggtgacctcc acacctgctg   1680
tcactccggg cacctcgaac ctcgtcttca cctatcctag cgtcctggag caggagtcac   1740
ccgcatctcc ctccgaatcc tgctccaagg ctcaccgcag aagcagtagc agcggggacc   1800
aatcatcaga ctccttgaac tcccccactc tgctggctct gtaacccagt gcacctccct   1860
ccccagctcc ggagggggtc ctcctcgctc ctccttccca gggaccagca ccttcaagcg   1920
ctccagggcc gtgagggcaa gagggggacc tgccaccagg gagcttcctg gctctggggg   1980
acccaggtgg gacttagcag tgagtattgg aagacttggg ttgatctctt agaagccatg   2040
ggacctcctc cctcattcat cttgcaagca aatcccattt cttgaaaagc cttggagaac   2100
tcggtttggt agacttggac atctctctgg cttctgaaga gcctgaagct ggcctggacc   2160
attcctgtcc ctttgttacc atactgtctc tggagtgatg gtgtccttcc ctgccccacc   2220
acgcatgctc agtgcctttt ggtttcacct tccctcgact tgaccctttc ctcccccagc   2280
gtcagtttca ctccctcttg gtttttatca aatttgccat gacatttcat ctgggtggtc   2340
tgaatattaa agctcttcat ttctggagat ggggcagcag gtggctcttc tgctggggct   2400
gacttgtcca gaaggggaca aagtgcaata cagagccttc cctaccctga cgcctcccag   2460
tcatcatctc cagaactccc agcggggctc cctgagctct caaggagatg ctgccatcac   2520
tgggaggctc agaggaccct tcctgcccac cttcggagac ggcttctgga ggaacggctt   2580
ggccagaaga cagggtgtga gtgagacagt ggggcacagg ttgggtttgc caaacgccta   2640
attaccaggc caggaagcat gccaacaaag ccacacgggt gtcctagcca gcttcccttc   2700
acctggtgtc ttgagtaggg cgtctcctgt aattactgcc ttgccattct gcccctggac   2760
ccttctctcc ggaccaggga ggcgtccctc cctaggagcc acacattata ctccaagtcc   2820
ctgccgggct ccgcctttcc cccaccctgg ctctcagggt gacgccaccc acagagattt   2880
aatgagcgtg ggcctggacc ttccccagat gctgccaggc agcccctccc caagcctcaa   2940
agaagcattt gctgaggatg gagaggcagg ggagggaggc gggaggccgt cactggagtg   3000
gcgtctgcag cagctgctgc cccagcaccc gctcagcctg tcctggctgc tcacctcccc   3060
```

```
gcagggcacc gggcctttcc tgccctctgt ggtcatctgc cacctgctgg atcaagtgct   3120
ttctctttta cactcccctg tccccacccc agtgcactct tctggcccag gcagcaagca   3180
agctgtgaac agctggcctg agctgtcgct gtggcttgtg gctcatgcgc cattcctggt   3240
tgtctgttga atctttctgg ctgctggaat tggagatagg atgttttgct tcccactgca   3300
ggagagctgc cccctttcac ggggttgggg aagggtcccc ctggcctcca gcaggagcac   3360
agctcagcag ggtccctgct gcccacccct ctgagccttt tctccccagg gtatggctcc   3420
tgctgagttt cttgtccagc agggccttga caggaatcca gggagtagct cctggccaga   3480
accagcctct gcggggcttg tgctctgcaa agactctgct gctggggatt cagctctaga   3540
ggtcacagta tcctcgtttg aaagataatt aagatccccc gtggagaaag cagtgacaca   3600
ttcacacagc tgttccctcg catgttattt catgaacatg acctgttttc gtgcactaga   3660
cacacagagt ggaacagccg tatgcttaaa gtacatgggc cagtgggact ggaagtgacc   3720
tgtacaagtg atgcagaaag gagggtttca aagaaaaagg attttgttta aaatacttta   3780
aaaatgttat ttcctgcatc ccttggctgt gatgcccctc tcccgatttc ccaggggctc   3840
tgggagggac ccttctaaga agattgggca gttgggtttc tggcttgaga tgaatccaag   3900
cagcagaatg agccaggagt agcaggagat gggcaaagaa aactggggtg cactcagctc   3960
tcacaggggt aatcatctca agtggtattt gtagccaagt gggagctatt ttcttttttg   4020
tgcatataga tatttcttaa atgaagctgc tttcttgtct tttatttcta aaagcccccct  4080
tataccccac tttgtgcagc aaagatcccc gtgcaggtca cagcctgatt tgtggccagg   4140
ctggacaaat tcctgaggca caacttggct tcagttcaga tttcaagctg tgttggtgtt   4200
gggaccagca gaaggcaaac gtccagccaa cacacaggac tgtaagagga ctctgagcta   4260
cgtgccctgt gaagaccccc aggctttgtc ataggaggtc gttcagcttc cccaaagtca   4320
gaggtgattt gatttgggga agactgaata ttcacaccta agtcgtgagc atatcctgag   4380
ttttacttcc ttatggcttg ccctccaagt tctctctctc atacacacac acacccttgc   4440
tccagaatca ccagacacct ccatggctcc agctatggga acagctgcat tggggctgcc   4500
tttctgtttg gcttaggaac ttctgtgctt cttgtggctc cactcgcgag gcagctcgga   4560
ggtgtggact ccgattgggc tgcaggcagc tctgggacgg cacagggcgg gcgctctgat   4620
cagctcgtgt aaaacacacc gtcttcttgg cctcctggcc agtctttctg cgaatagtcc   4680
tctccctggc cagttgaatg ggggaagctg ctggcacagg aaggagaggc gatcccggct   4740
gaggcttagg aaattgctgg agccggctcc aagcagataa ttcactgggg aggttttcag   4800
agtcaaacat cattctgcct gtgttggggg ccaggtgtgt cacacaagca tctcaaagtc   4860
aaaagccatc tggggctgct gcttctgttt ctcaggctct ggggaaagga atctccctct   4920
cctctcactt gattccaagt gtggttgaat tgtctggagc actgggactt tttttctctt   4980
ttccttgatg gaccaacagt gcaaatgcaa tctcgccatt taactttcag gtcgatttcc   5040
tttcctgatc agacatcttt gtgccccctt taggaaggaa aagaatacac ctacgatgtg   5100
ccaggcactg tgttaggcgc ttttatatag atcctcgtta ggatgagact aagggatgag   5160
gacatctctt tataaaaggc ccctaagtaa tggataaaca gaaacactta gaggtgagaa   5220
ggtctgtctt caagatccaa ggtaagattg ccttcagtct gatgtttgtt ctcaaggact   5280
tatcccctac aatattctcc cactccatac ttctccttct accccaccat gtgctcccgt   5340
gcactcctca gatggtcaga ggggtaaccc aagtccttag agaatttggg gaccaataga   5400
atatgtgatg tgtgaatttt ctttaaaaaa cttaaggagt ctttgctacc ttctgcttgt   5460
```

```
tgagttgttt tggcattcat attaaaagcc agcatctcac tatttattga caggttgggc   5520
tgtgtgtgtg cgcatgtgtg tatacatttc caggcgtgcc tgtgtcctgt agctttttaa   5580
aaggaaaccc agtcatccca ctatgaatct ggcatcttct tatgcttcta gtgttttggc   5640
catacatcaa ccaaggggtt taatttatcc aatgcttgac gacatgttca ggaggggctg   5700
gatcaaattt tgagagggtt atgggaaagg gagggggaga agaaattgac atttatttta   5760
ttatttattt taaatgttta catcttcttt atgttgtatc aagcctgaat agaaactgat   5820
agcattaaaa tactccgttc ctctctctct tctcgcttcc tttttttttt ttttttttaaa   5880
tttaggataa cacattttg tttctaaagt gatttgtgat ttgtgctgta taaactgtat   5940
aaaaggttct gtttttaaag gtggattttc attcctctgg ggacagtggt cgccaagaca   6000
tctacattgt aagagaacac agtggaagat cctgtcctga ttctcaaaaa ttattttctc   6060
tgtatgatta aaagtttatt ccatttattt tagtttgtgt ttacttgatt ttgaggaaga   6120
aaatatttga ctttgtgtaa agagtagggt atcagggtgt cttttctgcc gtgggagatg   6180
tgtatatata tagtattttg gtgtatagta gaaaataagc tttgtgcatc tgtatttgag   6240
atatgttaat gacgtggagt aaagtcagct gtaagactct ggaggcaaac aagttgtata   6300
tggttcatat ggctctatgg ggaatttaat tacctttctg ggcacttttt tttttttttt   6360
ttttttaagt aatggtgaaa tggtcccatt ggagagtctc ctaaatagac cttccaggca   6420
gaaccgcaag ctcaaaatct ttgtatagtt ttgaaaattg aggagtagct ttgtttggaa   6480
gcctttctgg tggtggtttt tgttgttgtt gttgttttgt tgttttacta tatgtaatac   6540
aagcctacag tatttgcact aaagaaagct tgttagaaaa agcttgctgc tatggaagaa   6600
agaacatatt aaaacttctt tcccttgcga tttttttggg ggaggggggt tagcatttcc   6660
actttcagtt gagtagcatt ttgtagaata aaatgaatta agattgaaga gcc            6713
```

<210> SEQ ID NO 22
<211> LENGTH: 2041
<212> TYPE: DNA
<213> ORGANISM: Homo sapiens

<400> SEQUENCE: 22

```
agccatttct actttgcccg cccacagatg tagttttctc tgcgcgtgtg cgttttccct     60
cctccccgcc ctcagggtcc acggccacca tggcgtatta ggggcagcag tgcctgcggc    120
agcattggcc tttgcagcgg cggcagcagc accaggctct gcagcggcaa cccccagcgg    180
cttaagccat ggcgtgagta ccggggcggg tcgtccagct gtgctcctgg ggccggcgcg    240
ggttttggat tggtggggtg cggcctgggg ccagggcggt gccgccaagg gggaagcgat    300
ttaacgagcg cccgggacgc gtggtctttg cttgggtgtc cccgagacgc tcgcgtgcct    360
gggatcggga aagcgtagtc gggtgcccgg actgcttccc caggagccct acagccctcg    420
gaccccgagc cccgcaaggg tcccaggggt cttggctgtt gccccacgaa acgtggcagg    480
aaccaagatg gcggcggcag ggcggcggcg cgggcgtgag tcaagggcgg gcggtgggcg    540
gggcgcggcc gccctggccg tatttggacg tggggacgga gcgctttcct cttggcggcc    600
ggtggaagaa tcccctggtc tccgtgagcg tccattttgt ggaacctgag ttgcaagcag    660
ggaggggcaa atacaactgc cctgttcccg attctctaga tggccgatct agagaagtcc    720
cgcctcataa gtggaaggat gaaattctca gaacagctaa cctctaatgg gagttggctt    780
ctgattctca ttcaggcttc tcacggcatt cagcagcagc gttgctgtaa ccgacaaaga    840
```

caccttcgaa ttaagcacat tcctcgattc cagcaaagca ccgcaacatg accgaaatga 900
gcttcctgag cagcgaggtg ttggtggggg acttgatgtc ccccttcgac cagtcgggtt 960
tgggggctga agaaagccta ggtctcttag atgattacct ggaggtggcc aagcacttca 1020
aacctcatgg gttctccagc gacaaggcta aggcgggctc ctccgaatgg ctggctgtgg 1080
atgggttggt cagtccctcc aacaacagca aggaggatgc cttctccggg acagattgga 1140
tgttggagaa aatggatttg aaggagttcg acttggatgc cctgttgggt atagatgacc 1200
tggaaaccat gccagatgac cttctgacca cgttggatga cacttgtgat ctctttgccc 1260
ccctagtcca ggagactaat aagcagcccc cccagacggt gaacccaatt ggccatctcc 1320
cagaaagttt aacaaaaccc gaccaggttg ccccccttcac cttcttacaa cctcttcccc 1380
tttccccagg ggtcctgtcc tccactccag atcattcctt tagtttagag ctgggcagtg 1440
aagtggatat cactgaagga gataggaagc cagactacac tgcttacgtt gccatgatcc 1500
ctcagtgcat aaaggaggaa gacacccctt cagataatga tagtggcatc tgtatgagcc 1560
cagagtccta tctggggtct cctcagcaca gcccctctac caggggctct ccaaatagga 1620
gcctcccatc tccaggtgtt ctctgtgggt ctgcccgtcc caaaccttac gatcctcctg 1680
gagagaagat ggtagcagca aaagtaaagg gtgagaaact ggataagaag ctgaaaaaaa 1740
tggagcaaaa caagacagca gccactaggt accgccagaa gaagagggcg gagcaggagg 1800
ctcttactgg tgagtgcaaa gagctggaaa agaagaacga ggctctaaaa gagagggcgg 1860
attccctggc caaggagatc cagtacctga aagatttgat agaagaggtc cgcaaggcaa 1920
gggggaagaa aagggtcccc tagttgagga tagtcaggag cgtcaatgtg cttgtacata 1980
gagtgctgta gctgtgtgtt ccaataaatt attttgtagg gaaagtaaaa aaaaaaaaaa 2040
a 2041

<210> SEQ ID NO 23
<211> LENGTH: 5413
<212> TYPE: DNA
<213> ORGANISM: Homo sapiens

<400> SEQUENCE: 23
ctcagtcggg cgcagccgcc gccagggaaa agaaagggag gaaggaagga acaagaaaag 60
gaaataaaga gaaaggggag gcggggaaag gcaacgagct gtccggcctc cgtcaaggga 120
gttggaggga aaaagttctc aggcgccgca ggtccgagtg cctcgcagcc cctcccgagg 180
cgcagccgcc agaccagtgg agccggggcg cagggcgggg gcggaggcgc cggggcgggg 240
gatgcggggc cgcggcgcag ccccccggcc ctgagagcga ggacagcgcc gcccggcccg 300
cagccgtcgc cgcttctcca cctcggcccg tggagccggg gcgtccgggc gtagccctcg 360
ctcgcctggg tcagggggtg cgcgtcgggg gaggcagaag ccatggatcc cgggcagcag 420
ccgccgcctc aaccggcccc ccagggccaa gggcagccgc cttcgcagcc cccgcagggg 480
cagggcccgc cgtccggacc cgggcaaccg gcacccgcgg cgacccaggc ggcgccgcag 540 gcacccccccg ccgggcatca gatcgtgcac gtccgcgggg actcggagac cgacctggag 600
gcgctcttca acgccgtcat gaaccccaag acggccaacg tgccccagac cgtgcccatg 660
aggctccgga agctgcccga ctccttcttc aagccgccgg agcccaaatc ccactcccga 720
caggccagta ctgatgcagg cactgcagga gccctgactc cacagcatgt tcgagctcat 780
tcctctccag cttctctgca gttgggagct gtttctcctg ggacactgac ccccactgga 840
gtagtctctg gcccagcagc tacacccaca gctcagcatc ttcgacagtc ttcttttgag 900

```
atacctgatg atgtacctct gccagcaggt tgggagatgg caaagacatc ttctggtcag    960
agatacttct taaatcacat cgatcagaca acaacatggc aggaccccag gaaggccatg   1020
ctgtcccaga tgaacgtcac agccccccacc agtccaccag tgcagcagaa tatgatgaac  1080
tcggcttcag gtcctcttcc tgatggatgg gaacaagcca tgactcagga tggagaaatt   1140
tactatataa accataagaa caagaccacc tcttggctag acccaaggct tgaccctcgt   1200
tttgccatga accagagaat cagtcagagt gctccagtga aacagccacc accccctggct  1260
ccccagagcc cacagggagg cgtcatgggt ggcagcaact ccaaccagca gcaacagatg   1320
cgactgcagc aactgcagat ggagaaggag aggctgcggc tgaaacagca agaactgctt   1380
cggcaggtga ggccacaggc aatgcggaat atcaatccca gcacagcaaa ttctccaaaa   1440
tgtcaggagt tagccctgcg tagccagtta ccaacactgg agcaggatgg tgggactcaa   1500
aatccagtgt cttctcccgg gatgtctcag gaattgagaa caatgacgac caatagctca   1560
gatcctttcc ttaacagtgg cacctatcac tctcgagatg agagtacaga cagtggacta   1620
agcatgagca gctacagtgt ccctcgaacc ccagatgact tcctgaacag tgtggatgag   1680
atggatacag gtgatactat caaccaaagc accctgccct cacagcagaa ccgtttccca   1740
gactaccttg aagccattcc tgggacaaat gtggaccttg gaacactgga aggagatgga   1800
atgaacatag aaggagagga gctgatgcca agtctgcagg aagctttgag ttctgacatc   1860
cttaatgaca tggagtctgt tttggctgcc accaagctag ataaagaaag ctttcttaca   1920
tggttataga gccctcaggc agactgaatt ctaaatctgt gaaggatcta aggagacaca   1980
tgcaccggaa atttccataa gccagttgca gttttcaggc taatacagaa aaagatgaac   2040
aaacgtccag caagatactt taatcctcta ttttgctctt ccttgtccat tgctgctgtt   2100
aatgtattgc tgacctcttt cacagttggc tctaaagaat caaaagaaaa aaacttttta   2160
tttcttttgc tattaaaact actgttcatt ttgggggctg gggaagtga gcctgtttgg    2220
atgatggatg ccattccttt tgcccagtta aatgttcacc aatcatttta actaaatact   2280
cagacttaga agtcagatgc ttcatgtcac agcatttagt ttgttcaaca gttgtttctt   2340
cagcttcctt tgtccagtgg aaaaacatga tttactggtc tgacaagcca aaaatgttat   2400
atctgatatt aaatacttaa tgctgatttg aagagatagc tgaaaccaag gctgaagact   2460
gttttacttt cagtattttc ttttcctcct agtgctatca ttagtcacat aatgaccttg   2520
attttatttt aggagcttat aaggcatgag acaatttcca tataaatata ttaattattg   2580
ccacatactc taatatagat tttggtggat aattttgtgg gtgtgcattt tgttctgttt   2640
tgttgggttt tttgtttttt ttgtttttgg cagggtcggt gggggggttg gttggttggt   2700
tggttttgtc ggaacctagg caaatgacca tattagtgaa tctgttaata gttgtagctt   2760
gggatggtta ttgtagttgt tttggtaaaa tcttcatttc ctggtttttt ttaccacctt   2820
atttaaatct cgattatctg ctctctcttt tatatacata cacacaccca aacataacat   2880
ttataatagt gtggtagtgg aatgtatcct tttttaggtt tccctgcttt ccagttaatt   2940
tttaaaatgg tagcgctttg tatgcattta gaatacatga ctagtagttt atatttcact   3000
ggtagtttaa atctggttgg ggcagtctgc agatgtttga agtagtttag tgttctagaa   3060
agagctatta ctgtggatag tgcctagggg agtgctccac gccctctggg catacggtag   3120
atattatctg atgaattgga aaggagcaaa ccagaaatgg ctttattttc tcccttggac   3180
taatttttaa gtctcgattg gaattcagtg agtaggttca taatgtgcat gacagaaata   3240
```

-continued

```
agctttatag tggtttacct tcatttagct ttggaagttt tctttgcctt agttttggaa   3300

gtaaattcta gtttgtagtt ctcatttgta atgaacacat taacgactag attaaaatat   3360

tgccttcaag attgttctta cttacaagac ttgctcctac ttctatgctg aaaattgacc   3420

ctggatagaa tactataagg ttttgagtta gctggaaaag tgatcagatt aataaatgta   3480

tattggtagt tgaatttagc aaagaaatag agataatcat gattatacct ttatttttac   3540

aggaagagat gatgtaacta gagtatgtgt ctacaggagt aataatggtt tccaaagagt   3600

atttttaaa ggaacaaaac gagcatgaat taactcttca atataagcta tgaagtaata   3660

gttggttgtg aattaaagtg gcaccagcta gcacctctgt gttttaaggg tctttcaatg   3720

tttctagaat aagcccttat tttcaagggt tcataacagg cataaaatct cttctcctgg   3780

caaaagctgc tatgaaaagc ctcagcttgg gaagatagat tttttcccc ccaattacaa   3840

aatctaagta ttttggccct tcaatttgga ggagggcaaa agttggaagt aagaagtttt   3900

attttaagta ctttcagtgc tcaaaaaaat gcaatcactg tgttgtatat aatagttcat   3960

aggttgatca ctcataataa ttgactctaa ggcttttatt aagaaaacag cagaaagatt   4020

aaatcttgaa ttaagtctgg ggggaaatgg ccactgcaga tggagtttta gagtagtaat   4080

gaaattctac ctagaatgca aaattgggta tatgaattac atagcatgtt gttgggattt   4140

tttttaatgt gcagaagatc aaagctactt ggaaggagtg cctataattt gccagtagcc   4200

acagattaag attatatctt atatatcagc agattagctt tagcttaggg ggagggtggg   4260

aaagtttggg gggggggttg tgaagattta gggggacctt gatagagaac tttataaact   4320

tctttctctt taataaagac ttgtcttaca ccgtgctgcc attaaaggca gctgttctag   4380

agtttcagtc acctaagtac acccacaaaa caatatgaat atggagatct tcctttaccc   4440

ctcaacttta atttgcccag ttatacctca gtgttgtagc agtactgtga tacctggcac   4500

agtgctttga tcttacgatg ccctctgtac tgacctgaag gagacctaag agtcctttcc   4560

ctttttgagt ttgaatcata gccttgatgt ggtctcttgt tttatgtcct tgttcctaat   4620

gtaaaagtgc ttaactgctt cttggttgta ttgggtagca ttgggataag attttaactg   4680

ggtattcttg aattgctttt acaataaacc aattttataa tctttaaatt tatcaacttt   4740

ttacatttgt gttattttca gtcagggctt cttagatcta cttatggttg atggagcaca   4800

ttgatttgga gtttcagatc ttccaaagca ctatttgttg taataacttt tctaaatgta   4860

gtgcctttaa aggaaaaatg aacacaggga agtgactttg ctacaaataa tgttgctgtg   4920

ttaagtattc atattaaata catgccttct atatggaaca tggcagaaag actgaaaaat   4980

aacagtaatt aattgtgtaa ttcagaattc ataccaatca gtgttgaaac tcaaacattg   5040

caaaagtggg tggcaatatt cagtgcttaa cacttttcta gcgttggtac atctgagaaa   5100

tgagtgctca ggtggatttt atcctcgcaa gcatgttgtt ataagaattg tgggtgtgcc   5160

tatcataaca attgttttct gtatcttgaa aaagtattct ccacatttta aatgttttat   5220

attagagaat tctttaatgc acacttgtca aatatatata tatagtacca atgttacctt   5280

tttattttt gttttagatg taagagcatg ctcatatgtt aggtacttac ataaattgtt   5340

acattatttt ttcttatgta atacctttt gtttgtttat gtggttcaaa tatattcttt   5400

ccttaaactc ttc                                                      5413
```

<210> SEQ ID NO 24
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 24
nnnnnnnnnn nnnnnnnnnn gtttttgtac tctcaagatt tagaaataaa tcttgcagaa     60
gctacaaaga taaggcttca tgccgaaatc aacaccctgt cattttatgg cagggtgttt    120
tcgttattta atttttt                                                    137

<210> SEQ ID NO 25
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 25
nnnnnnnnnn nnnnnnnnnn gtttttgtac tctcagaaat gcagaagcta caaagataag     60
gcttcatgcc gaaatcaaca ccctgtcatt ttatggcagg gtgttttcgt tatttaattt    120
ttt                                                                   123

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 26
nnnnnnnnnn nnnnnnnnnn gtttttgtac tctcagaaat gcagaagcta caaagataag     60
gcttcatgcc gaaatcaaca ccctgtcatt ttatggcagg gtgttttttt               110

<210> SEQ ID NO 27
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 27
nnnnnnnnnn nnnnnnnnnn gttttagagc tagaaatagc aagttaaaat aaggctagtc 60
cgttatcaac ttgaaaaagt ggcaccgagt cggtgctttt tt 102

<210> SEQ ID NO 28
<211> LENGTH: 88
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 28
nnnnnnnnnn nnnnnnnnnn gttttagagc tagaaatagc aagttaaaat aaggctagtc 60
cgttatcaac ttgaaaaagt gttttttt 88

<210> SEQ ID NO 29
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<223> OTHER INFORMATION: See specification as filed for detailed description of substitutions and preferred embodiments

<400> SEQUENCE: 29
nnnnnnnnnn nnnnnnnnnn gttttagagc tagaaatagc aagttaaaat aaggctagtc 60
cgttatcatt tttttt 76

<210> SEQ ID NO 30
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(11)
<223> OTHER INFORMATION: a, c, t, g, unknown or other
<220> FEATURE:
<221> NAME/KEY: modified_base
<222> LOCATION: (14)..(18)
<223> OTHER INFORMATION: a, c, t, g, unknown or other
<220> FEATURE:
<221> NAME/KEY: modified_base
<222> LOCATION: (21)..(25)
<223> OTHER INFORMATION: a, c, t, g, unknown or other

<400> SEQUENCE: 30
cccggtnnnn naannnnntt nnnnnaatgt ctagtactaa tcactggata aaactgcggt 60
cgt 63